(12) United States Patent
Skelton et al.

(10) Patent No.: US 9,662,045 B2
(45) Date of Patent: May 30, 2017

(54) GENERATION OF SLEEP QUALITY INFORMATION BASED ON POSTURE STATE DATA

(75) Inventors: Dennis M. Skelton, Bloomington, MN (US); Jon P. Davis, St. Michael, MN (US); Rajeev Sahasrabudhe, Maple Grove, MN (US); Shyam Gokaldas, New Brighton, MN (US)

(73) Assignee: Medtronic, Inc., Minneapolis, MN (US)

(*) Notice: Subject to any disclaimer, the term of this patent is extended or adjusted under 35 U.S.C. 154(b) by 2287 days.

(21) Appl. No.: 12/433,632

(22) Filed: Apr. 30, 2009

(65) Prior Publication Data
US 2010/0010385 A1 Jan. 14, 2010

Related U.S. Application Data

(60) Provisional application No. 61/080,000, filed on Jul. 11, 2008.

(51) Int. Cl.
*A61B 5/00* (2006.01)
*A61B 5/11* (2006.01)
(Continued)

(52) U.S. Cl.
CPC .......... *A61B 5/1116* (2013.01); *A61B 5/4815* (2013.01); *A61B 5/6846* (2013.01); *A61N 1/36078* (2013.01); *A61N 1/36132* (2013.01); *A61N 1/37247* (2013.01); *A61N 1/37282* (2013.01); *A61B 5/0031* (2013.01); *A61B 5/1118* (2013.01); *A61B 5/686* (2013.01); *A61B 2560/0219* (2013.01); *A61N 1/0551* (2013.01); *A61N 1/36071* (2013.01); *A61N 1/36085* (2013.01); *A61N 1/36107* (2013.01); *A61N 1/36535* (2013.01)

(58) Field of Classification Search
CPC ............................ A61B 5/1116; A61B 5/4815
USPC .................................... 607/62; 600/301, 508
See application file for complete search history.

(56) References Cited

U.S. PATENT DOCUMENTS 4,297,685 A 10/1981 Brainard, II
4,365,633 A 12/1982 Loughman
(Continued)

FOREIGN PATENT DOCUMENTS

CN 101076283 A 11/2007
DE 19831109 1/2000
(Continued)

OTHER PUBLICATIONS

"Analysis of heart rate dynamics by methods derived from nonlinear mathematics: Clinical applicability and prognostic significance," http://herkules.oulu.fi.isbn9514250133/html, 4 pp., 2004.
(Continued)

*Primary Examiner* — Nadia A Mahmood
(74) *Attorney, Agent, or Firm* — Shumaker & Sieffert, P.A.

(57) ABSTRACT

This disclosure describes techniques for generation of sleep quality information based on posture state data. The techniques may include obtaining posture state data sensed by a medical device for a patient, generating sleep quality information based on lying posture state changes indicated by the posture state data, and presenting the sleep quality information to a user via a user interface.

41 Claims, 41 Drawing Sheets

(51) Int. Cl.
  *A61N 1/372* (2006.01)
  *A61N 1/05* (2006.01)
  *A61N 1/36* (2006.01)
  *A61N 1/365* (2006.01)

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,617,525 A | 10/1986 | Lloyd |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,038,137 A | 8/1991 | Lloyd |
| 5,040,534 A | 8/1991 | Mann et al. |
| 5,040,536 A | 8/1991 | Riff |
| 5,058,584 A | 10/1991 | Bourgeois |
| 5,082,002 A | 1/1992 | Silverman et al. |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,243,998 A | 9/1993 | Silverman et al. |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,070,568 B1 | 7/2006 | Koh |
| 7,082,333 B1 | 7/2006 | Bauhahn |
| 7,092,759 B2 | 8/2006 | Nehls et al. |

(56) References Cited

U.S. PATENT DOCUMENTS

| | | |
|---|---|---|
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,206,635 B2 | 4/2007 | Cho et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,226,422 B2 | 6/2007 | Hatlestad et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,309 B1 | 12/2007 | Koh |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,643,655 B2 | 1/2010 | Liang et al. |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 8,032,224 B2 | 10/2011 | Miesel et al. |
| 8,032,229 B2 | 10/2011 | Gerber et al. |
| 8,065,001 B1 | 11/2011 | Nabutovsky et al. |
| 8,150,531 B2 | 4/2012 | Skelton |
| 8,175,720 B2 | 5/2012 | Skelton et al. |
| 8,200,340 B2 | 6/2012 | Skelton et al. |
| 8,209,028 B2 | 6/2012 | Skelton et al. |
| 8,219,206 B2 | 7/2012 | Skelton et al. |
| 8,231,555 B2 | 7/2012 | Skelton et al. |
| 8,231,556 B2 | 7/2012 | Skelton et al. |
| 8,249,718 B2 | 8/2012 | Skelton et al. |
| 8,280,517 B2 | 10/2012 | Skelton et al. |
| 8,282,580 B2 | 10/2012 | Skelton et al. |
| 8,290,726 B2 | 10/2012 | Schmidt et al. |
| 8,315,710 B2 | 11/2012 | Skelton et al. |
| 8,323,218 B2 | 12/2012 | Davis et al. |
| 8,326,420 B2 | 12/2012 | Skelton et al. |
| 8,332,041 B2 | 12/2012 | Skelton et al. |
| 8,388,555 B2 | 3/2013 | Panken et al. |
| 8,401,666 B2 | 3/2013 | Skelton et al. |
| 8,437,861 B2 | 5/2013 | Skelton et al. |
| 8,447,411 B2 | 5/2013 | Skelton et al. |
| 8,515,549 B2 | 8/2013 | Panken et al. |
| 8,515,550 B2 | 8/2013 | Skelton et al. |
| 8,583,252 B2 | 11/2013 | Skelton et al. |
| 8,588,929 B2 | 11/2013 | Skelton et al. |
| 8,644,945 B2 | 2/2014 | Skelton et al. |
| 8,708,934 B2 | 4/2014 | Skelton et al. |
| 8,751,011 B2 | 6/2014 | Skelton et al. |
| 8,755,901 B2 | 6/2014 | Skelton et al. |
| 8,886,302 B2 | 11/2014 | Skelton et al. |
| 8,905,948 B2 | 12/2014 | Davis et al. |
| 9,026,223 B2 | 5/2015 | Skelton et al. |
| 9,050,471 B2 | 6/2015 | Skelton et al. |
| 9,272,091 B2 | 3/2016 | Skelton et al. |
| 9,327,070 B2 | 5/2016 | Skelton et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2003/0204415 A1 | 10/2003 | Knowlton |
| 2004/0015103 A1 | 1/2004 | Aminian et al. |
| 2004/0049132 A1 | 3/2004 | Barron et al. |
| 2004/0073128 A1 | 4/2004 | Hatlestad et al. |
| 2004/0088020 A1 | 5/2004 | Condie et al. |
| 2004/0097814 A1 | 5/2004 | Navakatikyan et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2004/0267330 A1 | 12/2004 | Lee et al. |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0107722 A1* | 5/2005 | Ozaki et al. .................. 600/587 |
| 2005/0113710 A1 | 5/2005 | Stahmann et al. |
| 2005/0113887 A1 | 5/2005 | Bauhahn |
| 2005/0115561 A1 | 6/2005 | Stahmann et al. |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |

(56) References Cited

U.S. PATENT DOCUMENTS

| | | |
|---|---|---|
| 2005/0177192 A1 | 8/2005 | Rezai et al. |
| 2005/0209511 A1* | 9/2005 | Heruth et al. ............... 600/301 |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0216067 A1 | 9/2005 | Min et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0017575 A1 | 1/2006 | Mcadams |
| 2006/0030892 A1 | 2/2006 | Kadhiresan et al. |
| 2006/0047538 A1 | 3/2006 | Condurso et al. |
| 2006/0064136 A1 | 3/2006 | Wang et al. |
| 2006/0094967 A1 | 5/2006 | Bennett et al. |
| 2006/0161070 A1 | 7/2006 | Siejko et al. |
| 2006/0173257 A1 | 8/2006 | Nagai et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0195149 A1 | 8/2006 | Hopper et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0224190 A1 | 10/2006 | Gill et al. |
| 2006/0235289 A1 | 10/2006 | Wesselink et al. |
| 2006/0235302 A1 | 10/2006 | Grossman et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0253006 A1 | 11/2006 | Bardy |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0276848 A1 | 12/2006 | Min et al. |
| 2006/0287686 A1 | 12/2006 | Cullen et al. |
| 2006/0293609 A1 | 12/2006 | Stahmann et al. |
| 2007/0015976 A1 | 1/2007 | Miesel et al. |
| 2007/0021678 A1 | 1/2007 | Beck et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118054 A1 | 5/2007 | Pinhas et al. |
| 2007/0118056 A1 | 5/2007 | Wang et al. |
| 2007/0123758 A1 | 5/2007 | Miesel et al. |
| 2007/0123953 A1 | 5/2007 | Lee et al. |
| 2007/0129622 A1 | 6/2007 | Bourget et al. |
| 2007/0129641 A1 | 6/2007 | Sweeney |
| 2007/0129643 A1 | 6/2007 | Kwok et al. |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0156057 A1 | 7/2007 | Cho et al. |
| 2007/0161912 A1 | 7/2007 | Zhang et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0255334 A1 | 11/2007 | Keimel et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0264426 A1 | 10/2008 | Walker et al. |
| 2008/0269812 A1 | 10/2008 | Gerber et al. |
| 2008/0269843 A1 | 10/2008 | Gerber |
| 2008/0275349 A1 | 11/2008 | Halperin et al. |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0024005 A1 | 1/2009 | Lewicke et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0048538 A1 | 2/2009 | Levine et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0112289 A1 | 4/2009 | Lee et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0234200 A1 | 9/2009 | Husheer |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0015077 A1 | 1/2010 | Adams et al. |
| 2010/0030286 A1 | 2/2010 | Goetz et al. |
| 2010/0113961 A1 | 5/2010 | Ohlander et al. |

(56) References Cited

U.S. PATENT DOCUMENTS

| | | |
|---|---|---|
| 2010/0121415 A1 | 5/2010 | Skelton et al. |
| 2010/0174155 A1 | 7/2010 | Heruth et al. |
| 2010/0217135 A1 | 8/2010 | Cho et al. |
| 2010/0280500 A1 | 11/2010 | Skelton et al. |
| 2011/0172562 A1 | 7/2011 | Sahasrabudhe et al. |
| 2011/0172567 A1 | 7/2011 | Panken et al. |
| 2011/0270134 A1 | 11/2011 | Skelton |

FOREIGN PATENT DOCUMENTS

| | | |
|---|---|---|
| DE | 10024103 | 11/2001 |
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad", http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT- University of Health Systems, Medical Informatics and Technology Hall in Tyrol, Austria, 2006 5 pp. http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., Sensing Techniques for Mobile Interaction, ACM UIST 2000 Symposium on User Interface Software & Technology, CHI Letters 2 (2), pp. 91-100.

Husak, "Model of Tilt Sensor Systems," ICECS 2002, $9^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

(56) References Cited

OTHER PUBLICATIONS

Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—9$^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/48260: International Search Report and Written Opinion dated Sep. 10, 2009, 16 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
Final Office Action dated Jan. 25, 2012 for U.S. Appl. No. 12/433,785, (12 pgs.).
Request for Continued Examination and Responsive Amendment dated Apr. 25, 2012 for U.S. Appl. No. 12/433,785 (16 pgs.).
Office Action dated Sep. 7, 2011 for U.S. Appl. No. 12/433,785, (10 pgs.).
Responsive Amendment dated Jan. 6, 2012 for U.S. Appl. No. 12/433,785, (14 pgs.).
Office Action from U.S. Appl. No. 13/665,675, dated Mar. 26, 2013, 23 pp.
Response to Office Action dated Apr. 4, 2014, from U.S. Appl. No. 13/665,675, filed Jul. 2, 2014, 9 pp.
Notice of Allowance from U.S. Appl. No. 13/665,675, dated Aug. 5, 2014, 12 pp.

\* cited by examiner

GENERATION OF SLEEP QUALITY INFORMATION BASED ON POSTURE STATE DATA

This application claims the benefit of U.S. provisional application No. 61/080,000, filed Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure provides a method and system for generating and presenting posture state-related information to a user via a user interface of a patient or clinician programmer. The posture state-related information may be presented to support objectification of efficacy of posture state-responsive therapy to a patient. The posture state-related information may include a variety of information such as sleep quality information, proportional posture information, and quantified therapy adjustments made by the patient. Information obtained based on posture state data from short therapy sessions may be rejected in generating the posture state-related information to avoid the use of unreliable data.

In one example, the disclosure provides a method comprising obtaining posture state data sensed by a medical device for a patient, generating sleep quality information based on lying posture state changes indicated by the posture state data, and presenting the sleep quality information to a user via a user interface.

In another example, the disclosure provides a system comprising a processor that obtains posture state data sensed by a medical device for a patient, and generates sleep quality information based on lying posture state changes indicated by the posture state data, and a user interface that presents the sleep quality information to a user.

In another example, the disclosure provides a device comprising a telemetry interface, a processor that obtains posture state data sensed by an implantable medical device via the telemetry interface, and generates sleep quality information based on lying posture state changes indicated by the posture state data, and a user interface that presents the sleep quality information to a user.

In another example, the disclosure provides a method comprising obtaining posture state data sensed by a medical device for a patient during delivery of therapy by the medical device, determining durations for which the patient occupied each of a plurality of posture states based on the posture state data, generating proportional posture information for a plurality of different time intervals based on the durations, wherein the proportional posture information for each of the time intervals indicates proportional amounts of the respective time interval in which the patient occupied the posture states, and presenting the proportional posture information to a user via a user interface.

In another example, the disclosure provides a system comprising a processor that obtains posture state data sensed by a medical device for a patient during delivery of therapy by the medical device, determines durations for which a patient occupied each of a plurality of posture states based on the posture state data, and generates proportional posture information for a plurality of different time intervals based on the durations, wherein the proportional posture information for each of the time intervals indicates proportional amounts of the respective time interval in which the patient occupied the posture states, and a user interface that presents the proportional posture information to a user.

In another example, the disclosure provides a device comprising a telemetry interface, a processor that obtains, via the telemetry interface, posture state data sensed by a medical device for a patient during delivery of therapy by the medical device, determines durations for which a patient occupied each of a plurality of posture states based on the posture state data, and generates proportional posture information for a plurality of different time intervals based on the durations, wherein the proportional posture information for each of the time intervals indicates proportional amounts of the respective time interval in which the patient occupied the posture states, and a user interface that presents the proportional posture information to a user.

In another example, the disclosure provides a method comprising accumulating posture state data sensed by a medical device for a patient during therapy sessions between successive programming sessions of the medical device, wherein the medical device delivers therapy to the patient during each of the therapy sessions, determining durations for which the patient occupied each of a plurality of posture states during the therapy sessions based on the posture state data, wherein lengths of at least some of the therapy sessions are different, generating proportional posture information for the therapy sessions based on the durations, wherein the proportional posture information indicates, for each of the therapy sessions, proportional amounts of the respective therapy session in which the patient occupied the posture states, and presenting the proportional posture information to a user via a user interface.

In another example, the disclosure provides a method comprising sensing posture states of a patient, delivering posture-state responsive electrical stimulation therapy to the patient based on the sensed posture states, receiving patient adjustments to the electrical stimulation therapy delivered to the patient, determining a number of the patient adjustments received over a time interval, and presenting a representation of the number of the patient adjustments received over the time interval to a user.

In another example, the disclosure provides a system comprising a sensor that senses posture states of a patient, a stimulation generator that delivers posture-state responsive electrical stimulation therapy to the patient based on the sensed posture states, an input device that receives patient adjustments to the electrical stimulation therapy delivered to the patient, a processor that determines a number of the patient adjustments received over a time interval, and a user interface that presents a representation of the number of the patient adjustments received over the time interval to a user via a user interface.

In another example, the disclosure provides a method comprising storing posture state data sensed by a medical device for a patient, rejecting any portion of the posture state data that was stored during a session that was shorter than a session threshold, and generating posture state output for the patient based on a portion of the posture state data that was not rejected.

In another example, the disclosure provides a system comprising a memory that stores posture state data sensed by a medical device for a patient, and a processor that rejects any portion of the posture state data that was stored during a session that was shorter than a session threshold, and generates posture state output for the patient based on a portion of the posture state data that was not rejected.

The details of one or more aspects of the disclosure are set forth in the accompanying drawings and the description below. Other features, objects, and advantages will be apparent from the description and drawings, and from the claims.

DETAILED DESCRIPTION

Figure 1A:
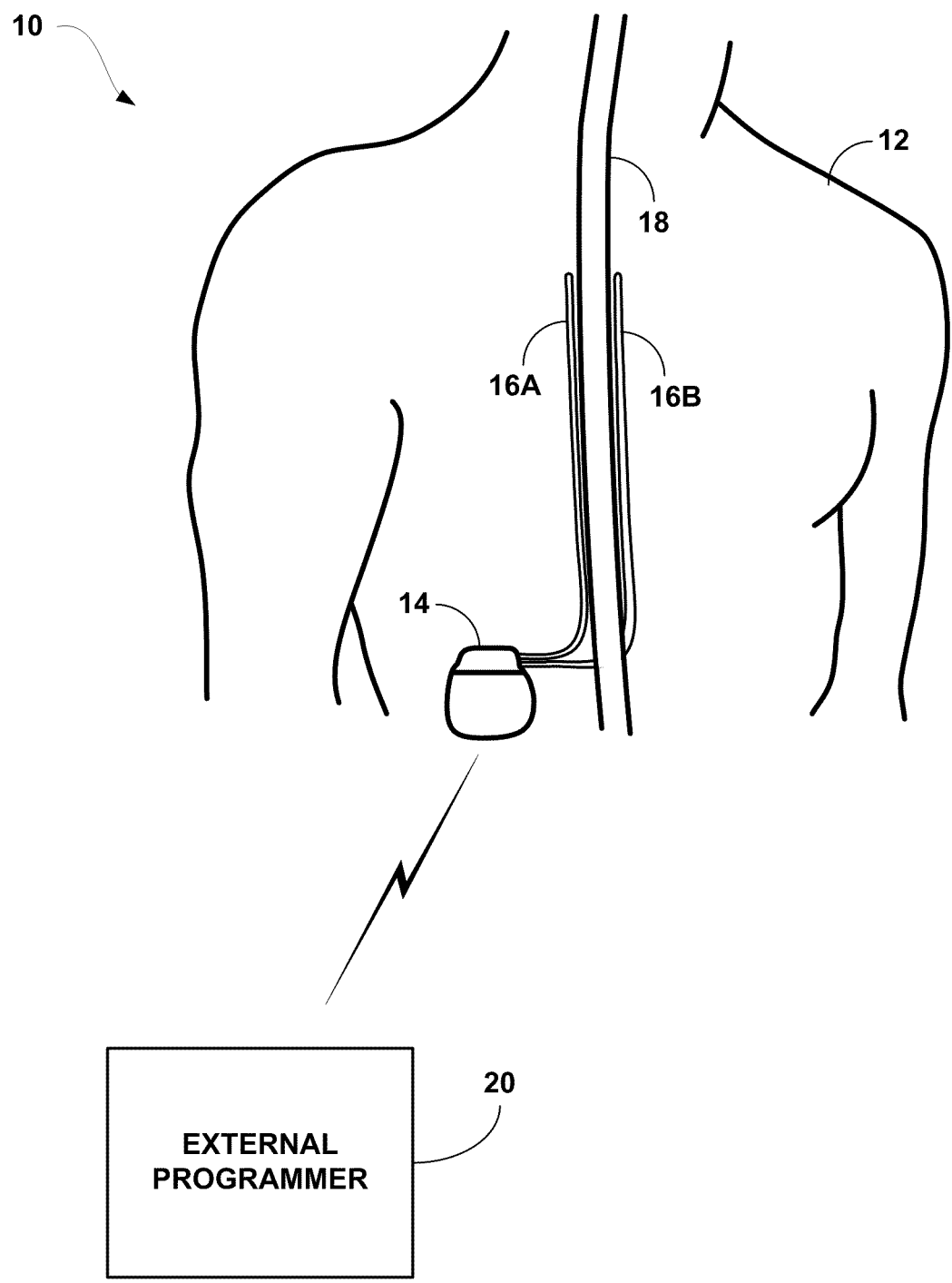
FIG. 1A is a conceptual diagram illustrating an implantable stimulation system including two implantable stimulation leads.

In some medical devices that deliver electrical stimulation therapy, therapeutic efficacy may change as the patient changes posture states throughout the daily routine of the patient. In general, a posture state may refer to a patient posture or a combination of posture and activity. For example, some posture states, such as upright, may be sub-categorized as upright and active or upright and inactive. Other posture states, such as lying down posture states, may or may not have an activity component. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., a pain level of the patient. To maintain therapeutic efficacy, it may be desirable to adjust therapy parameters based on different postures and/or activities engaged by the patient to maintain effective stimulation therapy. Therapy parameters may be adjusted directly, e.g., manual adjustment of one or more stimulation parameters, or by selecting different programs or groups of programs defining different sets of therapy parameters.

A change in efficacy due to changes in posture state may require the patient to continually manage therapy by manually adjusting certain therapy parameters, such as amplitude, pulse rate, pulse width, or electrode combinations, or selecting different therapy programs to achieve more efficacious therapy throughout many different posture states. In some cases, a medical device may employ a posture state detector that detects the patient posture state. The medical device may automatically adjust therapy parameters in response to different posture states, thereby providing posture state-responsive therapy. Therapy adjustments in response to different posture states may be fully automatic, semi-automatic in the sense that a user may provide approval of proposed changes, or user-directed in the sense that the patient may manually adjust therapy based on the posture state indication.

During stimulation therapy or diagnostic monitoring, the patient may be engaged or desire to be engaged in different posture states, e.g., postures and activities. The patient may avoid or occupy less time in certain posture states because a particular condition may cause pain, discomfort, or the inability to assume some posture states. A system may be configured to sense when the patient is in each posture state, store posture state-related information, and present the posture state-related information to a clinician or patient as objective data related to the condition of the patient.

This disclosure is directed to presenting posture state data to facilitate analysis of the patient's posture states, therapy adjustments, and evaluation of the effectiveness of a therapy currently delivered to the patient, such as a posture state-responsive therapy. In some cases, presentation of posture state data as described in this disclosure may aid a clinician in adjusting therapy parameter values to improve therapeutic efficacy. Symptoms caused by many different diseases, disorders or conditions, e.g., chronic pain, tremor, Parkinson's disease, epilepsy, urinary or fecal incontinence, sexual dysfunction, obesity, or gastroparesis, can affect the postures and activities in which the patient chooses to engage. By monitoring the patient's posture and activity, a user, e.g., a clinician, may be able to objectively identify troublesome postures and activities in addition to trends that show improvements or degradations in therapy efficacy.

An implantable medical device (IMD) implanted within the patient may include a posture state module containing a posture state sensor capable of sensing the posture state of the patient. The posture state may include a specific posture of the patient and/or the specific activity conducted by the patient. After the posture state is sensed or detected, that posture state may be stored within the memory as part of the overall posture state data of the IMD or other device for later retrieval and review. The IMD may store each different posture state engaged by the patient, the posture duration of each posture state, the number of transitions, i.e., changes, between each posture state as the patient moves, or any other posture state data derived from the posture state sensor. In this manner, the IMD may store a posture state history for retrieval and analysis.

The user may review the posture state data to objectively determine the patient's condition and, in some cases, evaluate possible modifications to therapy parameters. The user may prefer to organize the posture state data as sleep quality information or proportional posture information to more easily analyze the posture state data. The sleep quality information and proportional posture information may be presented numerically graphically as a chart or graph, in addition or as an alternative to presentation of the information as quantified values for the duration of each posture state or number of posture state transitions during a time interval, either as an absolute value or on average.

For example, the sleep quality information may be presented as a sleep quality chart or graph that graphically and numerically indicates the average number of posture state transitions while the patient is lying down during one or more time intervals. A sleep quality graph that graphically and/or numerically displays the sleep quality information may allow the user to quickly identify objective data and possible trends that may provide insight into therapy parameters that provide effective therapy to the patient. The time intervals may be therapy sessions during which therapy is delivered. Each therapy session may be a period of time between successive programming session in which a medical device is programmed to deliver therapy, such as posture state-responsive therapy. The terms "posture state transitions" and "posture state changes" may be used generally on an interchangeable basis in this disclosure. The chart may show that more recent months show fewer posture state changes during lying down to indicate, for example, that recent stimulation therapy may be more effective in treating the patient's chronic pain.

In addition, or alternatively, proportional posture information may be presented numerically or graphically as an average percentage of time the patient engages in different posture states, such as lying, upright, and active posture states, for different time intervals, such as a series of therapy sessions. For each therapy session, a medical device may apply therapy parameters specified in a programming sessions. By comparing posture state results for different therapy sessions, it may be possible to observe an efficacy trend resulting from application of different therapy parameters. If more recent time intervals show that the patient is engaged in more upright and active posture states, then the user may infer that stimulation therapy, e.g., posture state-responsive therapy, is being effective in treating the patient's condition. In particular, upright and active posture states may be associated with more patient activity than lying posture states. A greater proportion of time spent in active or upright postures may indicate efficacy of parameters applied in therapy sessions associated with the respective time intervals.

Generally, the sleep quality information and proportional posture information may be presented to a clinician via a clinician programmer or another programming or viewing device. The clinician may then monitor the therapy, sleep quality information, and/or proportional posture information to recognize any trends in the patient condition, e.g., during delivery of posture state-responsive therapy to the patient. The clinician may view the information when the patient comes in for a clinic visit or remotely via a networked connection between the patient programmer and an external device. Alternatively, the patient may view the sleep quality information and proportional posture information to monitor their progress due to therapy or view the monitored posture state data. In any case, presenting the sleep quality information and/or proportional posture information to a user, such as a clinician or patient, may allow for more objective posture state monitoring than could be provided by manual patient logging or periodic patient surveys of subjective pain, activity, posture or other information.

In addition, the system may generate and present a number of posture state adjustments during the one or more time intervals, such as therapy sessions. In each therapy session, a medical device may apply therapy, such as posture state-responsive therapy, according to therapy parameters specified by a clinician in a previous programming session, e.g., in-clinic or remote. The posture state adjustments may provide an indication of efficacy of such parameters. In some cases, the number of posture state adjustments may be an average number of adjustments for each posture state over one or more time intervals, such as one or more therapy sessions. The number of posture state adjustments may indicate the effectiveness of a stimulation therapy, such as a posture state-responsive therapy, in allowing the patient to conduct various activities. More posture state adjustments, or changes from one posture state to another, may suggest that the patient is able to be more active because the stimulation therapy is suppressing prior pain symptoms. The posture state adjustments may be presented graphically, numerically, or concurrently on the same screen of the user interface.

The system also may generate and present a number of patient therapy adjustments during one or more time intervals, such as therapy sessions. Again, in each therapy session, a medical device may apply therapy, such as posture state-responsive therapy, according to therapy parameters specified by a clinician in a previous programming session, e.g., in-clinic or remote. The patient therapy adjustments may provide an indication of efficacy of such parameters. For example, if the patient makes few adjustments to therapy parameters, it may be inferred that current therapy parameters are generally effective in addressing the patient's condition. If the patient makes more numerous therapy adjustments, however, the current therapy parameters may require modification to enhance efficacy.

The number of patient therapy adjustments may be indicated for particular posture states. For example, a medical device may track the number of adjustments by the patient upon entering a particular posture state, possibly with the use of an adjustment timer that tracks the number of adjustments within a particular period of time following sensing of transition to a new posture state. In some cases, the number of posture state adjustments may be an average number of patient therapy adjustments for each posture state over one or more time intervals. The number of patient therapy adjustments may indicate the effectiveness of a stimulation therapy, such as a posture state-responsive therapy. More patient therapy adjustments may suggest that the patient is having relatively greater difficulty in finding suitable therapy parameter settings. The number of therapy adjustments may be presented graphically, numerically, or concurrently for one posture state or multiple posture states, and for one time interval or multiple time intervals, on the same screen of the user interface.

Whether the system generates sleep quality information, proportional posture information, posture state change information, patient therapy adjustment information, or any other type of posture state information, it may not be necessary to use all stored posture state data to generate the information. Use of posture state data sensed and stored during very short time intervals, such as very short therapy sessions, may not be desirable because this data may skew the remainder of the posture state data. A therapy session generally refers to any therapy duration, e.g., a time between successive programming sessions which may be associated with clinic visits, the time between changes in therapy parameter values of programs or groups, the overall time therapy was turned on during any giving time interval, or any other measure of a therapy duration. In some cases, a therapy session may be a time between successive programming sessions, which may include in-clinic or remote programming sessions.

In general, in generating posture state output, a programmer or IMD may reject any portion of the posture state data that was stored during a session that was shorter than a session threshold. For example, any posture state data stored when less than twenty four hours elapsed between programming sessions, e.g., between clinician visits by the patient, may be rejected because of this short therapy session. In a programming sessions associated with a clinician visit, or in a remote programming session, the clinician may make substantial adjustments to therapy parameter values to be delivered by the medical device during a therapy session. Posture state information obtained when therapy parameter values are applied for only a short period of time may be less reliable and useful than posture state information obtained for therapy parameter values applied over a longer period of time. In some cases, a short therapy session may result when the clinician is interrupted during a programming session. The resulting programming may be incomplete or otherwise not ideal, but therapy may be delivered for a short period of time until the clinician can initiate another programming session to complete the programming. To avoid adding unreliable data from the short session, or possibly overwriting good data with new data from the short therapy session, posture state information obtained during the short therapy session can be rejected, e.g., discarded rather than stored.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG. 1A, IMD 14 is an implantable electrical stimulator configured for spinal cord stimulation (SCS), e.g., for relief of chronic pain or other symptoms. Again, although FIG. 1A shows an implantable medical device, other embodiments may include an external stimulator (not shown), e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation device that is used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue may include nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In exemplary embodiments, IMD 14 delivers stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, and an electrode combination (e.g., combination of electrodes and polarities) for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis or other time-ordered basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. For example, stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy. Also, posture state changes may present changes in symptoms or symptom levels, e.g., the pain level of patient 12.

Many other examples of reduced efficacy due to increased coupling or decreased coupling of stimulation energy to target tissue, or changes in symptoms or symptom levels, may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change.

A user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

External programmer 20 may present posture state data stored in IMD 14 from the detected posture states of patient 12. The posture state data may be acquired by external programmer 20 to generate posture state information, e.g., sleep quality information, proportional posture information, or other information that objectively indicates how patient 12 has been moving during therapy. External programmer 20 may provide a user interface to present the posture state information graphically as a chart or graph, numerically, or some combination thereof. The posture state information may be specific to a specific time interval, e.g., a day, a week, a month, or a year. In some cases, the time interval may be open-ended in that it depends on the length of a therapy session during which the posture state information is collected, which in turn is dependent on the timing of successive programming sessions in which therapy parameters for delivery of therapy were specified. The posture state information may include multiple posture state determinations made during a time interval, such as therapy session. In some examples, the posture state information may be averaged over a time period, such as a daily average over a month time interval. The time interval may be any time period defined by the patient, and therapy may occur over multiple time intervals. Alternatively, if the therapy session length varies according to the time during programming sessions, then the posture state information may be accumulated and averaged over the entire therapy session length.

The sleep quality information may be presented as a sleep quality chart showing the actual or average number of transitions, or changes, between two or more lying down posture states during a time interval. IMD 14 may recognize four different lying down posture states: lying down on the chest (lying front), lying down on the back (lying back), lying on the right side (lying right), and lying on the left side (lying left). Therefore, changes between consecutive lying down posture states may be used to detect that patient 12 is sleeping, or is attempting to sleep. Therefore, increased changes between lying down posture states may indicate that patient 12 is restless and is not achieving deep sleep, possibly due to symptoms such as pain. The clinician or patient 12 may desire to adjust therapy in order to better treat patient 12 when lying down so that the number of changes between lying down postures is reduced. In addition, the sleep quality information may quantify the number of times patient 12 leaves each lying down posture or moves to another lying down posture. This information may be helpful in determining how therapy can be improved.

The proportional posture information may be presented as a graph showing the percentage of time patient 12 engaged in each posture state in a time interval, such as a therapy session. The percentage of time is the posture duration, and the posture duration may be calculated for a single day, an average day within a specific time interval, or overall average within a specific time interval, for example. Other combinations and averages are also contemplated as indicative of the proportion of time patient 12 engaged in one or more posture states during a time interval. In addition to the posture duration, the quantified number of times patient 12 was engaged in the pertinent posture state during the time interval may also be presented. A greater posture duration along with a fewer number of times that patient 12 has engaged in or transitioned to or from the posture state may indicate that the therapy is relieving symptoms sufficiently to allow patient 12 to be engaged in the posture state for a longer period of time. The proportional posture information may include some or all of the posture state data stored during patient 12 therapy.

Posture state data, such as detected posture states or posture state transitions, may be obtained over time intervals of predetermined length or indeterminate length. For example, IMD 14 may be configured to obtain and store posture state data over a specified time interval or one day, one week or one month. Alternatively, IMD 14 may be configured to obtain and store posture state data over an indeterminate time interval, such as a therapy session running between successive therapy programming sessions.

At the time a therapy session is initiated following a programming session, the timing of the next programming session may be unknown. Nevertheless, IMD 14 may be constructed to accumulate posture state data over the length of the therapy session, without regard to specified time intervals. In this case, posture information such as proportional posture information, sleep quality information, posture change information, or patient therapy adjustment information may be generated for the entire therapy session, e.g., as an absolute number over the therapy session or as an average number over a portion of the therapy session, such as a day, week or month of the therapy session.

In some cases, posture state data may be simply accumulated over the course of a therapy session without date-stamping, time-stamping or otherwise associating the data with a particular time interval. Instead, the number of counts of a posture state, posture state transition, or patient therapy adjustment are accumulated. In addition, the duration of each posture state may be tracked with another accumulator that accumulates the length of time the patient occupies each posture state, taking into account each time that the patient initially occupies the posture state and then transitions to another posture state.

To produce posture information, IMD 14 or an external programmer 20 may then analyze the stored posture state data over the length of the applicable time interval, i.e., the applicable therapy session. To calculate an average number of patient therapy adjustments for a given posture state over a period of time, for example, IMD 14 or programmer 20 divide the number of patient therapy adjustments detected in the therapy session by the number of applicable time periods in the therapy session.

For an average number of patient therapy adjustments for the lying back posture state per week, IMD 14 or programmer counts the number of patient therapy adjustments over the entire therapy session, and divides that count by the number of weeks in the applicable therapy session. If the count was 50, and the length of the therapy session was 4.5 weeks, then the weekly average would be approximately 11.1. If the therapy session was 6.2 weeks, the weekly average would be approximately 8.1, and the monthly average (assuming 30 days per month) would be approximately 34.6.

If this accumulation technique is used without date-stamping, it may not be possible to generate the number of patient therapy adjustments (or other statistics) in a particular time interval, such as a particular week or month. For example, if a therapy session is six weeks long, it may not be possible to generate the number of average number of patient therapy adjustments for the first week. Instead, with accumulated data, the weekly average or monthly average is obtained considering the therapy session as a whole.

However, the use of accumulated data can significantly simplify the design and operation of IMD 14 or programmer 20 in storing posture state data, patient therapy adjustment data, and other data useful in producing posture state information. At the same time, IMD 14 or programmer 20 is able to provide highly useful information for a given therapy session, so that posture state data and therapy adjustment data for individual therapy sessions may be evaluated and compared to one another, e.g., to develop an efficacy trend.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes (not shown) that transfer the electrical stimulation from each of lead 16 to the tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
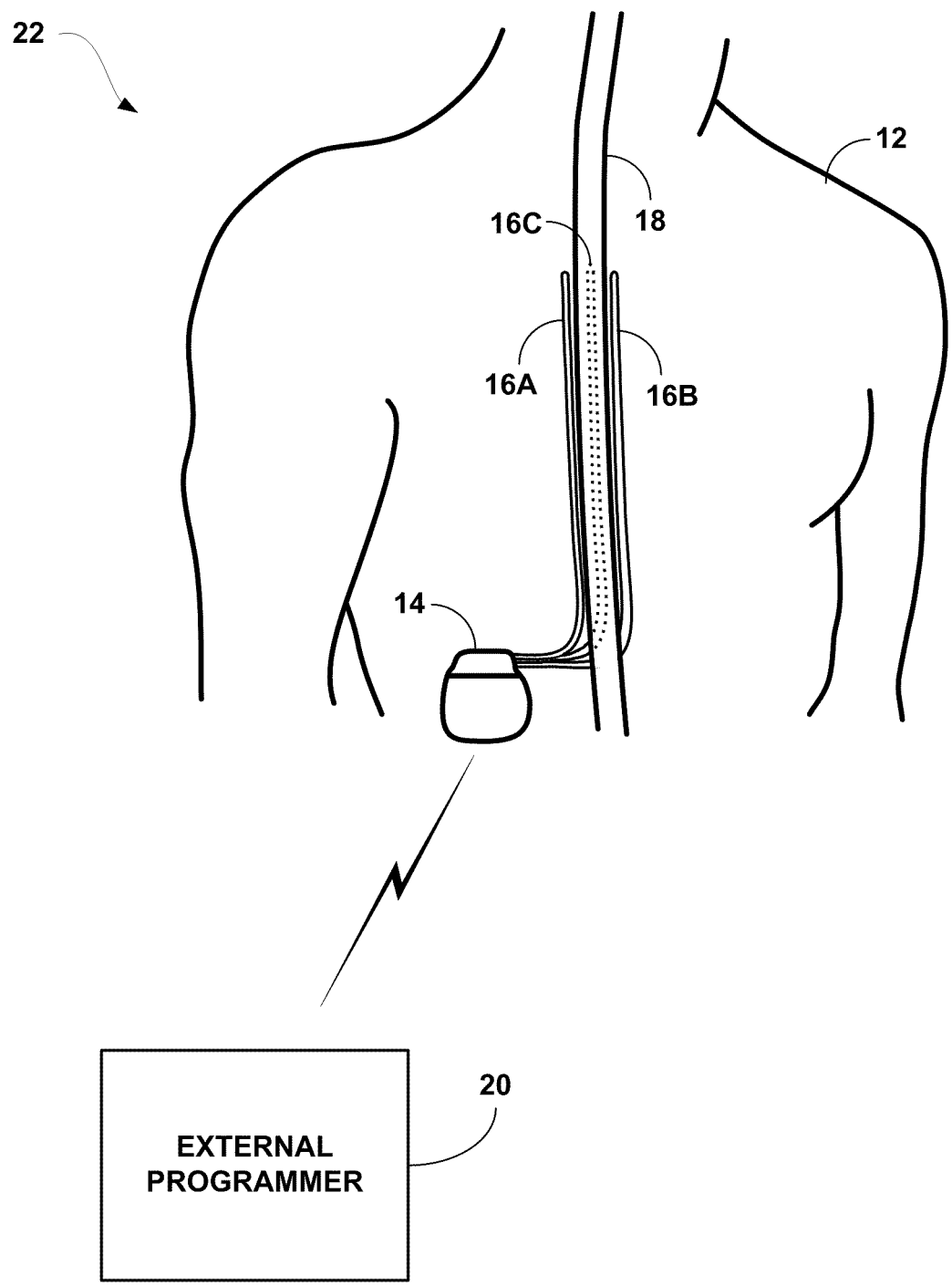
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16).

System 22 generally conforms to system 10 of FIG. 1A, but includes a third lead along spinal cord 18. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. External programmer 20 may be initially informed of the number and configuration of leads 16 in order to appropriately program stimulation therapy.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
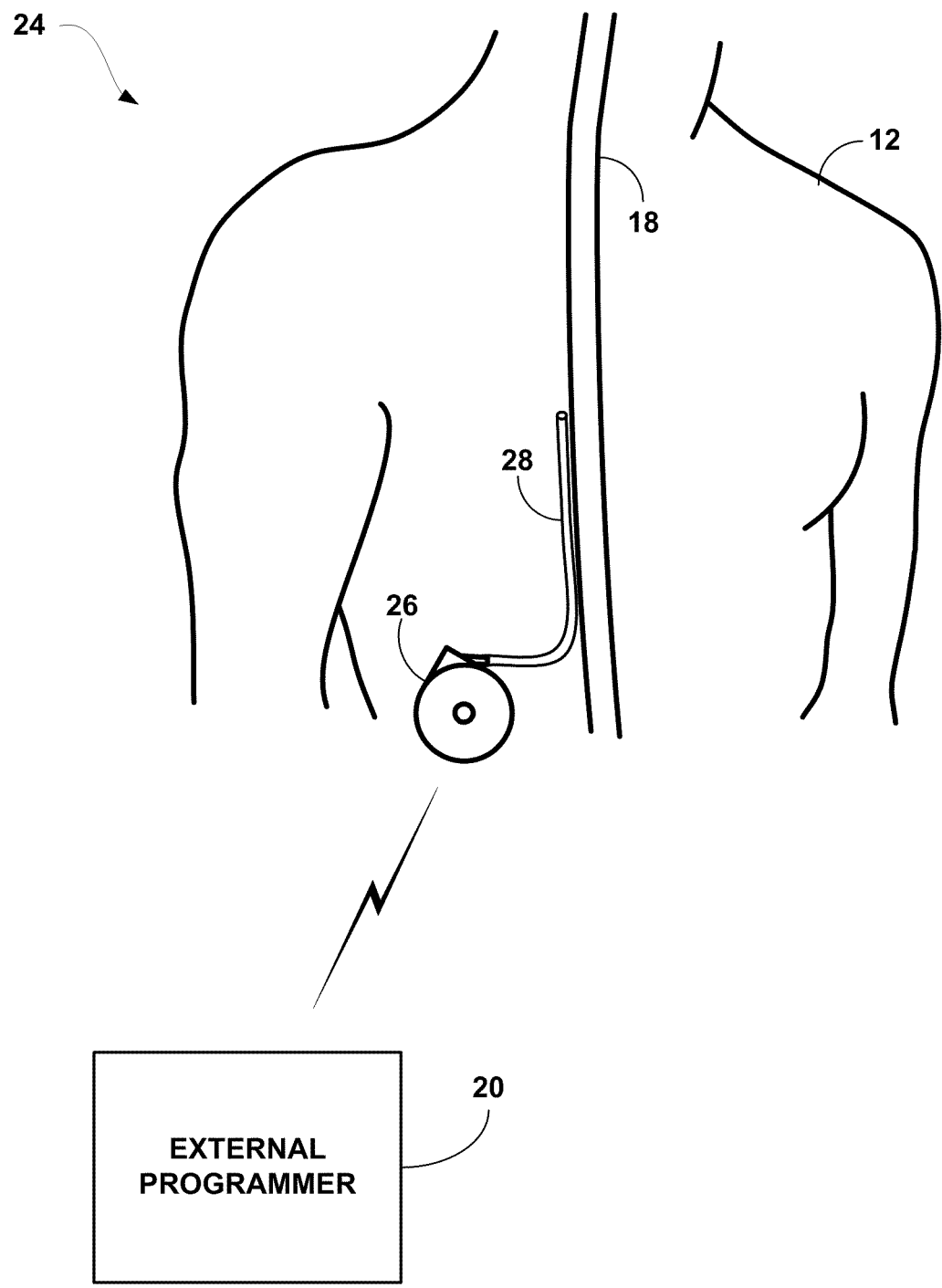
FIG. 1C is a conceptual diagram illustrating an implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of drug stimulation therapy instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some embodiments, IMD 26 may be an external device which includes a percutaneous catheter that forms catheter 28 or that is coupled to catheter 28, e.g., via a fluid coupler. In other embodiments, IMD 26 may include both electrical stimulation as described in IMD 14 and drug delivery therapy.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery.

Similar to IMD 14, IMD 26 may include a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
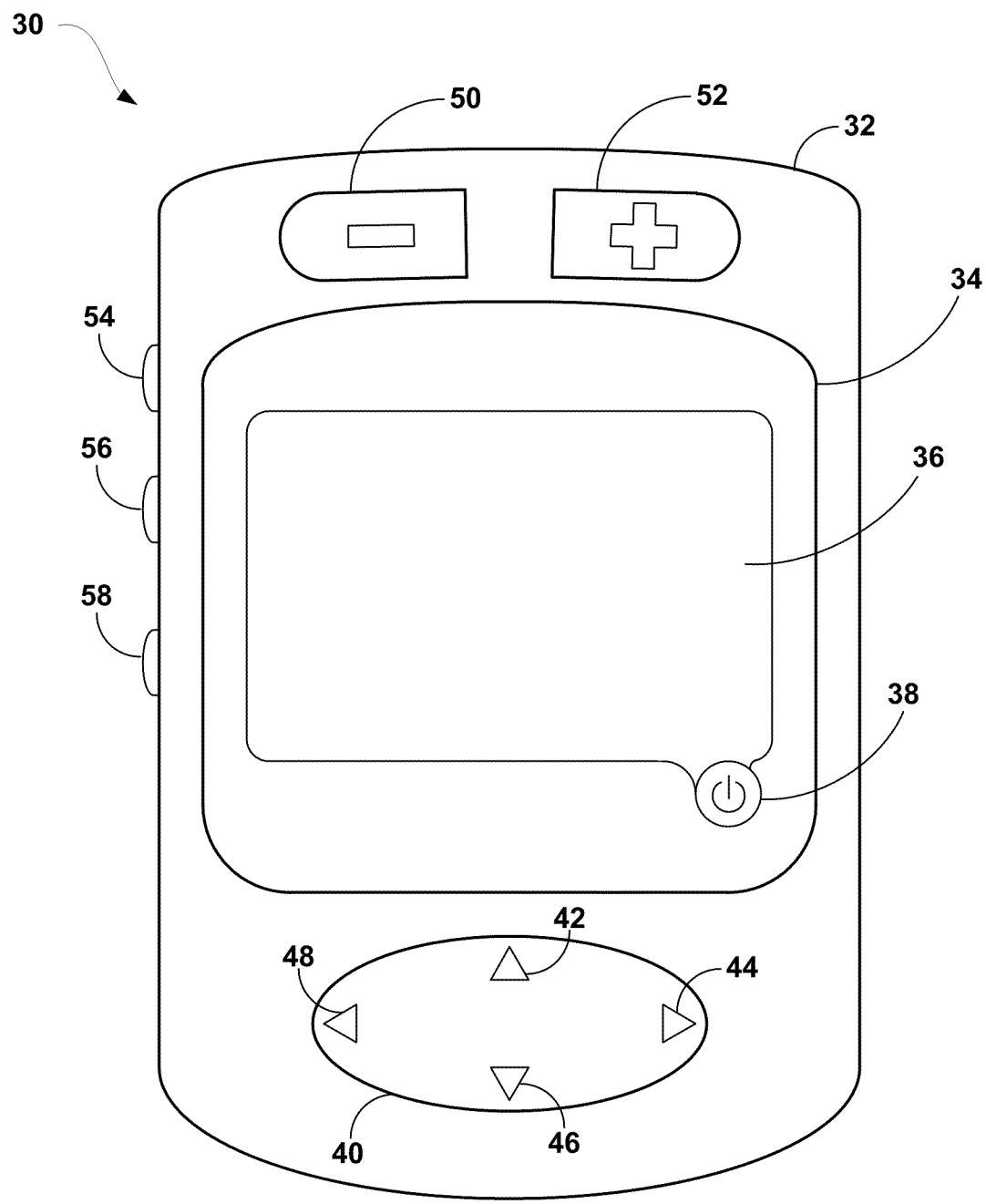
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an implantable medical device. Patient programmer 30 is an example embodiment of external programmer 20 illustrated in FIGS. 1A, 1B and 1C and may be used with either IMD 14 or IMD 26. In alternative embodiments, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some embodiments, the buttons and pad 40 may take the form of soft keys (e.g., with functions and contexts indicated on display 36), with functionality that may change, for example, based on current programming operation or user preference. In alternative embodiments, display 36 may be a touch screen in which patient 12 may interact directly with display 36 without the use of control pad 40 or even increase button 52 and decrease button 50.

In the illustrated embodiment, patient programmer 30 is a hand held device. Patient programmer 30 may accompany patient 12 throughout a daily routine. In some cases, patient programmer 30 may be used by a clinician when patient 12 visits the clinician in a hospital or clinic. In other embodiments, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52. In some embodiments, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may be a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication. Further, display 36 may present sleep quality information or proportional posture information that patient 12 may use to objectively determine therapy efficacy. The sleep quality information or proportional posture information may be presented graphically with shaded bars, colored features, graphical keys, three-dimensional graphs, embedded details, and any other elements beneficial to communicating the information to patient 12.

Control pad 40 allows patient 12 to navigate through items displayed on display 36. Patient 12 may press control pad 40 on any of arrows 42, 44, 46, and 48 in order to move to another item on display 36 or move to another screen not currently shown on the display. In some embodiments, pressing the middle of control pad 40 may select any item highlighted in display 36. In other embodiments, scroll bars, a scroll wheel, individual buttons, or a joystick may perform the complete or partial functions of control pad 40. In alternative embodiments, control pad 40 may be a touch pad that allows patient 12 to move a cursor within the user interface displayed on display 36 to manage therapy or review posture state information.

Decrease button 50 and increase button 52 provide an input mechanism for patient 12. In general, decrease button 50 may decrease the value of a highlighted stimulation parameter every time the decrease button is pressed. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either of buttons 50 and 52 is selected, patient programmer 30 may initiate communication with IMD 14 or 26 to change therapy accordingly.

When depressed by patient 12, stimulation ON button 54 directs programmer 30 to generate a command for communication to IMD 14 that turns on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some embodiments, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display 36 brightness and contrast, or other similar options. In alternative embodiments, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative embodiments of patient programmer 30 may include other input mechanisms such as a keypad, microphone, camera lens, or any other media input that allows the user to interact with the user interface provided by patient programmer 30.

In alternative embodiments, the buttons of patient programmer 30 may perform different functions than the functions provided in FIG. 2 as an example. In addition, other embodiments of patient programmer 30 may include different button layouts or different numbers of buttons. For example, patient programmer 30 may even include a single touch screen that incorporates all user interface functionality with a limited set of buttons or no other buttons.

Figure 3:
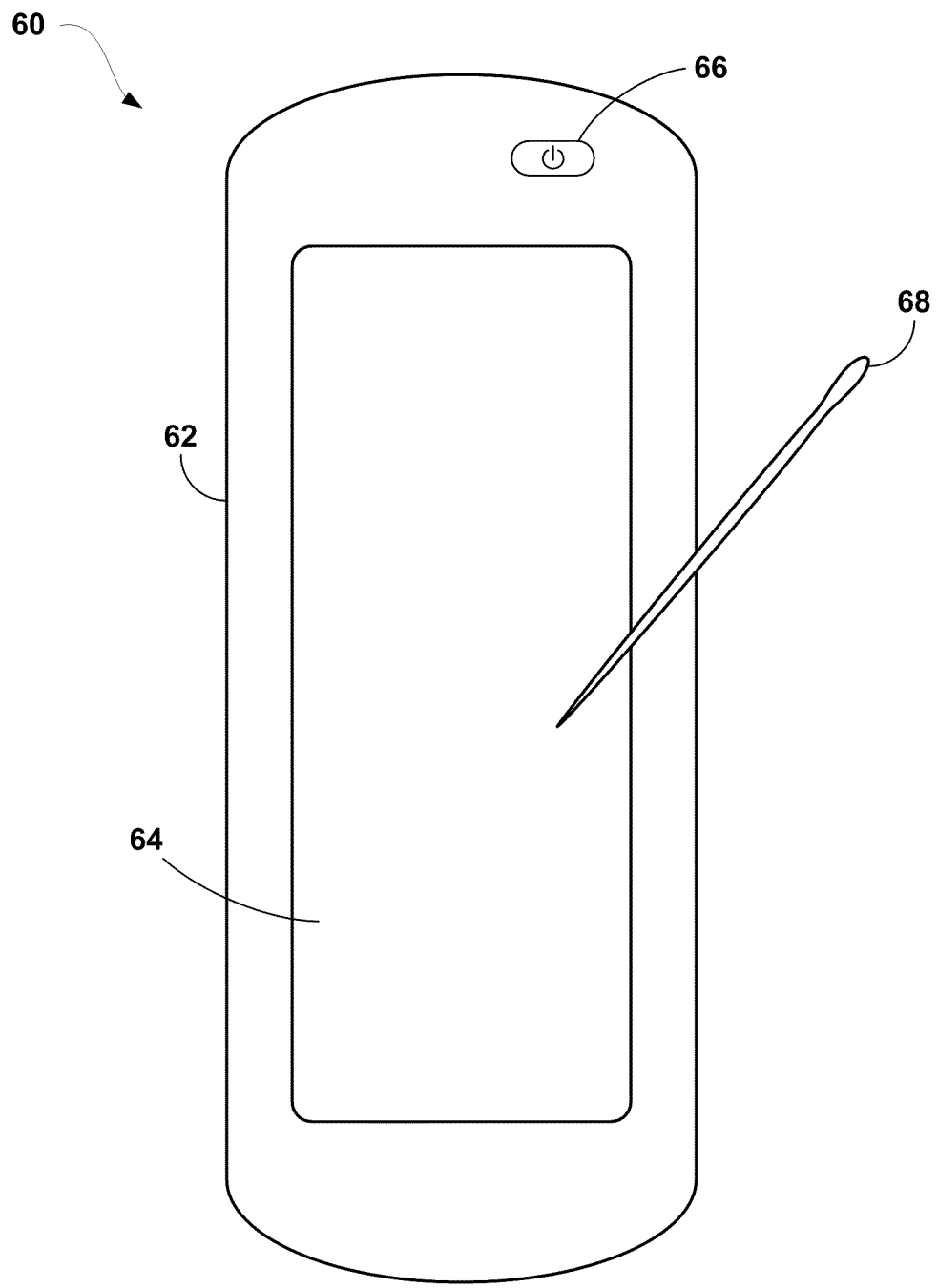
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an implantable medical device. Clinician programmer 60 is an example embodiment of external programmer 20 illustrated in FIGS. 1A, 1B and 1C and may be used with either IMD 14 or IMD 26. In alternative embodiments, clinician programmer 60 may be used with an external medical device. As shown in FIG. 3, clinician programmer 60 provides a user interface (not shown) for a user, such as a clinician, physician, technician, or nurse, to manage and program stimulation therapy. In addition, clinician programmer 60 may be used to review objective posture state information to monitor the progress and therapy efficacy of patient 12. Clinician programmer 60 is protected by housing 62, which encloses circuitry necessary for clinician programmer 60 to operate.

Clinician programmer 60 is used by the clinician or other user to modify and review therapy to patient 12. The clinician may define each therapy parameter value for each of the programs that define stimulation therapy. The therapy parameters, such as amplitude, may be defined specifically for each of the posture states that patient 12 will be engaged in during therapy. In addition, the clinician may use clinician programmer 60 to define each posture state of patient 12 by using the posture cones described herein or some other technique for associating posture state sensor output to the posture state of patient 12.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some embodiments, the user may be able to touch display 64 with a finger, pen, or any other pointing device. In alternative embodiments, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a different, possibly larger, device that may be less portable, such as a notebook computer, workstation, or event a remote computer that communicates with IMD 14 or 26 via a remote telemetry device.

If another device such as a computer is used for processing or presentation of programming or posture state information, it may communicate with a patient or clinician programmer or otherwise receive or exchange information with a patient or clinician programmer. For example, posture information obtained by an IMD and uploaded to a patient or clinician programmer may be processed by the patient or clinician programmer and transmitted to another device to process the information for presentation to a user. As an illustration, sleep quality information may be generated based on posture state information obtained by an IMD, e.g., by a patient or clinician programmer or another device that receives the posture state information obtained by the IMD.

Most, if not all, of clinician programmer 60 functions may be completed via the touch screen of display 64. The user may program stimulation therapy, modify programs or groups, retrieve stored therapy data, retrieve posture state information, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Clinician programmer 60 may also allow the clinician to objectively monitor posture states of patient 12. The posture and activity of patient 12 is stored in IMD 14 as posture state data and may be presented by clinician programmer 60 in the form of posture state information. The posture state information may be sleep quality information, proportional posture information, or other information that includes objective data related to the frequency and duration of the posture states occupied by patient 12. This information may be presented in an organized graphical and/or numerical manner for quick reference by the clinician.

For example, clinician programmer 60 may be configured to display shaded grayscale graphs of the percentage of time that patient 12 engaged in each of the posture states. In addition, clinician programmer 60 may be configured to display bar charts illustrating the actual or average number of posture state changes per day when patient 12 was lying down to indicate the sleep quality of patient 12. In some cases, the sleep quality information may indicate the number of transitions between each of the posture states, e.g., the number of each of the following posture state transitions: lying front to lying back, lying front to lying right, lying front to lying left, lying back to lying front, lying back to lying left, lying back to lying right, lying right to lying back, lying right to lying front, lying right to lying left, lying left to lying back, lying left to lying front, or lying left to lying back. Clinician programmer 60 may also be configured to allow the clinician to interact with the displayed graphs, charts, scatter plots, and other information by selecting a portion of the information to view details about that specific selected information. As an example, the clinician may select a bar illustrating the posture state proportions for a previous month to view the average posture duration in time for each posture state during that month.

Clinician programmer 60 may also allow the clinician to customize the way in which programmer 60 presents the sleep quality information and the proportional posture information. The clinician may view sleep quality information, proportional posture information, number of patient therapy adjustments, number of posture state transitions, or other information for multiple time intervals, e.g., multiple therapy sessions, simultaneously. The clinician may be able to select from several types of graphs or charts, select the number of time intervals for which information is displayed, or even create new graphs or charts to present only the information desired by the clinician. For example, patient 12 may have difficulty sleeping on their back due to chronic back pain. The clinician may configure clinician programmer 60 to only view lying back posture state information, such as the average posture duration each day and the average number of times patient 12 transitioned away from one or more lying back posture states for the past several months.

In some examples, clinician programmer 60 may not store any of the posture state data used to generate the sleep quality information and the proportional posture information. Each time that the clinician desires to view the objective information related to the posture states, clinician programmer 60 may need to acquire all or some of the posture state data from a memory of IMD 14. In other examples, clinician programmer 60 may store posture state data from IMD 14 each time that clinician programmer 60 communicates with IMD 14. In this manner, clinician programmer 60 may only need to acquire the posture state data stored in IMD 14 since the previous programming session, i.e., communication with IMD 14. The time interval between programming sessions may be considered a therapy session in which therapy was delivered according to programming performed in the previous programming session. Of course, clinician programmer 60 may not require all posture state data stored during therapy. In some embodiments, only the posture state data stored during desired time intervals, or relating to selected posture states, may be used to present the sleep quality information or the proportional posture information. In other embodiments, IMD 14 may simply transfer raw data to an external programmer 20 or other computing device for data processing necessary to perform the tasks described herein.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
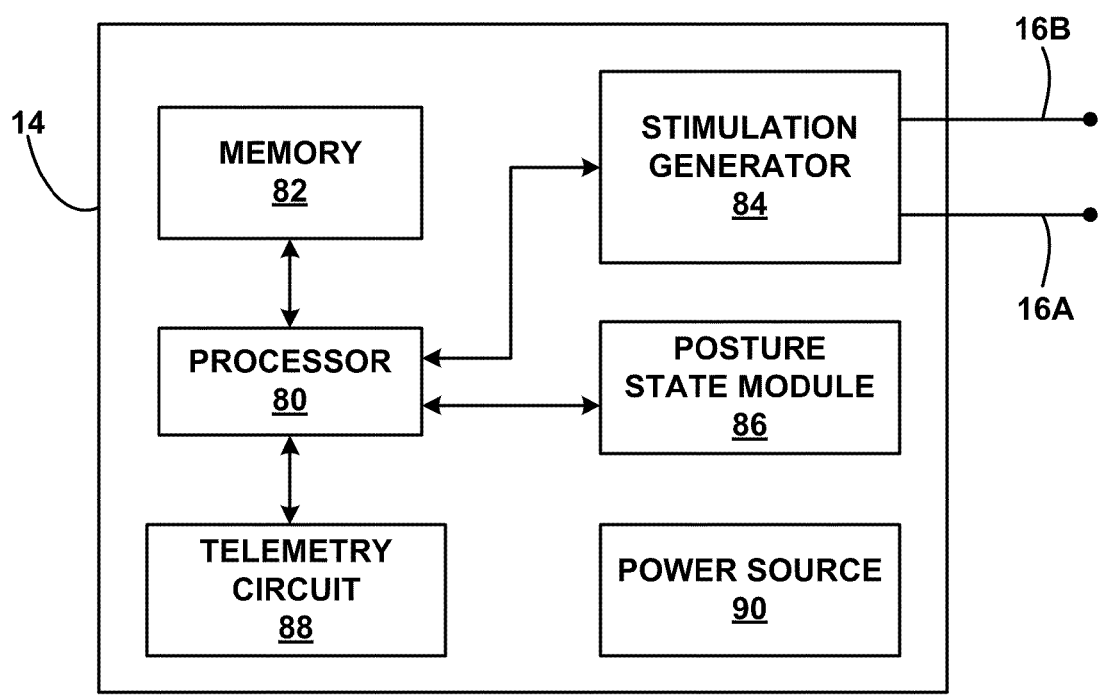
FIG. 4 is a functional block diagram illustrating various components of an implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. Memory 82 may store instructions for execution by processor 80, stimulation therapy data, posture state information, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other embodiments, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To change electrode configurations, amplitudes, pulse rates, or pulse widths, processor 80 may command stimulation generator 84 to make the appropriate changed to therapy according to instructions within memory 82 and rewrite the memory location to indicate the changed therapy. In other embodiments, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12. Processor 80 also may control telemetry circuit 88 to send and receive information to and from external programmer 20. For example, telemetry circuit 88 may send information to and receive information from patient programmer 30. An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

3. Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications.

Processor 80 stores stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads.

Posture state module 86 allows IMD 14 to sense the patient posture state, e.g., posture, activity or any other static position or motion of patient 12. In the example of FIG. 4, posture state module 86 may include one or more posture state sensors, e.g., one or more accelerometers such as three-axis accelerometers, capable of detecting static orientation or vectors in three-dimensions. The three-axis accelerometer may be a micro-electro-mechanical accelerometer. In other examples, posture state module 86 may alternatively or additionally include one or more gyroscopes, pressure transducers or other sensors to sense the posture state of patient 12. Posture state information generated by posture state module 86 and processor 80 may correspond to an activity, posture, or posture and activity undertaken by patient 12 or a gross level of physical activity, e.g., activity counts based on footfalls or the like.

Posture state information from posture state module 86 may be stored in memory 82 to be later reviewed by a clinician, used to adjust therapy, presented as a posture state indication to patient 12, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture defined within memory 82. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

As described herein, the posture state data, or raw data of the posture state information, is stored by system 10 to be used at a later time to generate sleep quality information and proportional posture information, which may be referred to generally as posture state output for a patient. Memory 82 may store all of the posture state data detected during therapy or use of IMD 14, or memory 82 may periodically offload the posture state data to clinician programmer 60 or a different external programmer 20 or device. In other examples, memory 82 may reserve a portion of the memory to store recent posture state data easily accessible to processor 80 for analysis. In addition, older posture state data may be compressed within memory 82 to require less memory storage until later needed by external programmer 20 or processor 80.

A posture state parameter value provided from posture state module 86 that indicates the posture state of patient 12 may constantly vary throughout the daily activities of patient 12. However, a certain activity (e.g., walking, running, or biking) or a posture (e.g., standing, sitting, or lying down) may include multiple posture state parameter values from posture state module 86. In this manner, a posture state may include a broad range of posture state parameter values. Memory 82 may include definitions for each posture state of patient 12. In one example, the definitions of each posture state may be illustrated as a cone in three-dimensional space. Whenever the posture state parameter value, e.g., a vector, from the three-axis accelerometer of posture state module 86 resides within a predefined cone, processor 80 indicates that patient 12 is in the posture state of the cone. In other examples, posture state parameter value from the 3-axis accelerometer may be compared to a look-up table or equation to determine the posture state in which patient 12 currently resides.

Posture responsive stimulation may allow IMD 14 to implement a certain level of automation in therapy adjustments. Automatically adjusting stimulation may free patient 12 from the constant task of manually adjusting therapy parameters each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. Alternatively, patient 12 may be unable to manually adjust the therapy if patient programmer 30 is unavailable or patient 12 is preoccupied. In some embodiments, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In some embodiments, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some embodiments, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion or activity. This activity may involve a level, direction of motion, or acceleration of the patient.

One method for determining the activity is an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

In other embodiments, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive of posture state.

Wireless telemetry in IMD 14 with external programmer 20, e.g., patient programmer 30 or clinician programmer 60, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Figure 5:
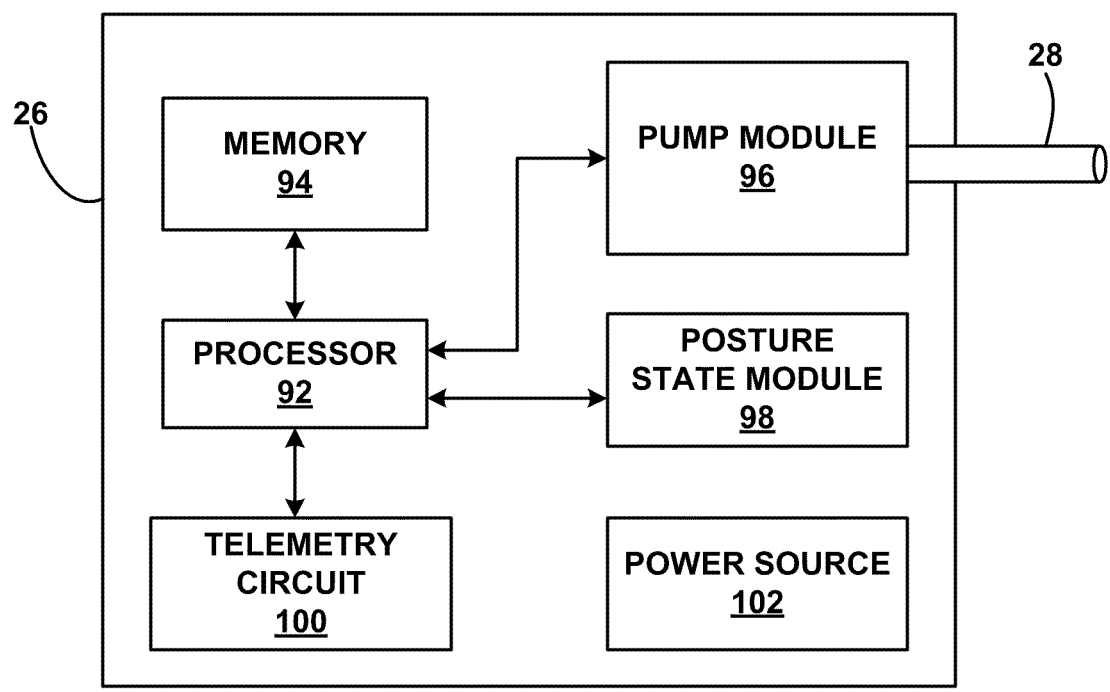
FIG. 5 is a functional block diagram illustrating various components of an implantable drug pump.

FIG. 5 is a functional block diagram illustrating various components of an IMD 26 that is a drug pump. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 may control pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his or her posture. In alternative embodiments, system 10 may be employed by an implantable medical device that delivers therapy via both electrical stimulation therapy and drug delivery therapy as a combination of IMD 14 and IMD 26.

Figure 6:
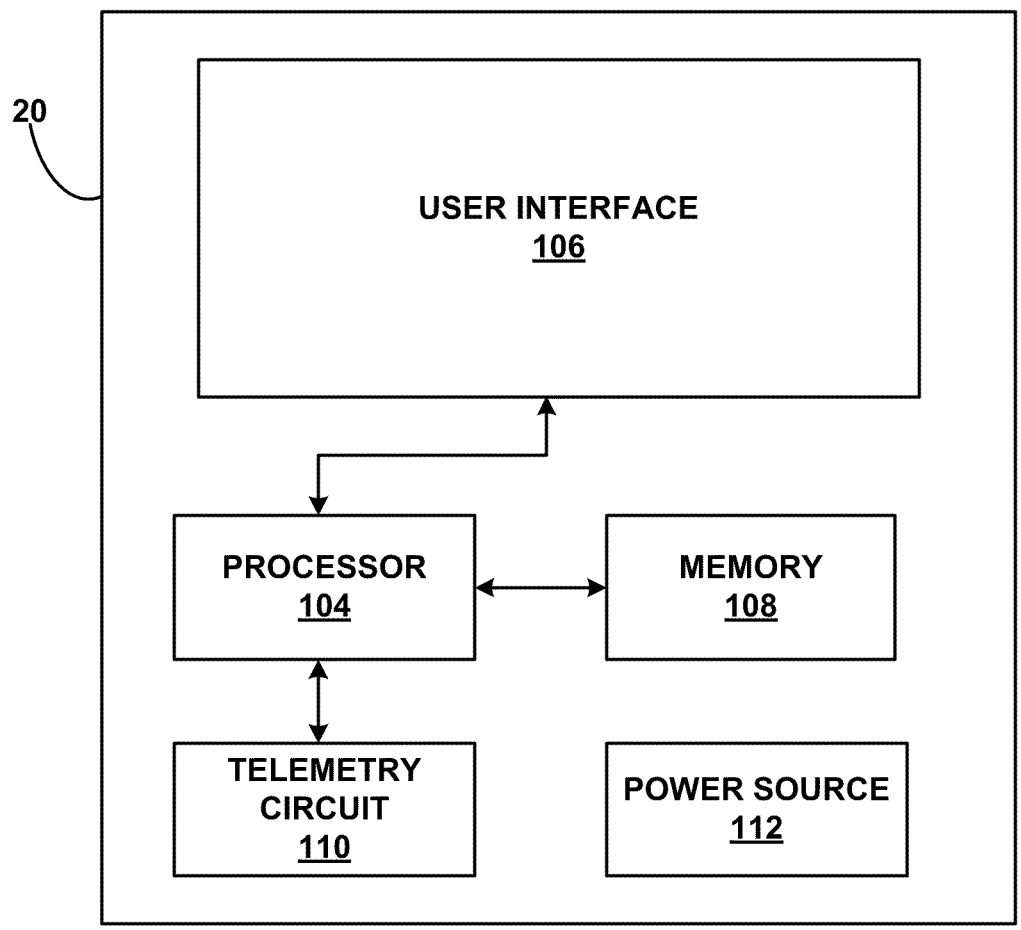
FIG. 6 is a functional block diagram illustrating various components of an external programmer for an implantable medical device.

FIG. 6 is a functional block diagram illustrating various components of an external programmer 20 for IMDs 14 or 26. As shown in FIG. 6, external programmer 20 includes processor 104, memory 108, telemetry circuit 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive stimulation ON or OFF, view therapy information, view posture state information, or otherwise communicate with IMDs 14 or 26.

User interface 106 may include a screen and one or more input buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

User interface 106 is configured to present sleep quality information and proportional posture information to the user. In addition to presenting text, user interface 106 may be configured to present graphical representations to the user in grayscale, color, and other visual formats. For example, user interface 106 may be configured to present the proportional posture information as a graphical posture duration graph that visually indicates the proportion of time patient 12 has been engaged in each posture state. User interface 106 may be able to reconfigure the displayed posture duration graph to show proportional posture information throughout different time intervals of the therapy, such as over days, weeks, months, or years. In particular, the proportional posture information can be shown for multiple time intervals simultaneously, permitting a clinician to observe a trend in the information. The time intervals may also be defined by the dates when the patient visited with a clinician for a clinic programming session or received program parameters via a remote programming session. In this manner, in some examples, the time interval may be referred to as an intersession time interval or a therapy session, i.e., a therapy session between programming sessions. The user may also interact with user interface 106 to present comparison posture duration graphs that indicate the difference in patient 12 posture during two or more specific time intervals. From this information, the user may be able to determine trends in the therapy and adjust the therapy parameters accordingly in order to achieve effective therapy.

The sleep quality information, proportional posture information, and other information related to the posture states, i.e., posture state information, may be stored within memory 108 or within another data storage device, such as a hard drive, flash memory or the like. External programmer 20 may store information obtained from previously interrogating IMD 14 so that that same information does not need to be retrieved from the IMD repeatedly, and so that IMD 14 may overwrite information, if necessary, in some implementations. Hence, external programmer 20 may retrieve new information from IMD 14, i.e., information that has been newly obtained since the previous interrogation, and also rely on archived information stored in the programmer or elsewhere. External programmer 20 may store the posture state information in memory 108 during communication sessions with IMD 14. The user may then have quick access to the posture state information without first communicating to IMD 14 and acquiring the posture state information from IMD 14 every time that the user desired to review the sleep quality information or proportional posture information, for example. If memory 108 does store posture state information from patient 12, memory 108 may use one or more hardware or software security measures to protect the identify of patient 12. For example, memory 108 may have separate physical memories for each patient or the user may be required to enter a password to access each patient's posture state data.

Telemetry circuit 110 allows the transfer of data to and from IMD14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. In this case, the programmer may be integrated with recharging components in a common device. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. The techniques described herein may be communicated between IMD 14 via any type of external device capable of communication with IMD 14.

Figure 7:
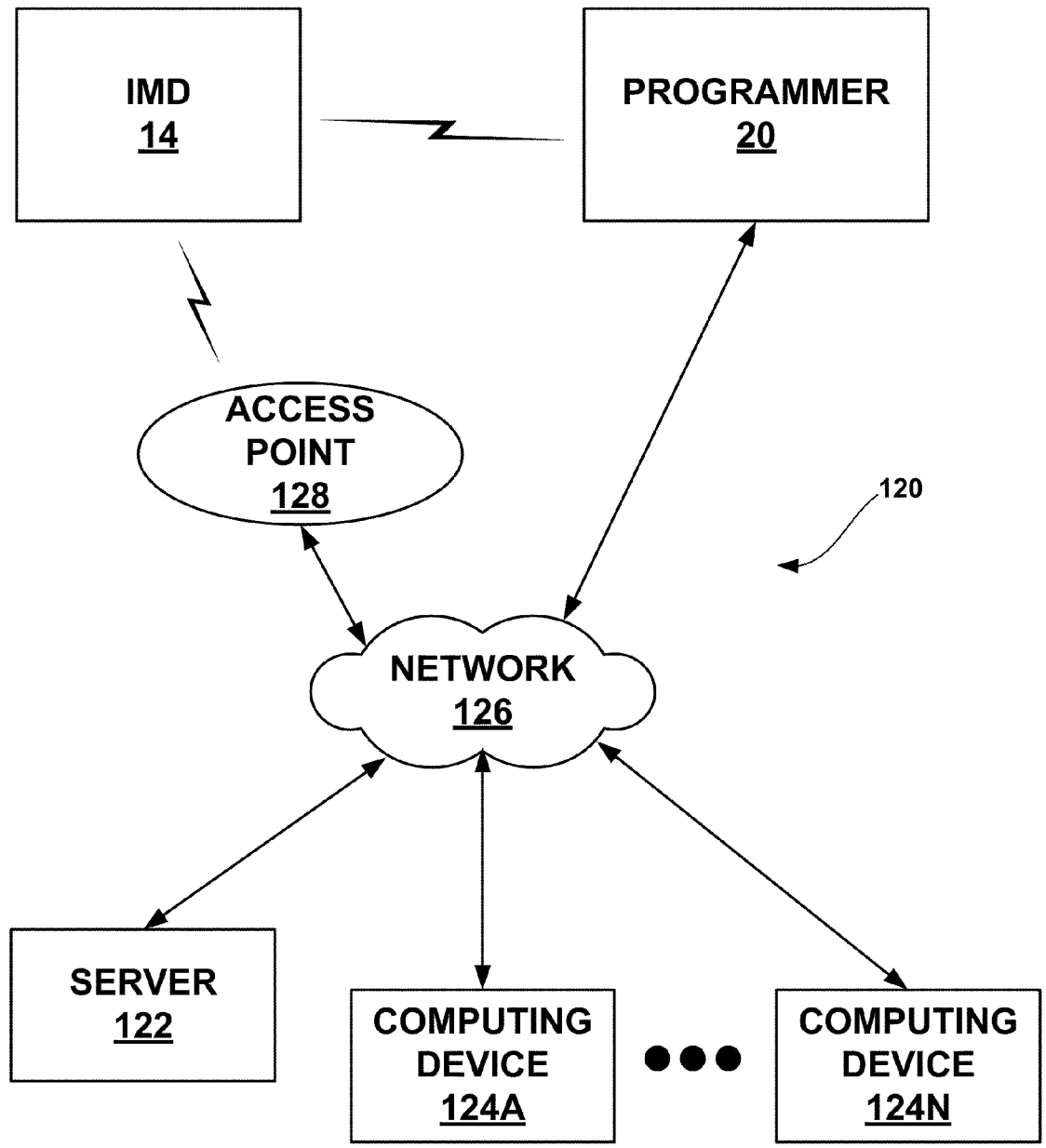
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the posture state of patient 12, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into posture state output such as a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of patient adjustments to therapy during each respective posture state, or any other information relevant to patient 12 therapy over one or more time intervals, such as one or more therapy sessions, based on analysis and evaluation performed automatically by IMD 14, external programmer 20 or server 122. A clinician or other trained professional may review and/or annotate the posture state report, and possibly identify any problems or issues with the therapy that should be addressed.

In the manner of FIG. 7, a clinician, physician, technician, or even patient 12, may review objectivity data with respect to the posture states of patient 12. The objectivity data may be sleep quality information or proportional posture information that indicates how patient 12 has been moving during the symptom diagnosis or delivered therapy, or posture transition information or patient therapy adjustment information that indicates the number of posture transitions and number of patient therapy adjustments for each posture state, respectively. The user may remotely monitor the progress and trends of patient 12 over the course of a therapy sessions or over multiple therapy sessions, limiting the number of times that patient 12 may need to physically visit the clinician. This monitoring may also reduce the time needed to find efficacious therapy parameters by allowing the clinician to more frequently monitor sleep quality information and proportional posture information. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
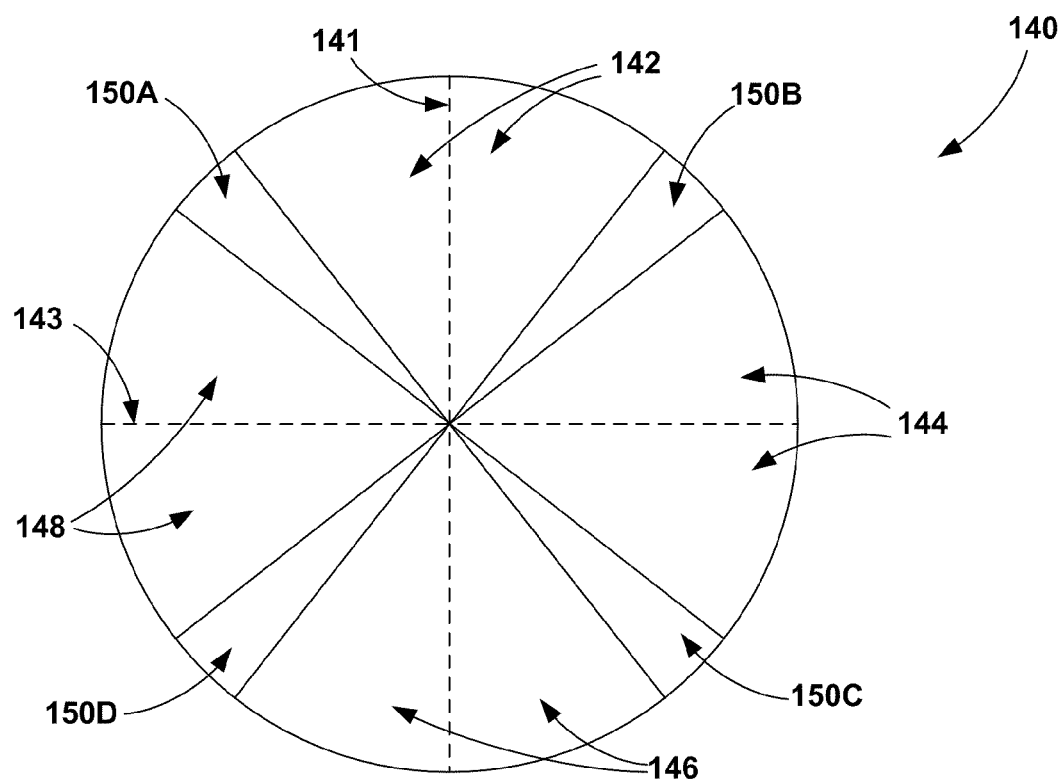
FIGS. 8A-8C are conceptual diagrams illustrating definition and detection of a posture state of a patient based on signals sensed by a posture state sensor.
Figure 8B:
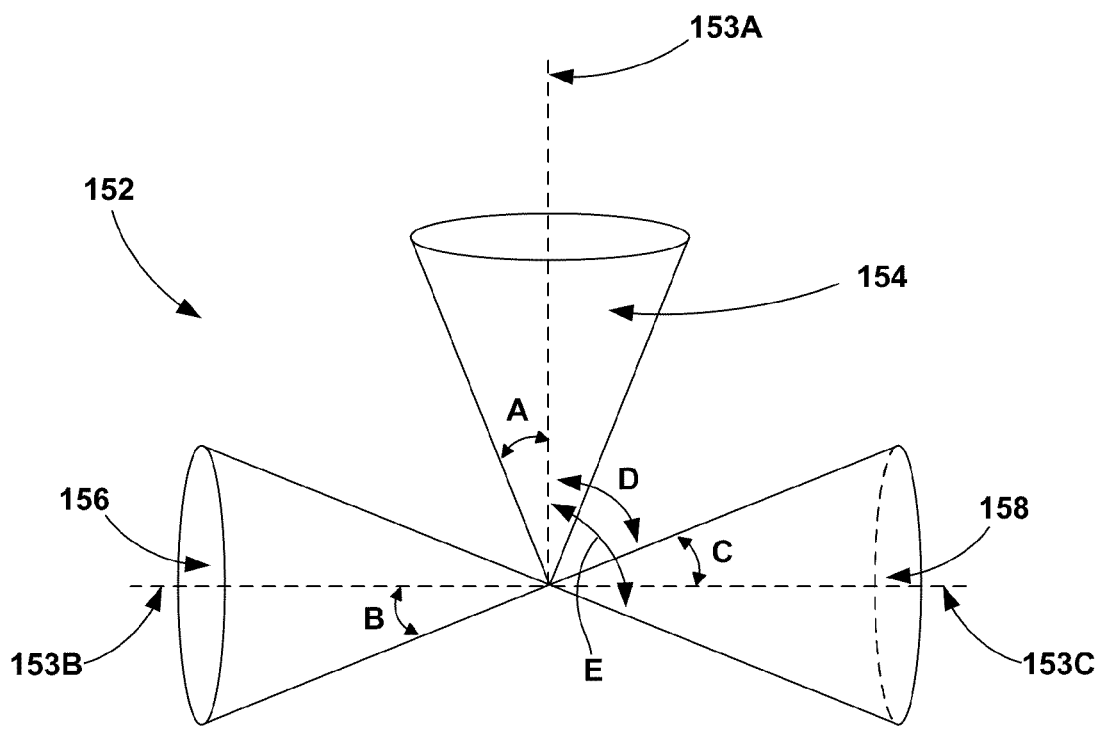
Figure 8C:
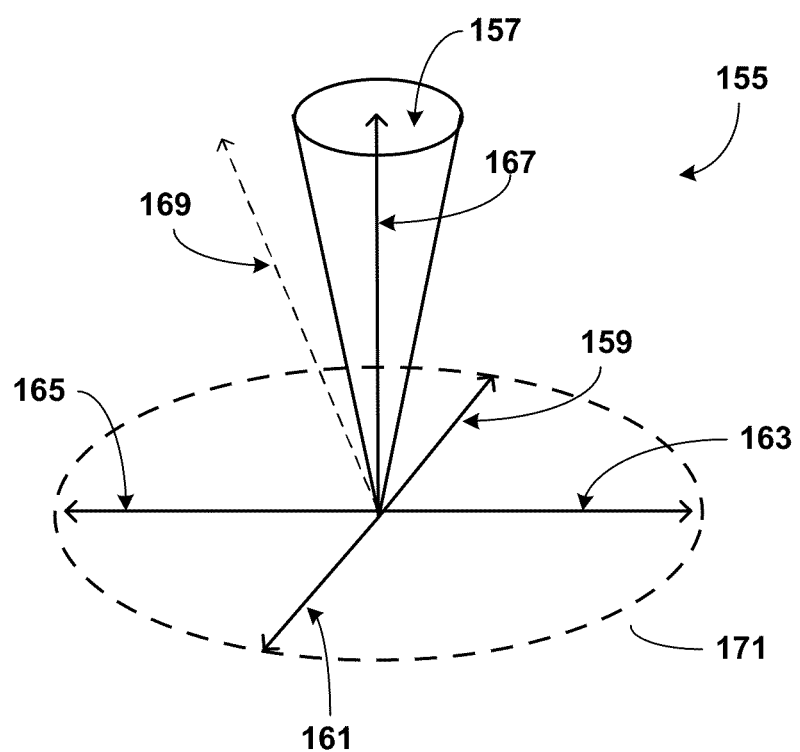

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone may be positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Moreover, the reference coordinate vectors need not reside in the same plane. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying up (back) and lying down (front) cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying down cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other, and need not even reside in the same plane. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another, and need not reside within the same plane.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
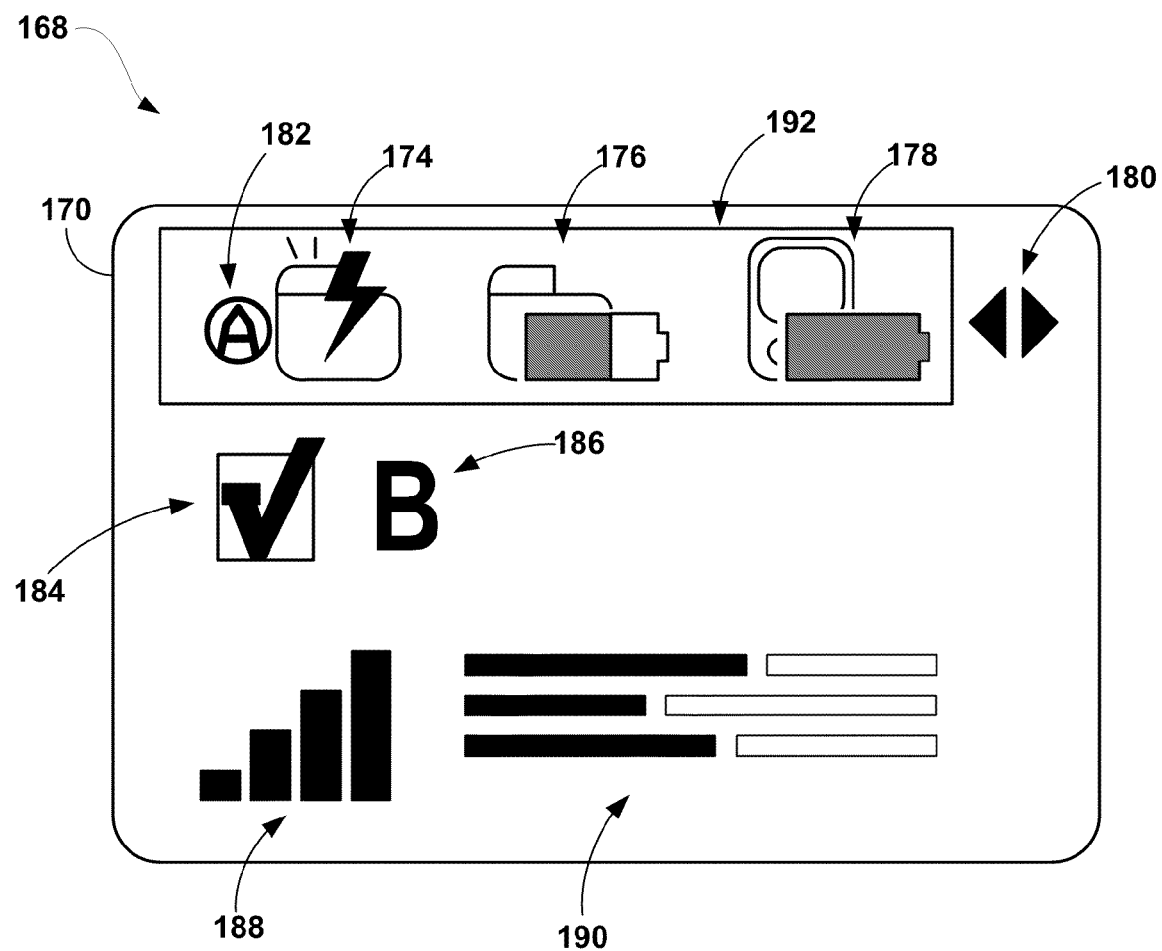
FIG. 9 is a conceptual diagram illustrating an example user interface of a patient programmer for delivering therapy information to the patient.

FIG. 9 is a conceptual diagram illustrating an example user interface 168 of a patient programmer 30 for delivering therapy information to patient 12. In other examples, a user interface similar to user interface 168 may also be shown on clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example, of screen 170, selection box 192 is positioned so that patient 12 may use arrows 44 and 48 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid (black) portions of the bars indicate the relative amplitude IMD 14 currently is using to deliver stimulation therapy to patient 12, while open (white) portions of the bars indicate the remaining amplitude available to each program. In some embodiments, numerical values of each program's amplitude may be shown in addition to or in place of amplitude graph 190. In other embodiments of user interface 168 specific to drug delivery using IMD 26, amplitude graph 190 may show the flow rate of drugs, frequency of bolus delivery to patient 12, or other parameter values. This information may be shown in numerical format as well. Patient 12 may encompass group selection icon 184 with selection box 192 to scroll between the different groups of programs.

Automatic posture response icon 182 indicates that IMD 14 is generally activated to automatically change therapy to patient 12 based upon the posture state detected by posture state module 86. In particularly, automatic posture responsive therapy may involve adjusting one or more therapy parameter values, selecting different programs or selecting different program groups based on the detected posture state of the patient. However, automatic posture response icon 182 is not present next to group identifier 186. Therefore, group "B" does not have automatic posture responsive therapy activated for any of the programs within group "B."

Some groups or individual programs in groups may support automatic posture responsive therapy. For example, automatic adjustment of one or more therapy parameters in response to posture state indication may be selectively activated or deactivated based on settings entered by a clinician, or possibly patient 12. Hence, some programs or groups may be configured for use with posture responsive therapy while other programs or groups may not be configured for use with posture responsive therapy. In some cases, if posture responsive therapy supported by the automatic posture response feature is desired, patient 12 may need to switch therapy to a different group that has automatic posture responsive therapy activated for IMD 14 to adjust therapy according to the patient 12 posture state.

Figure 10:
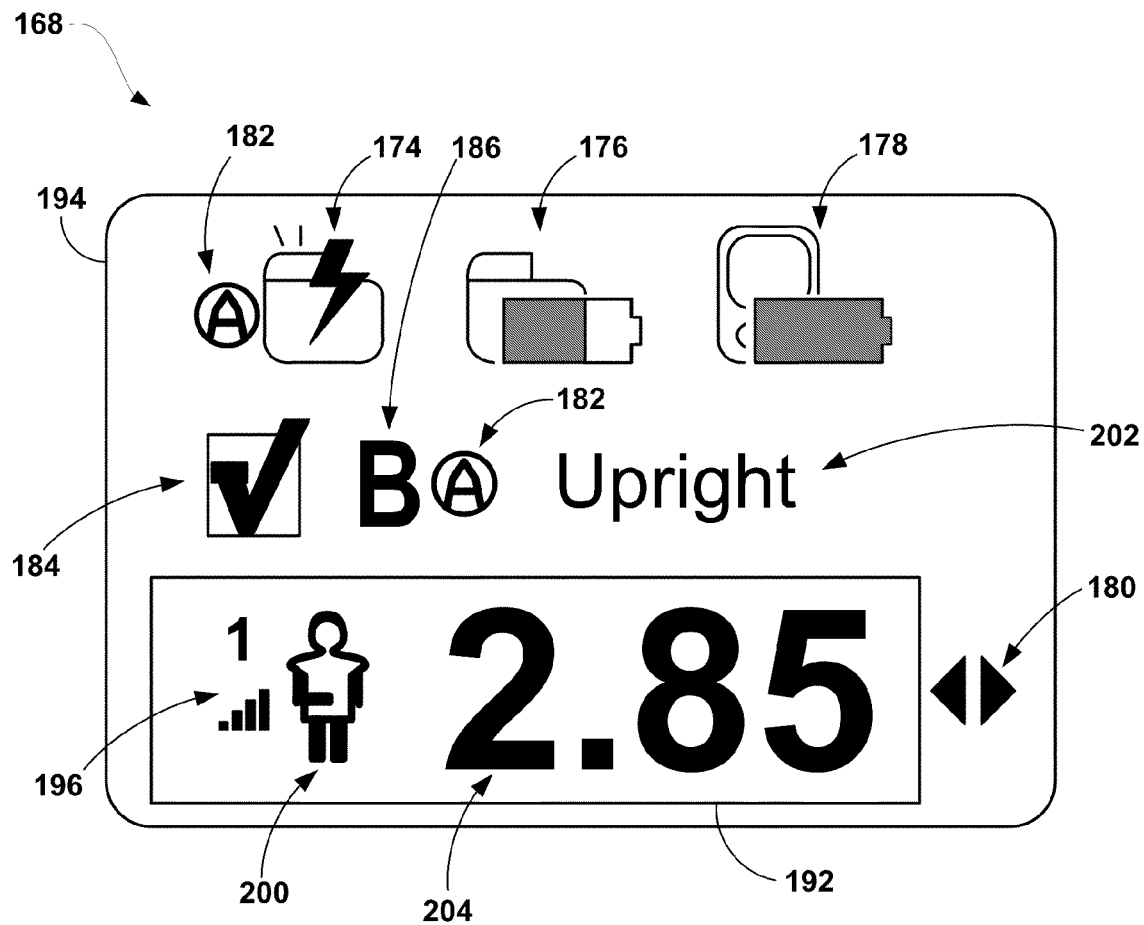
FIG. 10 is a conceptual diagram illustrating an example user interface of a patient programmer for delivering therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or patient 12.

Group identifier 186 indicates that group "B" is active, and automatic posture response icon 182 indicates group "B" (containing one or more programs) is activated to allow IMD 14 to automatically adjust therapy according to the patient posture state. Program identifier 196 illustrates the information regarding program "1" of group "B" is displayed on screen 194, such as amplitude value 204 illustrating the current voltage amplitude of program "1" as 2.85 Volts. Patient 12 may scroll through different programs of the group by using navigation arrows 180 via arrows 44 and 48 of control pad 40.

In addition, posture state indication 200 shows that IMD 14 has detected that patient 12 is in the upright or standing posture. Supplementary posture state indication 202 supplements posture state indication 200 by illustrating in one or more words to patient 12 the exact posture being detected by posture state module 86 of IMD 14 at a given time. Posture state indication 200 and supplementary posture state indication 202 change according to the sensed, or detected, posture state detected by IMD 14. The posture state may be communicated to external programmer 20 immediately when IMD 14 detects a posture change, or communicated periodically or non-periodically by IMD 14 unilaterally or upon receiving a request from programmer 20. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 views other programs within group "B" using selection arrows 208. Selection box 192 may be moved to select other screen levels with control pad 40 in order to navigate through other stimulation groups or adjustable elements of the therapy. When patient 12 selects a different program with control pad 40, program identifier 196 will change number to correctly identify the current program viewed on screen 194. In a different screen (not shown) of user interface 168, patient 12 may be allowed to view certain objectivity data, such as sleep quality information or proportional posture information available to the clinician as described herein. The clinician may enable to disable this feature depending upon whether patient 12 would benefit from being able to view this objective posture state information.

In addition to graphical, textual or other visible indications of posture state, external programmer 20 may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, different numbers of vibratory pulses delivered in sequence or vibratory pulses of different lengths, amplitudes, or frequencies.

Figure 11:
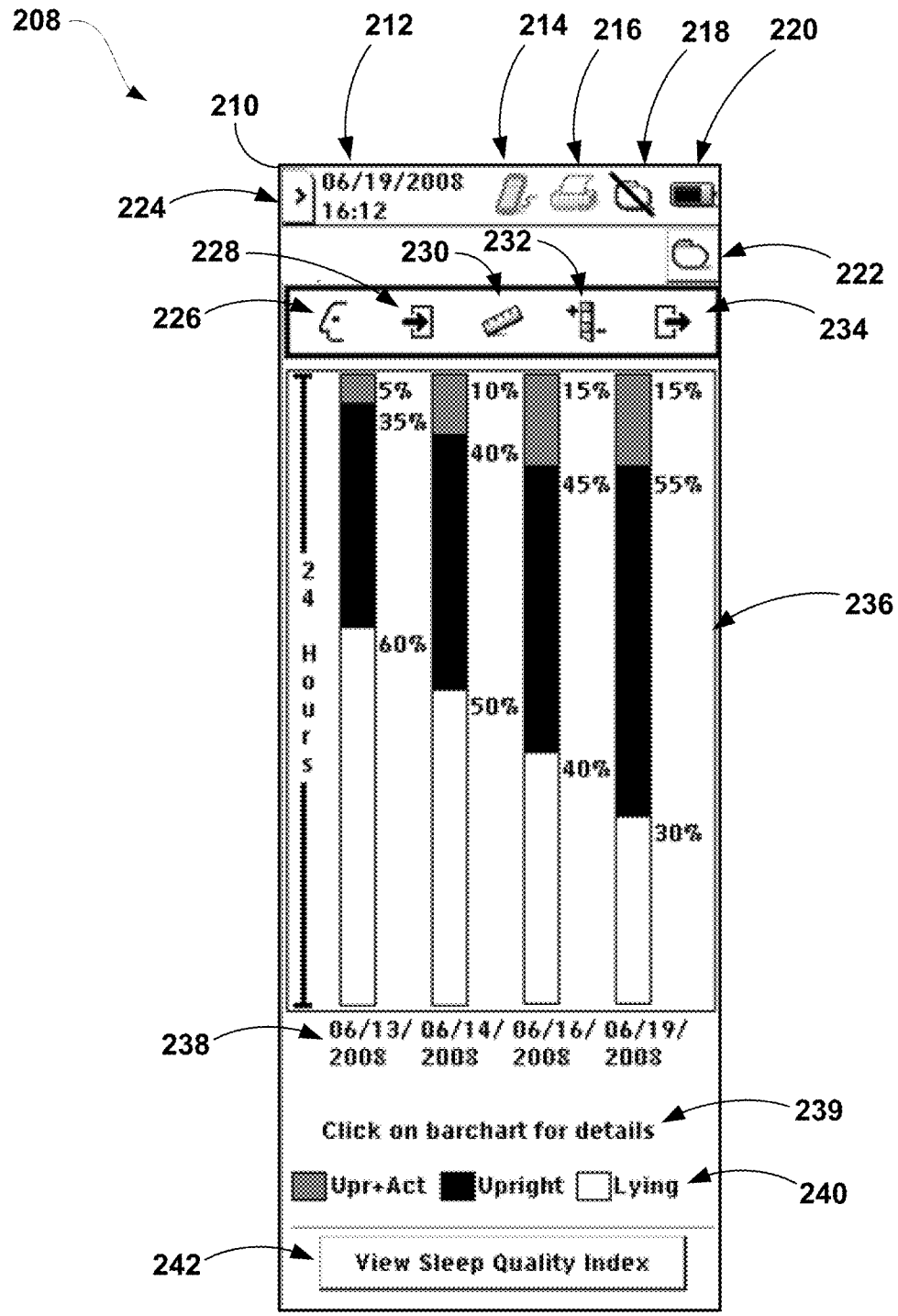
FIG. 11 is a conceptual diagram illustrating an example user interface for presenting graphical proportional posture information to a user for different time intervals, such as days.

FIG. 11 is a conceptual diagram illustrating an example user interface 208 for presenting graphical proportional posture information to a user for each of several days of a therapy session. User interface 208 is described as generally being displayed by clinician programmer 60. However, user interface 208 may also be displayed by patient programmer 30 or some other external programmer 20 or remote device. In any case, user interface 208 displays objective data derived from posture state data detected by a posture state module 86 based upon the posture and activity of patient 12. The posture state module 86 may reside within an IMD that delivers therapy to the patient, or within another device that is implanted within or external to a patient.

In the example of FIG. 11, screen 210 of user interface 208 presents posture duration graph 236, operational menu 224, networking icon 214, printer icon 216, IMD communication icon 218, programmer battery icon 220, stimulation status icon 222, patient data icon 226, data recording icon 228, device status icon 230, programming icon 232, and data reporting icon 234. In addition, screen 210 includes time intervals 238, detail input note 239, posture state key 240, and sleep quality button 242. Screen 210 may be accessed by selecting data recording icon 228 to open a drop down menu that allows the user to select one of multiple different screens. The user may select "objectification" or some other text or icon that symbolizes access to proportional posture information and screen 210.

Screen 210 includes multiple menus and icons common to other screens of user interface 208. Operational menu 224 is a button that the user may select to view multiple options or preferences selectable by the user. Operational menu 224 may provide preferences for clinician programmer 60 instead of therapy specific information. Networking icon 214 is shown as grayed out to indicate that clinical programmer 60 is not currently connected to a network. When networking icon 214 is shown fully, clinician programmer 60 is connected to a network. Printer icon 216 indicates when clinician programmer 60 is connected to a printer.

When printer icon 216 is grayed out as shown in FIG. 11, there is no printer connected to clinician programmer 60.

Further, IMD communication icon 218 is shown as indicating that clinician programmer is not in communication with IMD 14 because the icon includes a slash through the IMD representation. The slash is removed when clinician programmer 60 has established a communication link to IMD 14. In addition, programmer battery icon 220 indicates the current charge level of the battery contained within clinician programmer 60. Stimulation status icon 222 indicates to the user when stimulation is being delivered to patient 12. In the example of FIG. 11, stimulation is not currently being delivered, but stimulation status icon 222 may include an electrical bolt through the IMD representation when stimulation is being delivered by IMD 14.

Screen 210 also provides menu options related to stimulation therapy of patient 12. Patient data icon 226 allows the user to enter and review data related to the status of and the condition of patient 12. Data recording icon 228 allows the user to navigate to other screens to enter data recording preferences and review stored data. Device status icon 230 allows the user to view operational status of components of IMD 14, such as electrodes, leads, batteries, and any discovered problems. Programming icon 232 allows the user to navigate to programming screens that define the stimulation therapy parameters used to deliver stimulation to patient 12. In addition, data reporting icon 234 allows the user to view and print reports of patient 12 progress and other therapy information.

Posture duration graph 236 includes proportional posture information based on posture state data stored from detected posture states of patient 12. The proportional posture information may be generated based on durations for which the patient occupied each of a plurality of posture states based on the posture state data in a given time interval. In particular, the proportional posture information may be based on the durations indicating proportional amounts of the time interval in which the patient occupied each of the posture states. The proportional posture information may be presented in a graphical form, such as a bar graph. The graph may include posture bars for a plurality of time intervals. Each posture bar includes bar segments indicating proportional amounts of the respective time interval in which the patient occupied each of the posture states.

Posture duration graph 236 includes the percentage of time, or posture durations, for each of two or more posture states during given time intervals. In the example of FIG. 11, posture duration graph 236 indicates that percentage of time during which the patient occupied each of three posture states during each of the indicated days defined by time intervals 238. In particular, each bar in the bar graph corresponds to one of the time intervals, and each bar includes multiple bar segments, where each segment indicates the proportional amount of time the patient occupied a particular posture state in relation to the overall amount of time of the respective one of time intervals 238. Time intervals 238 may be days, weeks, months, years, durations between two clinician programming sessions, or some other period of time. In the example of FIG. 11, each time interval is a particular day. Each of time intervals 238 may also be of varying time durations. Posture duration graph 236 is generally described as indicating respective percentages of time in which patient 12 resides in a given posture state during a time interval. Percentages, absolute times, or other metrics may be used and obtained in variety of ways.

For example, a posture detection module, e.g., posture state module 86, may sample the posture state at regular sampling intervals, and then determine the percentage of time in which patient 12 occupied particular posture state by adding up the number of samples associated with that posture state versus the total number of samples obtained during the time interval. In this case, if Y posture state samples are taken within an interval, a posture state that is detected X times may be expressed in terms of a percentage X/Y.

As an alternative example, samples may be time-stamped or tracked in a timer or counter such that the elapsed time between a sample indicating a transition to a particular posture state and a sample indicating a transition away from the particular posture state can be computed, indicating a duration that the patient resided in the posture state. In this case, total elapsed time can be calculated over the time interval, taking into account multiple transitions to and from the posture state, if applicable. Alternatively, instead of using time stamps, a timer or counter may be activated when the patient 12 transitions to a posture state and deactivated when the patient transitions away from the posture state.

As a further example, the number of samples for a given posture state may be multiplied by a known amount of time between consecutive samples in order to compute an overall time in the posture state. If there are "n" samples for a given posture, and a time of "m" seconds separates consecutive samples, then the total time in the posture may be determined to be "n" multiplied by "m" seconds.

In addition to overall time during a time interval, individual durations within a posture, i.e., after transitioning to and before transitioning away from the posture, may be tracked using techniques similar to those described above. Many different techniques may be used to calculate the percentages of time in which a patient 12 resides in different posture states over a given time interval. Such techniques may be implemented within IMD 14, external programmer 20, or a combination of both. Accordingly, the examples described above are provided for purposes of illustration and without limitation of the techniques broadly described in this disclosure.

Posture state key 240 defines each of the posture segments (i.e., Upright and Active, Upright, Lying Down) that make up the posture bar for each time interval 238. A greater or lesser number of posture states may be tracked and expressed in graph 236. In addition, in some embodiments, a user may request refinement of some data. For example, a user may wish to know, among the lying down posture states, the percentage of time in which the patient occupied the lying down back, lying down front, lying right and lying left posture states. As an illustration, the programmer may permit the user to click on the lying portion of the graph, e.g., with a stylus, in order to view the percentages for the lying down sub-states. In response, external programmer 20 may display this additional information.

As shown in FIG. 11, the percentage of time that patient 12 spent in each posture state changed between each day, as indicated by the displayed proportional posture information. Time intervals 238 may be consecutive days. Alternatively, as shown in FIG. 11, some of time intervals 238 may be non-consecutive days, or other time intervals, such as weeks, months, or therapy sessions of varying length. The days used as time intervals 238 may have been selected by the clinician or automatically selected by processor 104 based upon the proportional posture information or the amount of time stimulation therapy was being delivered. For example, processor 104 may not present proportional posture information for time intervals in which stimulation was delivered for less than ten percent of the time interval, as such information may be less meaningful for purposes of evaluating therapeutic efficacy. In other cases, however, such information may provide a helpful set of baseline control data, e.g., for comparison with information obtained when stimulation is delivered for greater than ten percent of a time interval.

As shown on posture duration graph 236, for Jun. 13, 2008 ("06/13/2008"), proportional posture graph 236 indicates that patient 12 was in the lying down posture 60 percent of the time, the upright posture 35 percent of the time, and the upright and active posture state only 5 percent of the time. As mentioned above, the lying down posture state may include: lying front, lying back, lying right, and lying left. The upright and active posture state indicates that patient 12 was upright in addition to being engaged in some sort of activity, such as walking or running, as opposed to remaining stationary. In contrast, posture duration graph 236 shows that, for Jun. 19, 2008, six days later, patient 12 was in the lying down posture 30 percent of the time, the upright position 55 percent of the time, and the upright and active posture 15 percent of the time. The clinician may recognize a trend indicating that patient 12 is in the upright posture state for a much greater duration than when compared to the previous days. In some cases, the clinician may infer from such data that patient 12 may be responding well to effective therapy by being able to be up and out of bed for a greater percentage of the time.

Instead of or in addition to percentages, posture duration graph 236 may provide times in hours and minutes for each posture state. In addition, the lying down posture state may be split into two or more of all lying down postures, such as lying front, lying back, lying right, and lying left, either in a normal mode or upon receipt of user input requesting refinement of the lying down posture data, as mentioned above. Further, posture duration graph 236 may be altered by the clinician to show less than all of the posture states in order to more easily compare fewer posture states over time durations 238. Posture duration graph 236 may also be modified to include more or less than four time intervals at one time.

The objectivity of posture duration graph and proportional posture information may allow the clinician to monitor trends in the response of patient 12 to therapy, such as posture state-responsive therapy, without burdening patient 12 with the need to manually and, more subjectively, log their postures and activities throughout the day. In addition to the subjective nature of input by patient 12, entry of information by patient 12 is commonly plagued with errors, intentional or accidental, that can limit the clinician's access to accurate information for use in more effectively treating patient 12. Posture state data, including activity data, may be difficult for patient 12 to accurately determine. Logging posture state data may be especially difficult, or even impossible, during sleep. Therefore, generating proportional posture information and presenting the information to the clinician via user interface 208 may be beneficial. In particular, user interface 208 may present the proportional posture information for multiple time intervals simultaneously so that the clinician may observe a trend in posture states occupied by the patient over the multiple time intervals. The ability to observe proportional posture information for multiple time intervals to develop a trend may be especially useful when the clinician adjusts therapy parameters for different time intervals. Moreover, the clinician may select sleep quality button 242 in order to view specific sleep quality information generated from the posture state data, as described in FIGS. 17-20. In other words, the clinician may view general posture state information or selectively view specific posture state information, such as lying posture states, to evaluate sleep quality.

After the clinician views posture duration graph 236, the clinician may desire to view the detailed durations of each posture state used to create the posture duration graph. Detail input note 239 informs the clinician to "Click on BarChart for details." As mentioned above, detail input note 239 or another similar input medium may permit the user to refine the information, e.g., to view lying states in more detail and/or view sleep quality information, which also may include the lying states. If the clinician clicks or selects a location anywhere within posture duration graph 236, processor 104 may present the calculated posture state durations for each of the time intervals. In other examples, screen 210 may provide a customize icon that the clinician may select to modify how user interface presents the proportional posture information on posture duration graph 236.

In general, according to the example of FIG. 11, a programmer 20 or IMD 14 may obtain posture state data sensed by the IMD for a patient during delivery of therapy by the medical device, and determining durations for which the patient occupied each of a plurality of posture states based on the posture state data. Based on the durations, the programmer 20 or IMD 14 may proportional posture information for a plurality of different time intervals. The proportional posture information for each of the time intervals indicates proportional amounts of the respective time interval in which the patient occupied the posture states. As shown in FIG. 11, the proportional posture information for each of the time intervals may be presented to a user via a user interface of a programmer.

Figure 12:
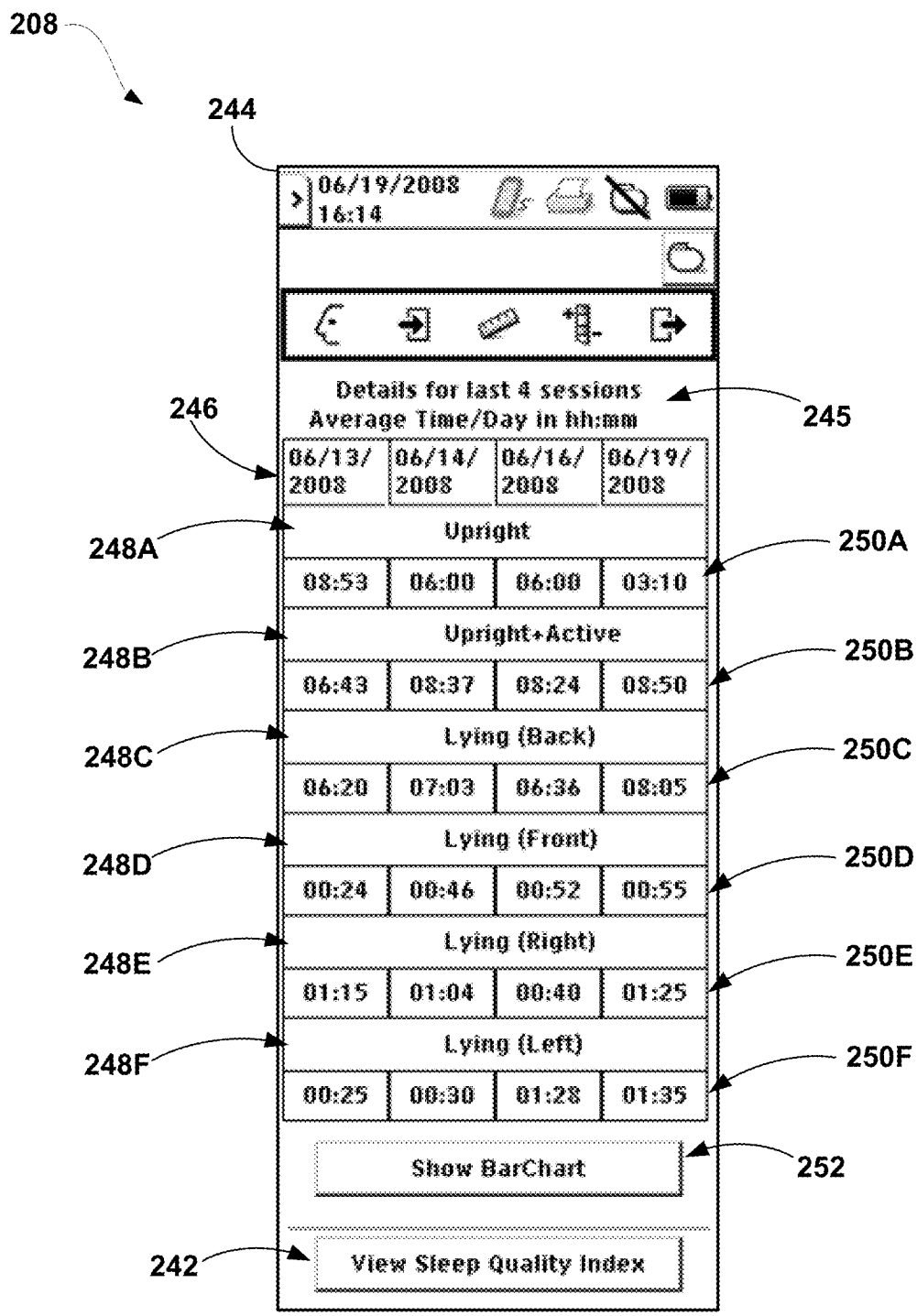
FIG. 12 is a conceptual diagram illustrating an example user interface for presenting detailed posture state durations for each time interval of FIG. 11.

FIG. 12 is a conceptual diagram illustrating an example user interface 208 for simultaneously presenting detailed posture state durations for each time interval of FIG. 11. Screen 244 of user interface 208 presents the calculated posture state durations for each of the posture states within each of the time intervals. Screen 244 also presents heading 245, time intervals 246, posture states 248A, 248B, 248C, 248D, 248E and 248F (collectively "posture states 248"), and calculated posture state durations 250A, 250B, 250C, 250D, 250E and 250F (collectively "posture durations 250") for each of posture states 248. In addition, screen 244 presents return button 252 and sleep quality button 242.

Heading 245 presents screen information that explains what data is being presented in screen 244, including the units of the posture durations 250. Just as in screen 210, time intervals 246 are the specified days for which the proportional posture information is provided. Each of posture states 248 are provided, upright, upright and active, lying back, lying front, lying right, and lying left. Screen 244 breaks apart each of the lying down postures to provide more detailed information to the clinician than shown in posture duration graph 236 of FIG. 11. Alternatively, refinement of the lying down posture states may be expressed by showing additional bars in graph 236 of FIG. 11, or showing sub-bars indicating lying back, lying front, lying right, and lying left posture states and associated percentages within the lying posture state bar of FIG. 11. In the example of FIG. 12, all of posture durations 250 are provided in hours and minutes for each of the days specified in time intervals 246. In this example, posture durations 250 are not averages, but the actual, total duration for which patient 12 occupied each posture state during the respective days.

If the clinician again wants to view posture duration graph 236, the clinician may select return button 252 ("Show BarChart"). This input received from the clinician may be considered to be a proportional posture input to again initiate the presentation of posture duration graph 236. Again, the clinician may select sleep quality button 242 to view sleep quality information. In some examples, the clinician may be further able to view posture state frequency values for each of the posture states in each time interval. The posture state frequency value is the number of times that patient 12 was engaged in each posture state 248. The number of times may refer to the number of discrete, noncontiguous times the patient occupied a posture state. When patient 12 occupies a first, given posture state, then transitions away to one or more other posture state, and then transitions back to the first posture state, patient 12 has occupied the first posture state twice, such that the posture state frequency value for the first posture state is two.

In addition, the clinician may be able to scroll through each of the individual posture state durations throughout the day that make up each of the total posture durations 250. If patient 12 occupied a first posture state two times for "n" minutes and "m" minutes, respectively, the user may view the total duration "n"+"m", or the individual durations "n" and "m". Also, in some cases, the programmer may permit the user to view the time of day (or time within the time interval) at which the individual durations occurred. In examples where time intervals 246 are greater than a day, posture durations 250 may be averaged for each day.

Figure 13A:
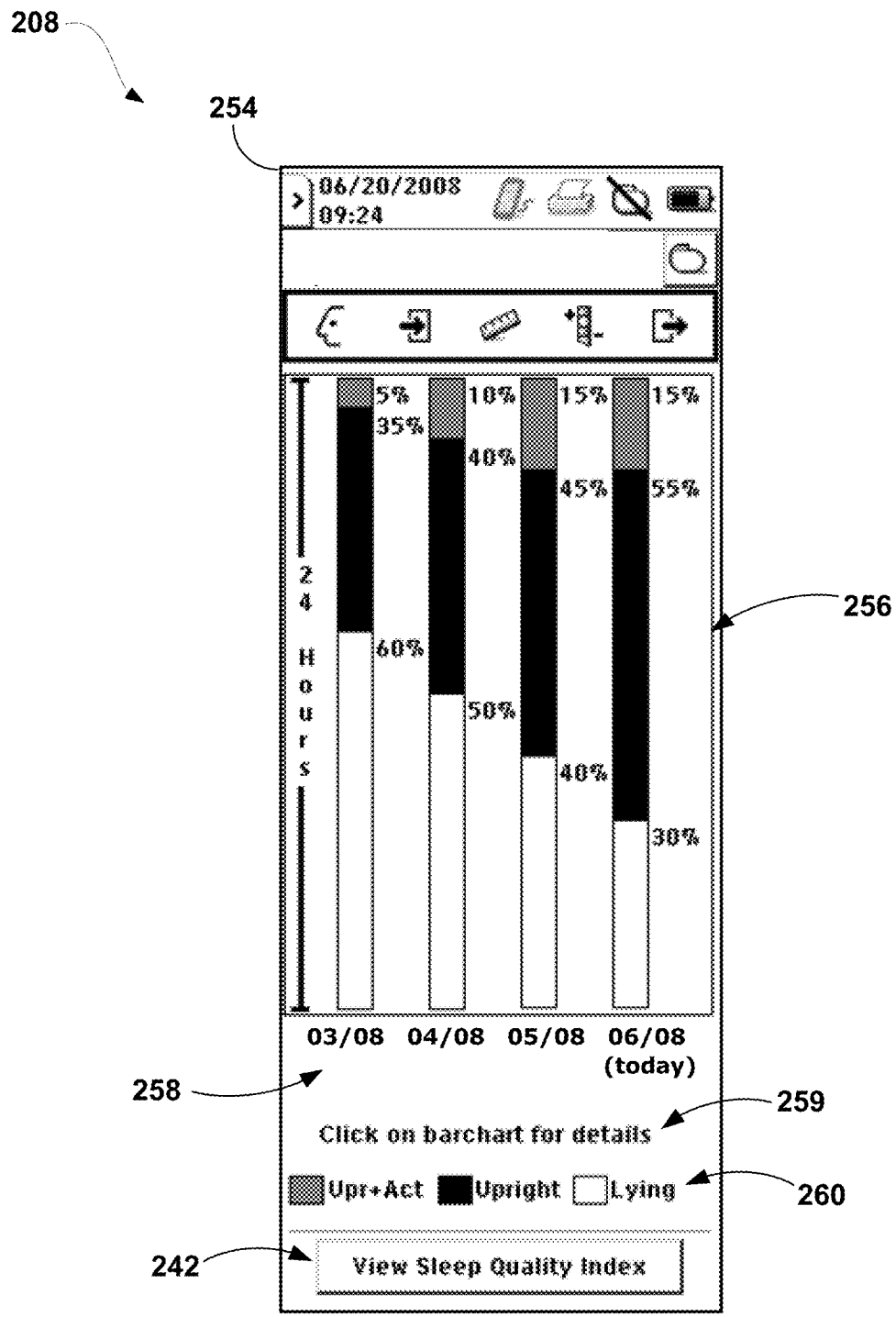
FIG. 13A is a conceptual diagram illustrating an example user interface for presenting graphical proportional posture information averaged for several larger time intervals, such as weeks or months.

FIG. 13A is a conceptual diagram illustrating an example user interface for presenting graphical proportional posture information averaged for several months. Substantially similar to screen 210 of FIG. 11, screen 254 of user interface 208 displays objective data derived from posture state data detected by posture state module 86 based upon the posture and activity of patient 12. However, the proportional posture data may be averaged over a time interval of one month, for example. In this case, posture data may be obtained for multiple time sub-intervals within the month, such as days or weeks, and then averaged for the month to provide a monthly average of each posture state duration. Alternatively, in other embodiments, posture data may be obtained over the entire monthly time interval without calculating the average data from sub-intervals within the respective time interval.

Posture duration graph 256 includes proportional posture information that includes the average posture durations for each of three posture states each day during each of the indicated months defined by time intervals 258. In the example of FIG. 13A, the months are 03/08 (March 2008), 04/08 (April 2008), and so forth. Posture state key 260 defines each of the posture segments that make up the posture bar for each time interval 258. As shown in FIG. 13A, the average percentage of time that patient 12 spent in each posture state every day of the month changed between each of the consecutive months shown as time intervals 258. The months used as time intervals 238 may have been selected by the clinician or automatically selected by processor 104 based upon the proportional posture information, most recent posture state data, or the amount of time stimulation therapy was being delivered. For example, processor 104 may be configured to not present proportional posture information for time intervals in which stimulation was delivered for less than ten percent of each day in the time interval.

Posture duration graph 256 illustrates a trend indicating that patient 12 is in the upright posture state for a much greater duration in more recent months than in previous months of the therapy. Therefore, it may be possible to infer that patient 12 is responding well to effective therapy by being able to be up and out of bed more frequently or for greater durations of time. Alternatively, the clinician may be attempting to treat patient 12 so that bed rest is tolerable with stimulation therapy. In this example, the more current therapy is not being effective at allowing patient 12 to remain lying down for long periods of time. Similar to screen 210, detail input note 259 informs the clinician to "Click on barchart for details." If the clinician clicks or selects a location anywhere within posture duration graph 256, processor 104 may present the average calculated posture state durations for each of the time intervals 258.

Figure 13B:
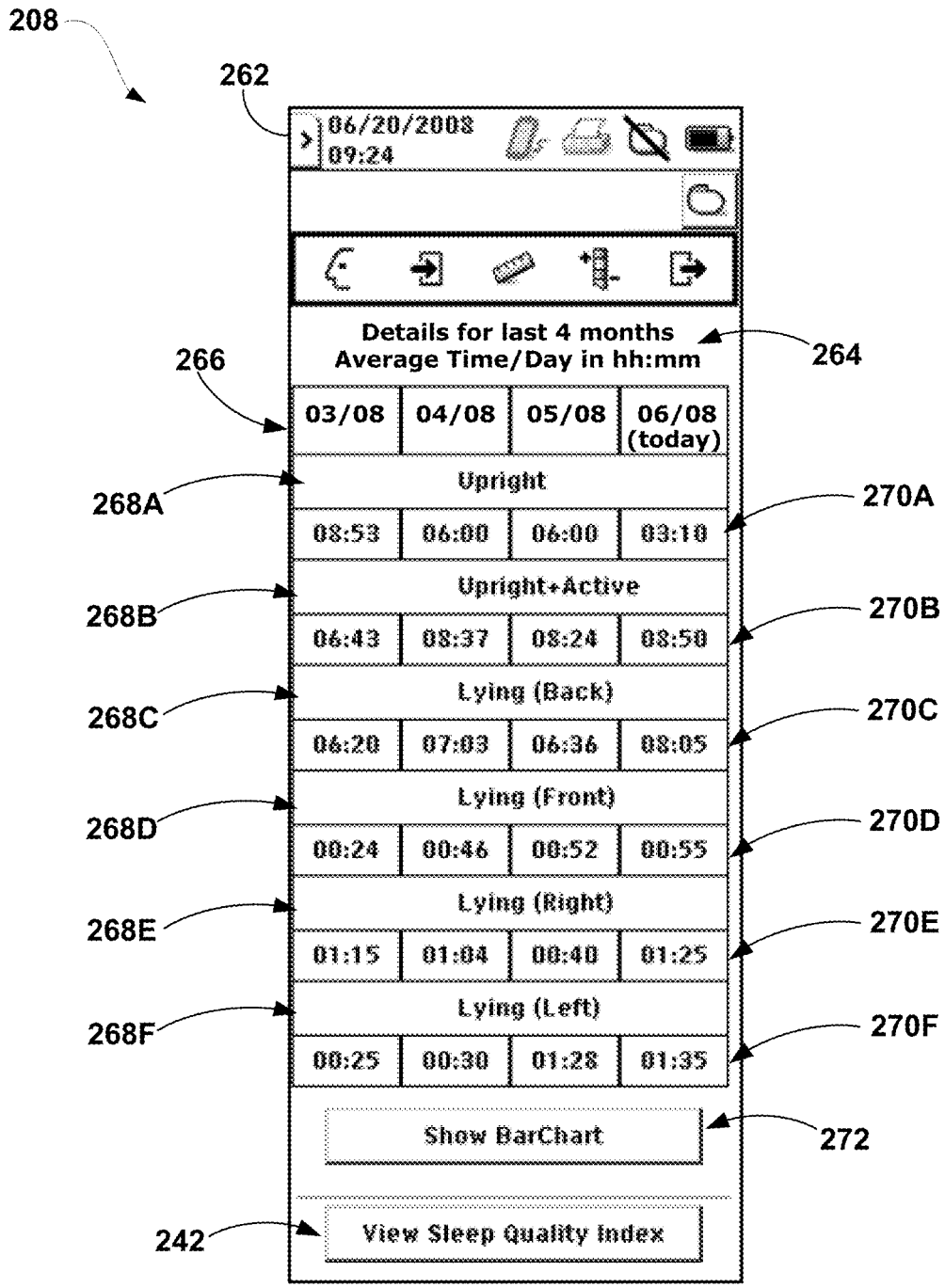
FIG. 13B is a conceptual diagram illustrating an example user interface for presenting detailed posture state durations for each time interval of FIG. 13A.

FIG. 13B is a conceptual diagram illustrating an example user interface 208 for presenting detailed posture state durations for each month of FIG. 13A. Screen 262 is substantially similar to screen 244 of FIG. 12. Screen 262 of user interface 208 presents the average calculated posture state durations for each of the posture states within each of the time intervals 258 from FIG. 13A. Screen 262 also presents heading 264, time intervals 266, posture states 268A, 268B, 268C, 268D, 268E and 268F (collectively "posture states 268"), and calculated posture state durations 270A, 270B, 270C, 270D, 270E and 270F (collectively "posture durations 270") for each of posture states 268. In addition, screen 262 presents return button 272 ("Show BarChart") and sleep quality button 242 ("View Sleep Quality Index").

Heading 264 presents screen information that explains what data is being presented in screen 254, including the units of the posture durations 270. Time intervals 266 are the specified months for which the proportional posture information is averaged for each day within the month, the same time intervals from FIG. 13A. Each of posture states 268 are provided: upright, upright and active, lying back, lying front, lying right, and lying left. Screen 262 breaks apart each of the lying down postures to provide more detailed information to the clinician than shown in posture duration graph 256 of FIG. 13A. All of posture durations 270 are provided in hours and minutes as the average amount of time per day in each time interval that patient 12 was engaged in each of posture states 268.

If the clinician again wants to view posture duration graph 256 again, the clinician may select return button 272. This input received from the clinician may be considered to be a proportional posture input to again initiate the presentation of posture duration graph 256. In some examples, the clinician may be further able to view posture state frequency value for each of the posture states in each time interval. The posture state frequency value, for posture durations averaged for the months of time intervals 266, is the number of times that patient 12 was engaged in each posture state 268. In some cases, posture durations 270 may be configured to present median durations or the most common durations.

In alternative examples of screen 262, user interface 208 may provide time intervals different than months. For example, the segment duration of each of the time intervals may be several days, weeks, several weeks, several months, years, time between clinician programming sessions, or any other customizable time interval desired by the clinician. The time between clinician programming sessions can be referred to as a therapy session. In addition, the time intervals do not need to be consecutive. The clinician or processor 104 may select representative months over a long therapy period in order for the clinician to derive any trends from the proportional posture information. In other examples, processor 104 may associate the therapy parameters used during therapy and present time intervals in which different therapy parameters were used. In this manner, the clinician may be able to compare the effectiveness of different therapy programs or groups of programs that may have been more effective at another point in past stimulation therapy.

Figure 14A:
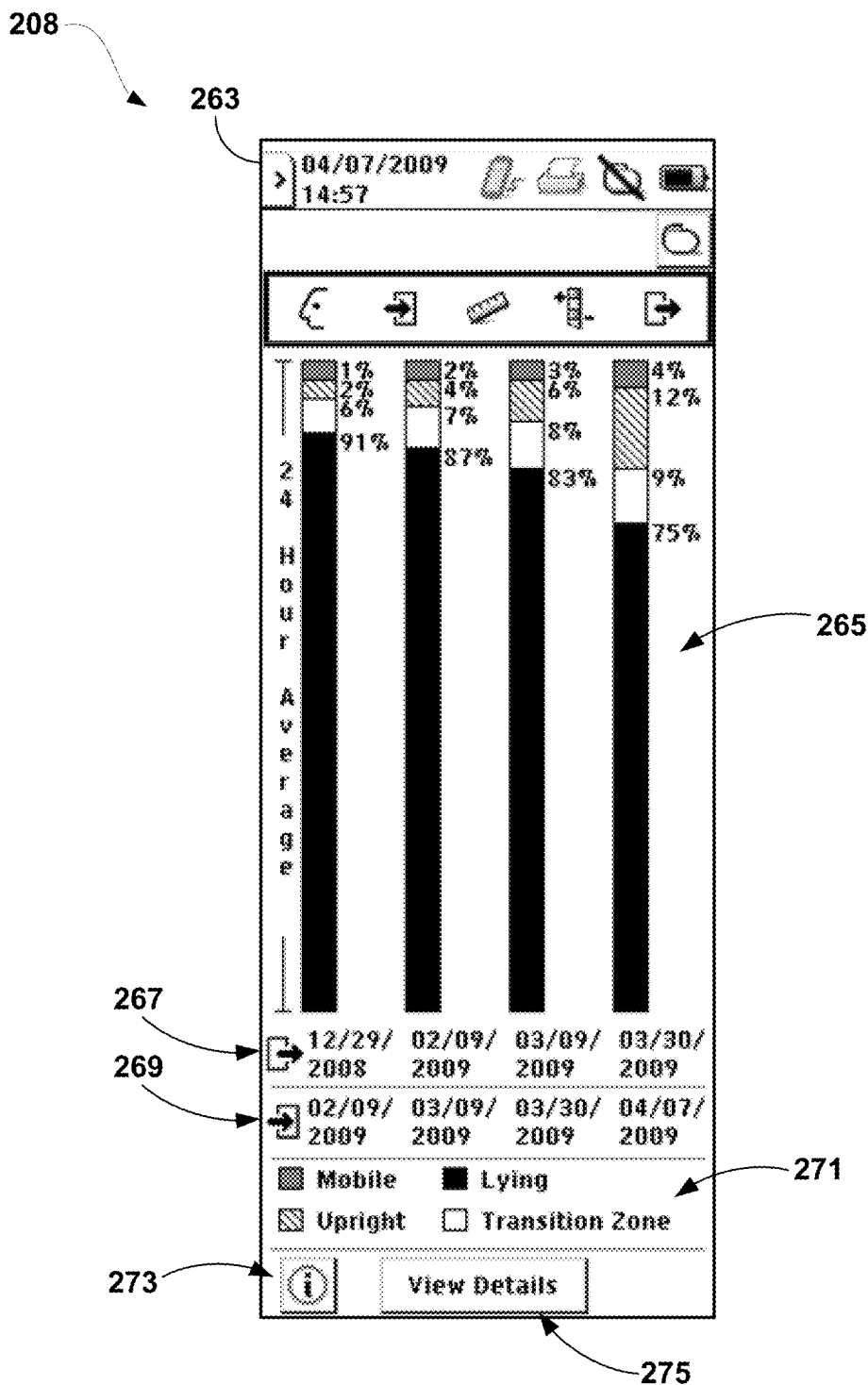
FIG. 14A is a conceptual diagram illustrating an example user interface for presenting graphical proportional posture information for previous therapy sessions.

FIG. 14A is a conceptual diagram illustrating an example user interface 208 that presents screen 263 and graphical proportional posture information as posture duration graph 265 for previous therapy sessions as time intervals. Substantially similar to screens 210 and 254 of FIGS. 11 and 13A, respectively, screen 263 of user interface 208 displays objective data derived from posture state data detected by posture state module 86 based upon the posture and activity of patient 12. However, in the example of FIG. 14A, the proportional posture data is presented and averaged over a time interval of one therapy session, rather than a fixed, regular time interval such as a day, week or month. In this case, posture state data obtained in therapy sessions between clinician programming sessions is combined and provided as posture duration graph 265 with proportional posture information for each of four previous therapy sessions. The proportional posture information for multiple time intervals, e.g., multiple therapy sessions, can be presented simultaneously to permit a clinician to evaluate proportional posture changes among different therapy sessions in which IMD 14 may have applied different therapy parameters. In general, the length of each therapy session is a function of the time between successive programming sessions, i.e., the time between a previous programming sessions that sets the parameters for the therapy session and a subsequent programming session in which the parameters may be adjusted. Consequently, the lengths of different therapy sessions may be different from one another, rather than fixed in length like fixed time intervals such as days, weeks or months.

The posture state data for each therapy session is analyzed to generate the proportion of time that patient 12 was engaged in each of the provided posture states. Although the posture state data may be averaged for each day, week or month within the therapy session, the overall percentage of time that patient 12 was engaged in each posture state would be presented as the same percentage values in posture duration graph 265. In other words, generation of a daily, weekly or monthly average is possible in the example of FIG. 14A, but the average would be the same for every day, week or month in the therapy session, as the data is accumulated over the entire therapy sessions instead of being tracked for individual days, weeks or months. In the example of FIG. 14A, a daily average can be calculated for a given therapy session, e.g., the therapy session between the programming session of 12/29/08 and the programming session of 02/09/2009, by simply dividing the applicable value by the number of days in that period.

Posture duration graph 265 includes proportional posture information that includes the average posture durations for each of four posture states each day during each of the indicated therapy sessions defined by clinic leave dates 267 and clinic arrive dates 269. During a therapy session, IMD 14 delivers therapy according to parameters specified in the previous programming session. In the example of FIG. 14A, clinic leave dates 267 indicate when patient 12 leaves the clinic following a programming sessions with new therapy parameters and include 12/29/2008 (Dec. 29, 2008), 02/09/2009 (Feb. 9, 2009), and so forth. Clinic arrive dates 269 indicate when patient 12 arrives at the clinic for a programming session to receive updates or adjustments to therapy parameters and include 02/09/2009 (Feb. 9, 2009), 03/09/2009 (Mar. 9, 2009), and so forth. Although clinic leave dates 267 and clinic arrive dates 269 define consecutive sessions, posture duration graph 265 may present non-consecutive sessions selected by external programmer 20, patient 12, or the clinician.

Posture state key 271 defines each of the posture segments that make up the posture bars of posture duration graph 265. Posture state key 271 includes "Mobile," "Upright," "Lying," and "Transition Zone" posture states. As shown in FIG. 14A, the average percentage of time that patient 12 spent in each posture state every day of the therapy session changed between each of the consecutive therapy sessions of posture duration graph 265. The therapy sessions used may have been selected by the clinician or automatically selected by processor 104 based upon the proportional posture information, most recent posture state data, or the amount of time stimulation therapy was being delivered. For example, processor 104 may be configured to not present proportional posture information for time intervals in which stimulation was delivered for less than ten percent of each day in the time interval.

Posture duration graph 256 illustrates a trend over multiple therapy sessions indicating that patient 12 is in the lying posture state for less time for each consecutive therapy session. Therefore, it may be possible to infer that patient 12 is responding well to effective therapy by being able to be up and out of bed in an upright posture more frequently or for greater durations of time. Alternatively, the clinician may be attempting to treat patient 12 so that bed rest is more tolerable with stimulation therapy. In this example, the more current therapy may not be effective at allowing patient 12 to remain lying down for longer periods of time. Detail input 275 informs the clinician that clicking the "View Details" button may provide more detailed proportional posture information. If the clinician clicks on detail input 275, processor 104 may present the average calculated posture state durations for each of the sessions defined by clinic leave dates 267 and clinic arrive dates 269.

Info button 273 may provide the user with additional information regarding the posture data presented in screen 263. For example, clicking on info button 273 may cause user interface 106 to present a pop-up window that reminds the user of certain changes to system 10 that could have affected the presented posture data. Resetting the orientation of the posture state module, adjusting a posture cone or vector, or otherwise changing how system 10 detects patient posture states and generates the posture state information may be of interest to the user. Additionally, information provided to the user by clicking info button 273 may include details about how the posture state data was used to generate the proportional posture information of posture duration graph 265.

Figure 14B:
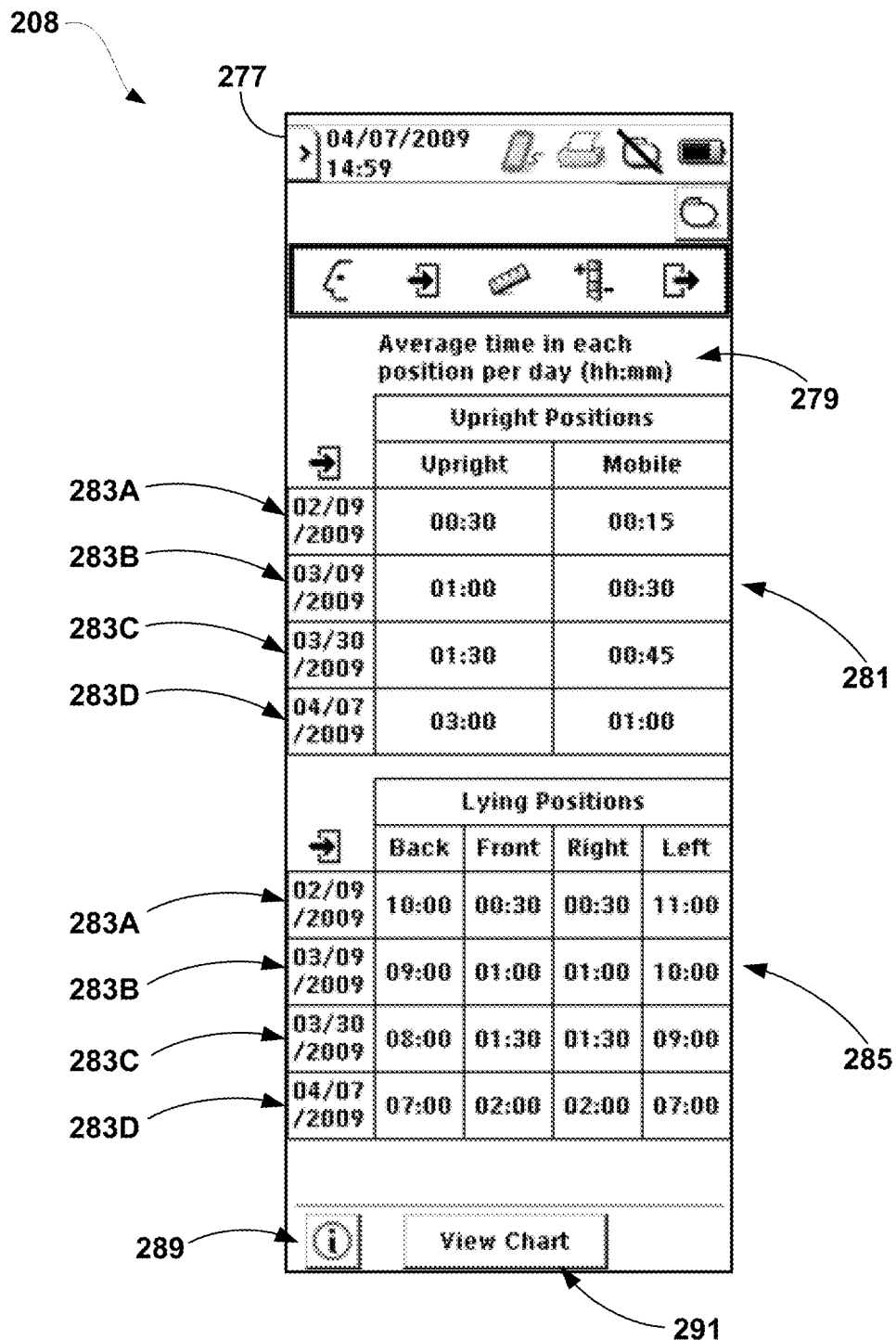
FIG. 14B is a conceptual diagram illustrating an example user interface for presenting detailed posture state durations of upright posture states and lying posture states.

FIG. 14B is a conceptual diagram illustrating an example user interface 208 for presenting detailed calculations of upright posture durations 281 and lying posture durations 285 for each therapy session. Screen 277 is substantially similar to screens 244 and 262 of FIGS. 12 and 13B, respectively. Screen 277 of user interface 208 presents the average calculated posture state durations for each of the posture states within each of the therapy sessions identified by clinic leave dates 283A, 283B, 283C, and 283D (collectively "clinic leave dates 283) from FIG. 14A. Screen 277 also presents heading 279, upright posture durations 281, lying posture durations 285, and info button 289. In addition, screen 277 presents chart button 291 ("View Chart"). Again, posture state information may be displayed for multiple time intervals simultaneously to permit a clinician to observe a trend, especially when the clinician has adjusted therapy parameters of the therapy session associated with the time intervals.

Heading 279 presents screen information that explains what data is being presented in screen 277, including the units of the posture durations 281 and 285. Clinic leave dates 283 indicate the beginning date of the provided therapy session, as further defined in screen 263 of FIG. 14A. Upright posture durations 281 provides the average duration of each day of the respective therapy session that patient 12 engaged in both the upright posture state and the mobile posture state. For example, patient 12 spent an average of 30 minutes in the upright posture state and 15 minutes in the mobile posture state per day during the session started on Feb. 9, 2009. Lying posture durations 285 provides the average duration of each day of the respective therapy session that patient 12 engaged in each of the lying back, lying front, lying right, and lying left posture states. For example, patient 12 spent an average of 10 hours in the lying back posture state, 30 minutes in the lying front posture state, 30 minutes in the lying right posture state, and 11 hours in the lying left posture state per day during the session started on Feb. 9, 2009. Each of the averages provided by screen 277 may be rounded to the nearest minute, and all times may be presented in the hours and minutes format.

If the clinician again wants to view posture duration graph 265 (FIG. 14A), the clinician may select chart button 291. This input, chart button 291, received from the clinician may be considered to be a proportional posture input to again initiate the presentation of posture duration graph 265. In some examples, the clinician may be further able to view posture state frequency values for each of the posture states in each time interval. The posture state frequency value, for posture durations averaged for the specific sessions, is the number of times that patient 12 was engaged in each of the posture states of upright posture durations 281 and lying posture durations 285 in a given time interval. In some cases, one or both of upright posture durations 281 and lying posture durations 285 may be configured to present median durations or the most common durations within each session indicated by clinic leave dates 283.

Info button 289 may provide the user with additional information regarding the posture data presented in screen 277. For example, clicking on info button 289 may cause user interface 106 to present a pop-up window that reminds the user of certain changes to system 10 that could have affected the presented posture data. Resetting the orientation of the posture state module, adjusting a posture cone or vector, or otherwise changing how system 10 detects patient 12 posture states and generates the posture state information may be of interest to the user.

In alternative examples of screens 263 and 277, user interface 208 may provide time intervals different than consecutive therapy sessions. For example, the segment duration of each of the time intervals may be several days, weeks, several weeks, several months, years, or any other customizable time interval desired by the clinician. In addition, the time intervals do not need to be consecutive. The clinician or processor 104 may select representative sessions over a therapy period of many weeks, months or years in order for the clinician to derive any trends from the proportional posture information. In other examples, processor 104 may associate the therapy parameters used during therapy and present time intervals in which different therapy parameters were used. In this manner, the clinician may be able to compare the effectiveness of different therapy programs or groups of programs that may have been more effective at different points during the therapy of patient 12.

In the examples of FIGS. 11-14B, external programmer 20 may configure the display screen to permit vertical and/or horizontal scrolling so that additional information can be viewed, e.g., for time intervals separated by larger spans of time. Also, the display screen may permit screen splitting and/or scroll bar splitting, e.g., in a manner similar to word processing and spreadsheet applications, so that portions that would not otherwise be visible on the same screen can be made visible in side-by-side or top-and-bottom split screens. As an illustration, a split screen may permit more effective viewing of information for time intervals from April 2010 and May 2008.

Figure 15:
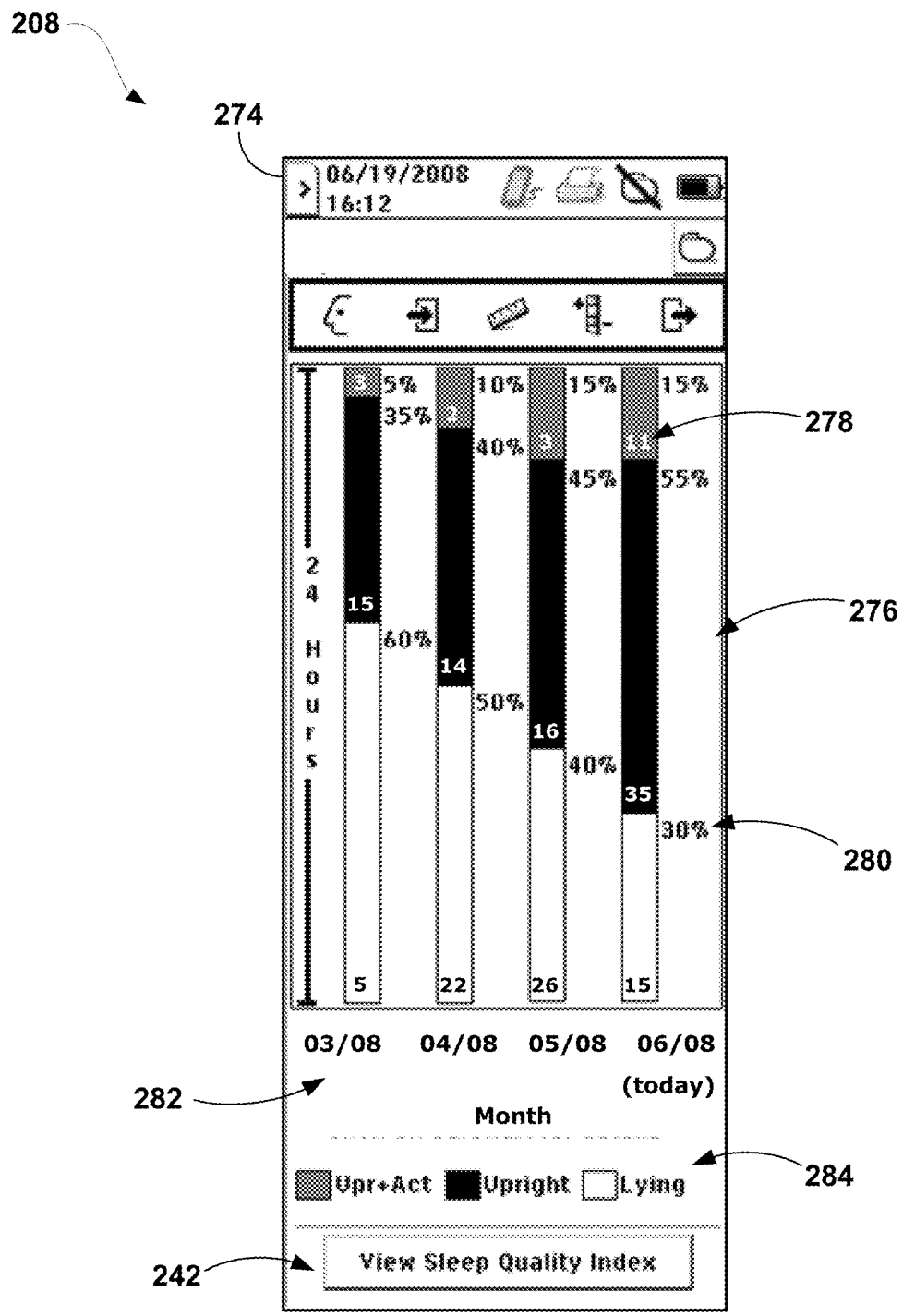
FIG. 15 is a conceptual diagram illustrating an example user interface for presenting graphical proportional posture information in addition to a posture state frequency value for each posture state.

FIG. 15 is a conceptual diagram illustrating an example user interface 208 for presenting graphical proportional posture information in addition to a posture state frequency value for each posture state. Screen 274 is substantially similar to screen 254 of FIG. 13A. However, screen 274 also presents a posture state frequency value 278, in addition to the posture duration 280 provided as a percentage and as graphical posture segment for each posture bar of posture duration graph 276. Time intervals 282 may again be consecutive months for which the posture states of patient 12 were recorded; however, other examples may provide different time intervals, e.g. therapy sessions defined by clinic visits. In addition, posture state key 284 provides the indication of each posture state.

Posture state frequency value 278 is provided for each posture state of each time interval 282. Posture state frequency value 278 is the average number of times patient 12 was engaged in each of the posture states during each time interval. In other words, posture state frequency value 278 is a count of how frequently patient 12 engaged in each posture state during an average day of each time interval. For example, the posture bar for June 2008 ("06/08") indicates that patient 12 was engaged in the upright, upright and active, and lying posture states for an average of 55 percent, 15 percent and 30 percent of each day during June 2008. In addition, posture state frequency value 278 located within the bar segment indicates that the upright, upright and active, and lying postures were assumed an average of 35 times, 11 times, and 15 times, respectively, during each day in June 2008. In alternative embodiments, posture state frequency value 278 may be located outside of each bar segment, in a separate graph, or be visible only when the clinician selects to view the detailed posture durations.

Posture state frequency values 278 may be beneficial to the clinician in determining how often patient 12 has tried to engage in a particular posture state. For example, a high posture state frequency value coupled to a small posture duration may indicate that the condition of patient 12 is preventing patient 12 from being engaged in the posture state for more than an unacceptably small period of time. Rather, patient 12 transitions to the posture state frequently but, in general, transitions out of the posture state relatively quickly. In this case, the clinician may attempt to adjust the stimulation parameters for more efficacious therapy. Of course, the combinations of posture state frequency values and posture durations may only be beneficial to objectively view the behavior of patient 12 when the clinician understands the condition of patient 12 that the stimulation therapy is designed to treat.

Figure 16A:
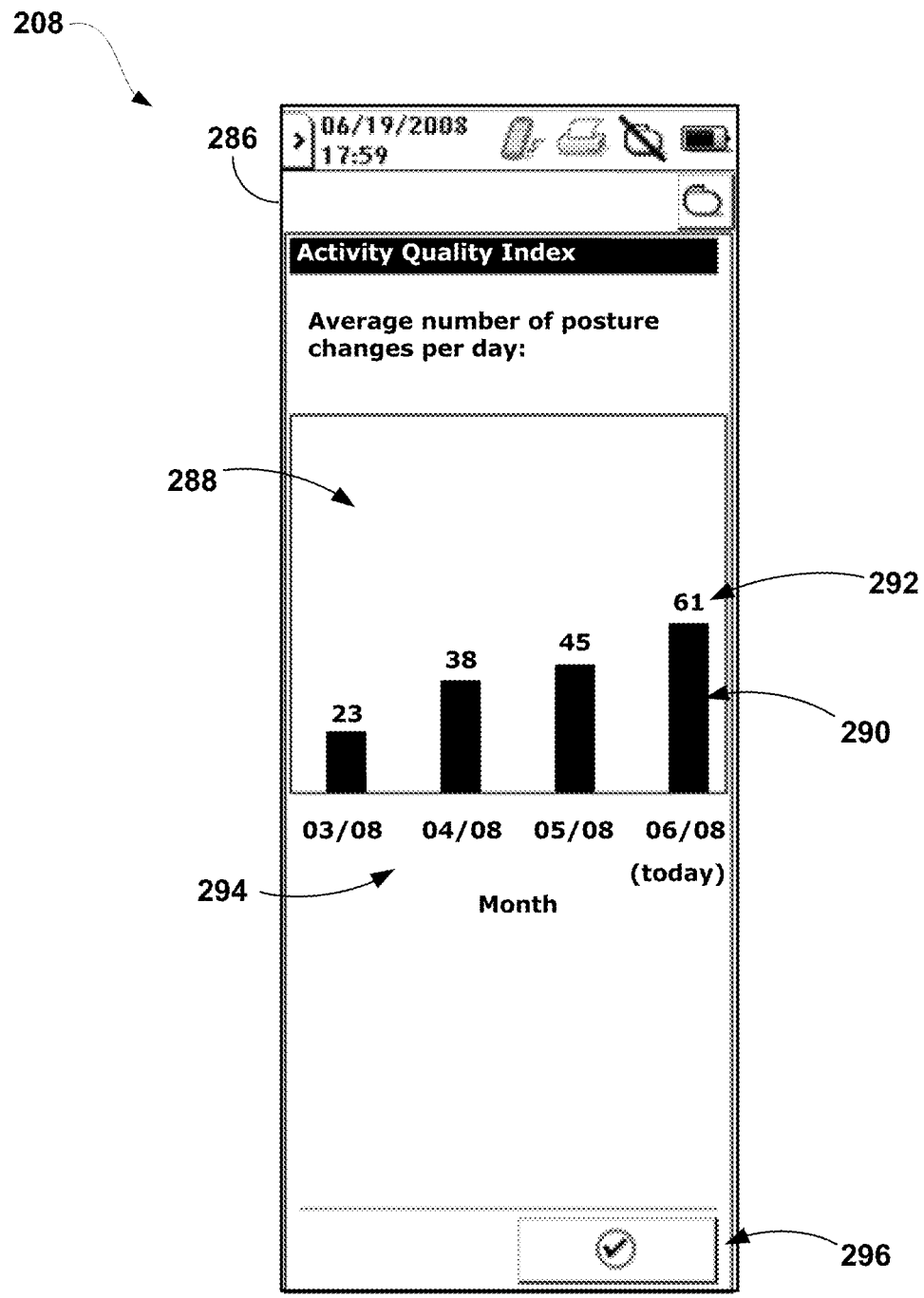
FIG. 16A is a conceptual diagram illustrating an example user interface for presenting an average quantified number of posture changes during selected time intervals of therapy.

FIG. 16A is a conceptual diagram illustrating an example user interface 208 for presenting an average quantified number of posture state changes during select time intervals of therapy. As shown in FIG. 16A, screen 286 of user interface 208 provides an activity quality index as activity graph 288, e.g., an average number of posture state changes for each time interval, to aid the clinician in objectively determining the efficacy of the therapy. Activity graph 288 includes activity bars 290 and activity value 292 for each of the four time intervals 294 of segment durations in months. Each activity bar 290 is a graphical representation of the average quantified number of posture state changes during each time interval. Accordingly, each activity value 292 is the respective numerical representation. Done button 296 may be selected when the clinician is finished viewing activity graph 288.

The quantified number of posture state changes may be an indicator of the effectiveness of stimulation therapy. Greater numbers of posture changes per day may indicate that therapy is successful because the therapy is allowing patient 12 to be engaged in a variety of postures and activities. In the example of FIG. 16A, patient 12 has increased their average number of posture state changes from 23 per day in March to 61 per day in June to indicate at least somewhat successful therapy. A reduction in the number of posture state changes per day may indicate that the therapy is no longer effective in treating the condition of patient 12. In other examples, activity graph 288 may present information identifying the particular therapy programs or groups of programs used during the respective time interval to correlate the therapies with posture state change information. This type of correlation may assist the clinician in narrowing in on the appropriate therapy parameters to treat patient 12.

Figure 16B:
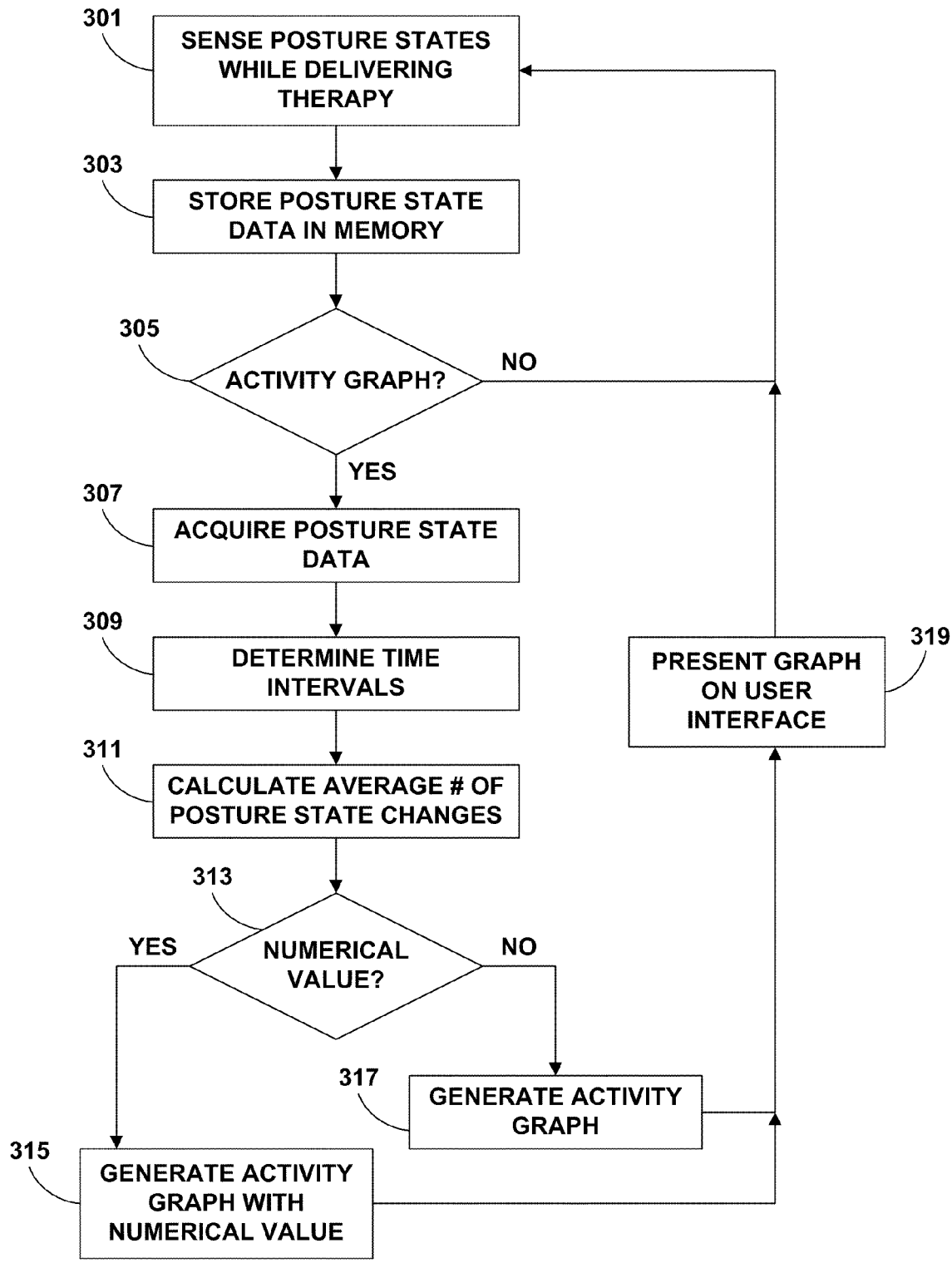
FIG. 16B is a flow diagram illustrating an example method for presenting an average quantified number of posture changes during selected time intervals of therapy.

FIG. 16B is a flow diagram illustrating an example method for presenting an average quantified number of posture changes during selected time intervals of therapy. In the example of FIG. 16B, posture state module 86 senses the posture states in which patient 12 engages while IMD 14 delivers stimulation therapy to patient 12 (301). Processor 80 then stores the sensed posture states as a plurality of posture state data within memory 82 of IMD 14 (303). If there is no request from the user to view an activity graph (305), IMD 14 continues to sense posture states and deliver therapy to patient 12 (301). If user interface 106 of external programmer 60 receives a request from the user to present the activity graph (305), then processor 104 acquires the posture state data from IMD 14 via telemetry circuit 110 (307). In other examples, processor 104 may first acquire posture state data from IMD 14 during a routine communication session and then acquire the posture state data from memory 108 of external programmer 20 when required to display the activity graph.

Once processor 104 has access to the posture state data, processor 104 determines the time intervals that will be used for the activity graph (309). The time intervals may be a therapy session, day, week, month, customized durations, or any other durations requested by the user or predetermined by processor 104. Processor 104 then analyzes the posture state data in order to calculate the average number of posture changes of each day in the determined time intervals (311). If the activity graph should include the numerical value of the changes in addition to the activity bars (313), processor 104 generates the activity graph with activity bars and numerical values for each time interval (315). If the activity graph is not to include the numerical value (313), processor 104 generates the activity graph with only the activity bars (317). In other examples, processor 104 may present only the numerical values of the average posture changes.

Once processor 104 generates the appropriate activity graph, user interface 106 presents the activity graph to the user via external programmer 20 (319). System 10 then continues to sense posture states while delivering therapy to patient 122 (301). In other examples, the activity graph may be presented by any local or networked external device.

Figure 17:
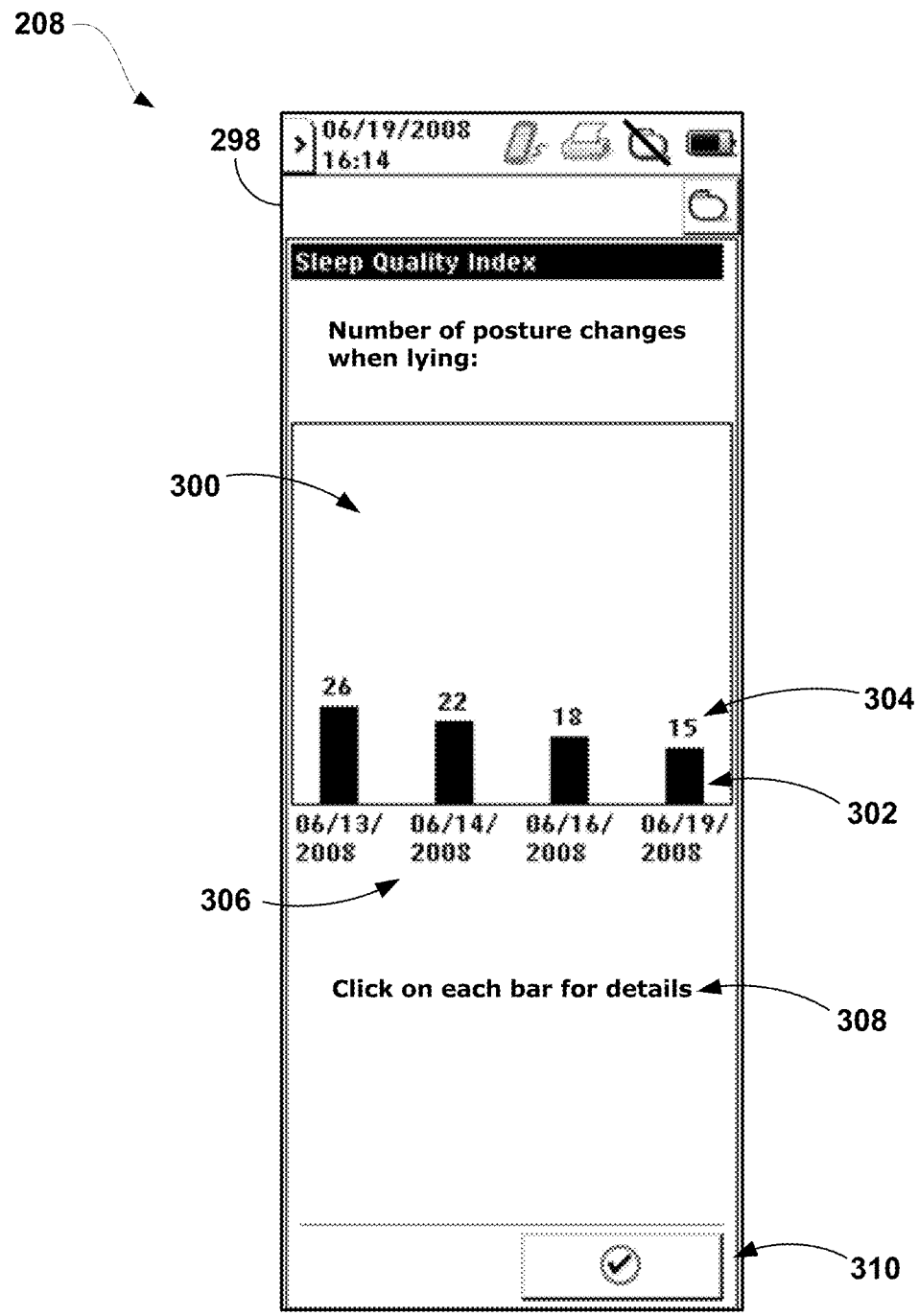
FIG. 17 is a conceptual diagram illustrating an example user interface for presenting sleep quality information as a graph of the quantified number of posture state changes when the patient is lying down.

FIG. 17 is a conceptual diagram illustrating an example user interface 208 for presenting sleep quality information as a graph of the quantified number of posture state changes when the patient is lying down. In general, presentation of sleep quality information may include obtaining posture state data sensed by a medical device for a patient, and generating sleep quality information based on lying posture state changes (e.g., transitions among lying front, lying back, lying right and lying left) indicated by the posture state data. The sleep quality information can then be presented to a user via a user interface.

As shown in FIG. 17, screen 298 of user interface 208 presents sleep quality information via sleep quality graph 300 and done button 310. As mentioned previously, the clinician may select sleep quality button 242 to navigate to screen 298. In other words, processor 104 may present screen 298 once the sleep quality input is received from the clinician. Screen 298 also provides done button 310 to return the clinician to the previous screen of the user interface. Alternatively, the clinician may be able to access sleep quality graph 300 via a separate menu item within user interface 208.

Sleep quality graph 300 may assist the clinician, and even patient 12, in determining how therapy aids the quality of sleep. Sleep quality graph 300 includes change bars 302 to graphically represent the number of lying posture changes and change values 304 to numerically represent the number of lying posture changes. In addition, time intervals 306 show that each interval is a non-consecutive day. More lying down posture changes are indicative of restlessness or continued symptoms that interrupt deep sleep. For example, on Jun. 13, 2008 ("06/13/2008"), patient 12 made 26 changes to their lying down posture state. However, by Jun. 19, 2008 ("06/19/2008), patient 12 only made 15 changes to their posture state when lying down. This may indicate to the clinician that patient 12 is responding to effective stimulation therapy. In some examples, sleep quality graph 300 may include an association to the particular stimulation program or group of programs used to deliver therapy. The clinician may be able to determine which programs or groups are most effective at allowing patient 12 to sleep during the night.

Detail input note 308 informs the clinician to "Click on each bar for details." If the clinician clicks or selects a sleep quality bar within sleep quality graph 300, processor 104 presents the number of different transitions from each lying posture or the number of transitions between each of the lying down postures.

IMD 14 may detect sleep by detecting consecutive lying down postures that indicate patient 12 is attempting to sleep. However, tracking lying down postures may not be an accurate indication of actual sleep of patient 12 because the patient may not actually be sleeping when lying down. Therefore, some embodiments of IMD 14 may monitor a physiological parameter of patient 12 in addition to tracking lying down postures. For example, posture state module 86, or a separate module, may include a physiological sensor that detects changes within patient 12 indicative of sleep. The physiological sensor may include electrodes, pressure sensors, accelerometers, or other sensors capable of detecting heart rate, breathing rate, electroencephalograph (EEG) signals, eye movement, or any other physiological parameter that may aid clinician programmer 60 in determining when patient 12 is actually asleep. As an alternative, or further feature, sleep quality may be detected based in part by a time of day such that lying posture changes during normal sleeping hours for the patient are tracked to indicate sleep quality. For example, lying posture changes occurring between 10 P.M. and 6 A.M. could be tracked to provide an indication of sleep quality.

In the example of FIG. 17, sleep quality is generally expressed in terms of the number of lying posture changes in a time interval. Additionally, or alternatively, the percentage of time in which the patient occupies each lying posture (lying back, lying front, lying right, lying left) may be presented. In this manner, the clinician may observe the patient's predominant sleeping position and changes in the position during the course of the night. As a further refinement, IMD 14 or external programmer 30 may track specific transitions from one lying posture to another, e.g., lying back to lying left, or vice versa, and/or time spent in particular postures, to evaluate relative patient discomfort in different postures.

Figure 18:
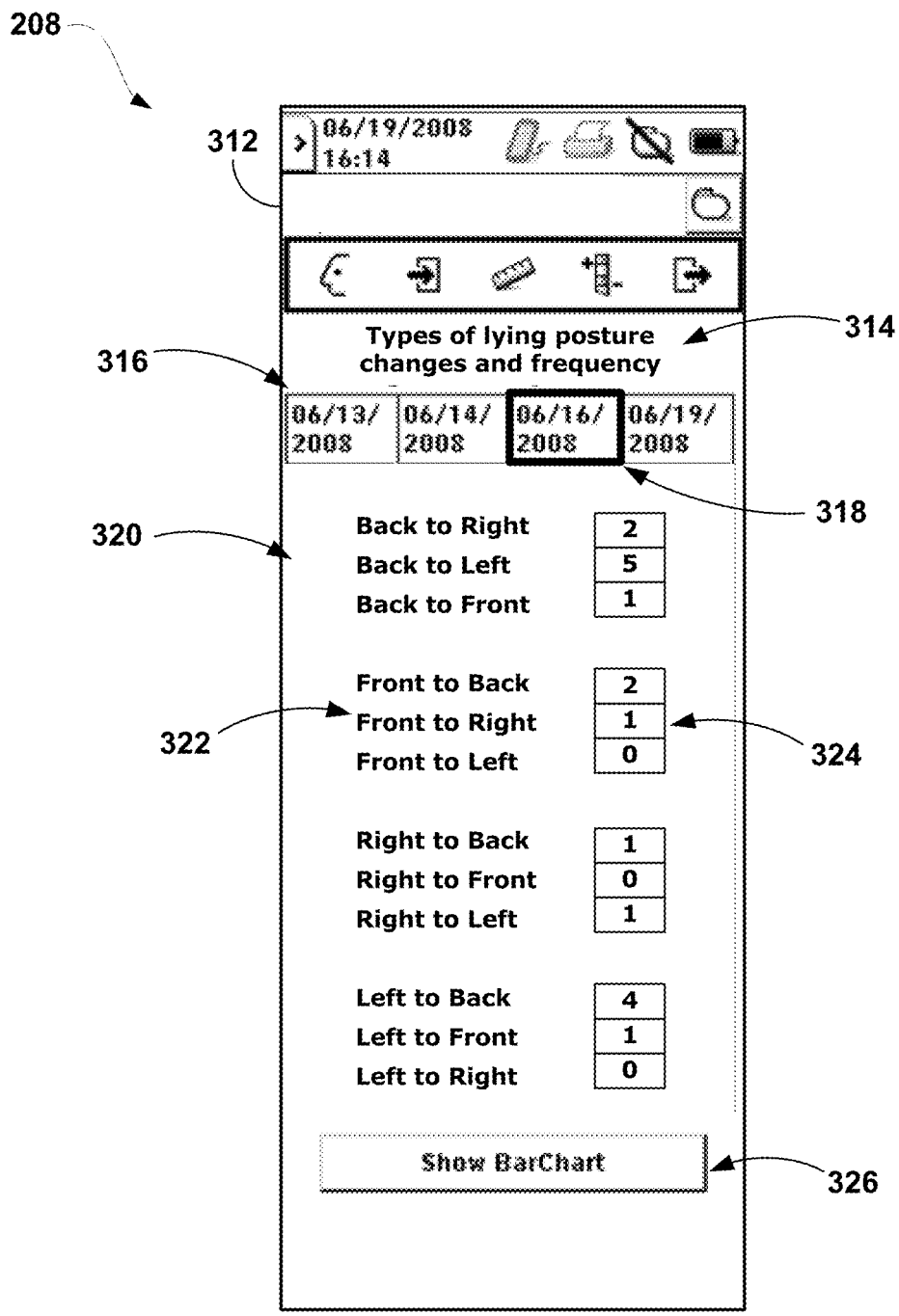
FIG. 18 is a conceptual diagram illustrating an example user interface for presenting details on the number of times the patient moved between each posture state during sleep.

FIG. 18 is a conceptual diagram illustrating an example user interface 208 for presenting details on the number of times patient 12 moved between each posture state during sleep associated with FIG. 17. As shown in FIG. 18, screen 312 of user interface 208 provides heading 314, time intervals 316, and detailed posture state data 320 that includes the number of changes from each posture state to a different posture state. Heading 314 describes the posture state data presented in screen 312. Posture state transitions 322 indicates the specific posture state transitions and change quantity 324 is the number of times patient 12 performed that posture state transition in a time interval. Interval indicator 318 encircles the time interval "06/16/2008" because that is the time interval that the clinician selected to view posture state data 320 in the example of FIG. 18. The clinician can then select Show BarChart button 326 to navigate back to the sleep quality graph 300 in order to view the sleep quality information from the multiple time intervals.

As described with reference to FIGS. 17 and 18, the sleep quality information may include sleep quality information for each of a plurality of time intervals. The sleep quality information for each of the time intervals may indicates a number of changes from a plurality of different lying posture states during the respective time interval. For example, the sleep quality information may indicate a number of changes from each of a plurality of different lying posture states during a time interval. In particular, the sleep quality information may indicate a number of changes from each of a plurality of different lying posture states to each of the other lying posture states during a time interval.

The clinician may desire to view the specific posture state data to uncover which posture state transitions 322 occur most frequently. In particular, screen 312 may present the number of transitions for each specific lying posture state transition. Examples of lying posture state transitions, as shown in FIG. 18, include back to right, back to left, back to front, front to back, front to right, front to left, right to back, right to front, right to left, left to back, left to front, and left to right. The number of times each transition was made by a patient during the time interval may be presented as shown in FIG. 18. More frequent changes away from a certain posture state may indicate a deficiency with the therapy to treat patient 12 in that posture. More frequent changes to a certain posture may indicate that therapy is effective in that posture, or that the posture is desired by the patient 12. This specific transition information may be accompanied by posture duration information or other information that may be useful in evaluating sleep quality and therapeutic efficacy for different lying posture states that may be associated with sleep. In any case, posture state data 320 may allow the clinician to monitor various consistencies or abnormalities among the lying posture habits of patient 12.

Figure 19:
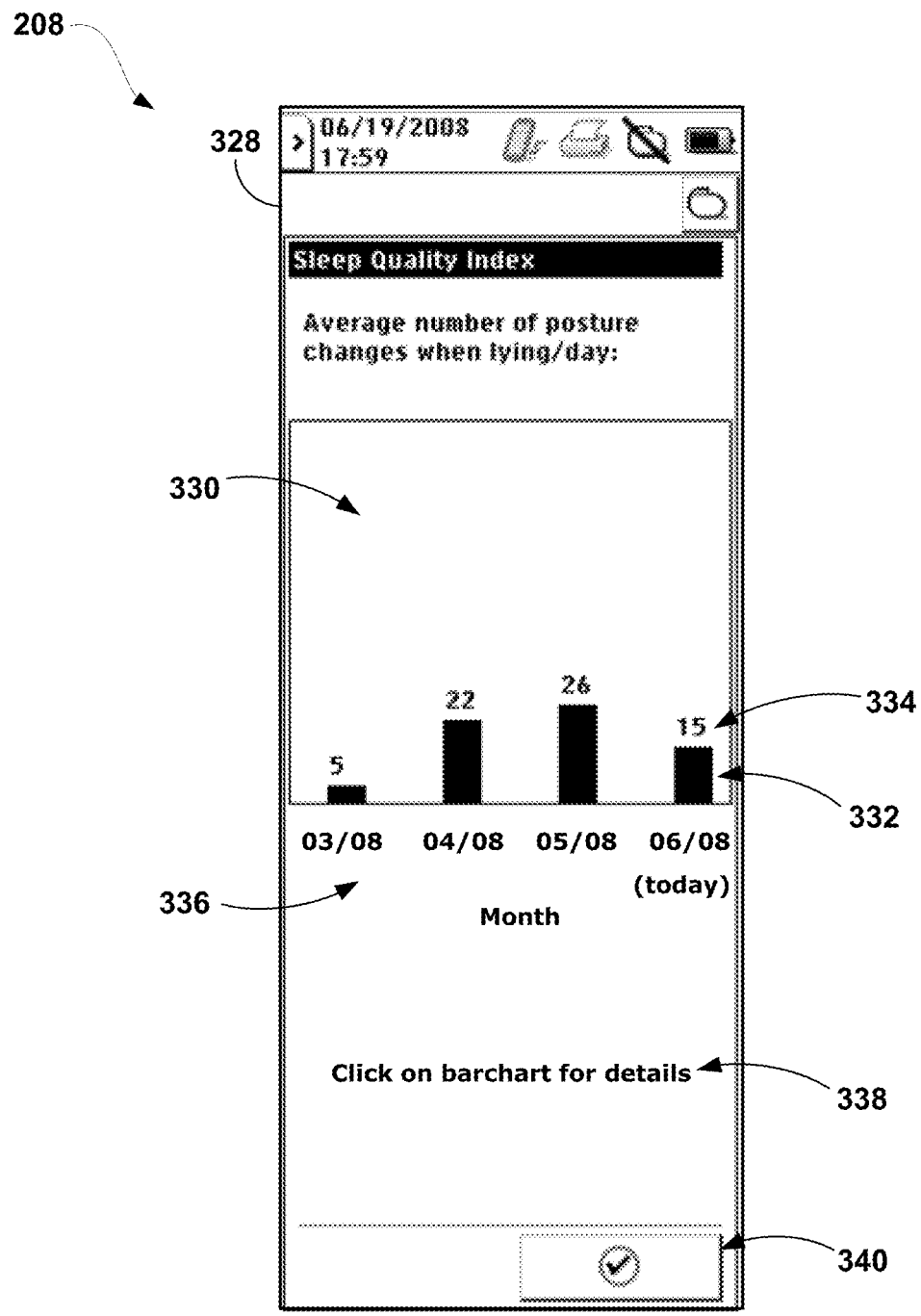
FIG. 19 is a conceptual diagram illustrating an example user interface for presenting the average number of posture state changes when the patient is lying down for a given time interval.

FIG. 19 is a conceptual diagram illustrating an example user interface 208 for presenting the average number of posture state changes when patient 12 is lying down for a given month. Screen 328 may be substantially similar to screen 298 of FIG. 17, but screen 328 presents averaged numbers of posture changes for a given month. In other examples, screen 328 may present therapy sessions as the time interval instead of months. As shown in FIG. 19, screen 328 of user interface 208 presents sleep quality information via sleep quality graph 330 and done button 340. As mentioned previously, the clinician may select sleep quality button 242 to navigate to screen 330. In other words, processor 104 presents screen 328 once the sleep quality input is received from the clinician. Screen 328 also provides done button 340 to return the clinician to the previous screen of the user interface. Alternatively, the clinician may be able to access sleep quality graph 330 via a separate menu item within user interface 208.

Sleep quality graph 330 may assist the clinician, and even patient 12, in determining how therapy aids the quality of sleep as trends over time. Sleep quality graph 330 includes change bars 332 to graphically represent the average number of lying posture changes per day within the time interval and change values 334 to numerically represent the average number of lying posture changes per day. In addition, time intervals 336 show that each interval is a consecutive month. The trends suggested by sleep quality graph 330 is that patient 12 slept better during March and June than April or May. This may indicate to the clinician that patient 12 is responding to recent change in stimulation therapy, or that the clinician should revert to using previously used stimulation parameters. In some examples, sleep quality graph 330 may include an association to the particular stimulation program or group of programs used to deliver therapy.

Similar to FIG. 17, detail input note 338 informs the clinician to "Click on barchart for details." If the clinician clicks or selects a sleep quality bar within sleep quality graph 330, processor 104 presents the average number of times patient 12 left each of the posture states per day within the time interval.

Figure 20:
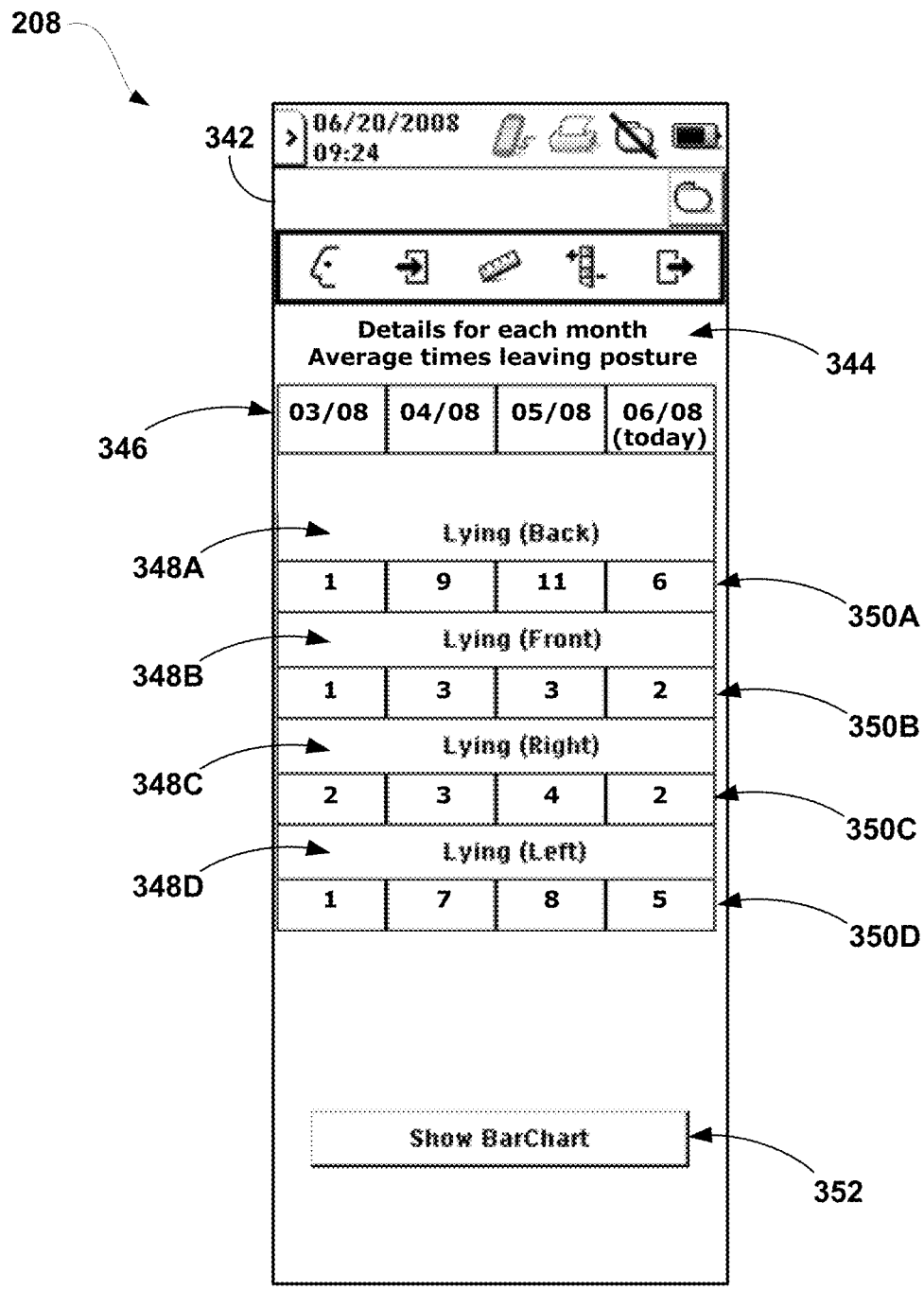
FIG. 20 is a conceptual diagram illustrating an example user interface for presenting detailed information on the average number of times the patient left each lying posture.

FIG. 20 is a conceptual diagram illustrating an example user interface 208 for presenting detailed information on the average number of times patient 12 left each lying posture. Screen 342 is similar to screen 312 of FIG. 18. However, screen 342 only presents the average number of times each day patient 12 left each posture state. As shown in FIG. 20, screen 312 of user interface 208 provides heading 344, time intervals 346, posture states 348A, 348B, 348C, and 348D (collectively "posture states 348"), and associated leave values 350A, 350B, 350C, and 350D (collectively "leaving values 350"). Return button 352 allows the clinician to return to the sleep quality graph 330 of FIG. 19.

Heading 344 describes the posture state data presented in screen 342, which are the average number of times patient 12 left each posture state. For each of posture states 348, screen 342 presents the average number of times that patient 12 left each of the respective posture states, irrespective of the posture state to which patient 12 transitioned. Leaving values 350 are averages for the time interval, which may be rounded to the nearest whole leaving value. From the number of times that patient left each posture state, the clinician may be able to determine for which posture state 348 therapy is not effective when patent 12 lying down and attempting to sleep. For example, the time interval of May shows that patient 12 moved from the lying on their back position an average of eleven times a day. This may be excessive and indicate that patient 12 is getting little quality sleep. The clinician can then select return button 352 to navigate back to the sleep quality graph 330 in order to view the sleep quality information from the multiple time intervals.

Figure 21:
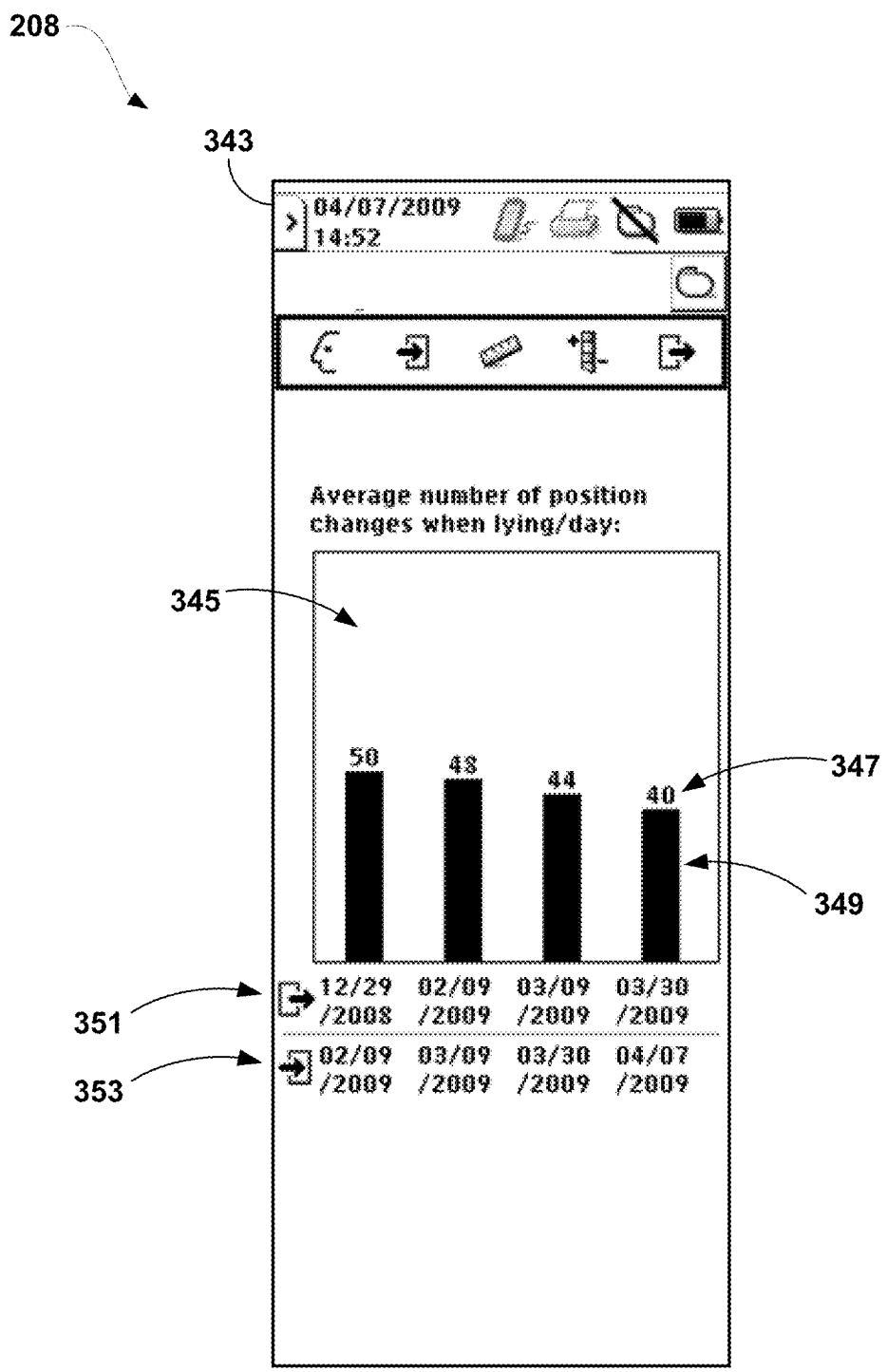
FIG. 21 is a conceptual diagram illustrating an example user interface for presenting an average number of posture state changes when the patient is lying down during each therapy session.

FIG. 21 is a conceptual diagram illustrating an example user interface 208 for presenting the average number of posture state changes when the patient is lying down during each therapy session. Screen 343 may be substantially similar to screen 328 of FIG. 19, However, screen 343 presents averaged numbers of posture changes for a given therapy session as the time interval. As shown in FIG. 21, screen 343 of user interface 208 presents sleep quality information via sleep quality graph 345. Change bars 349 graphically represent the average number of lying posture changes per day within the time interval and change values 347 numerically represent the average number of lying posture changes per day.

The time intervals for each of change bars 349 and change values 347 are provided as therapy sessions. Each therapy session is identified by the start date to the therapy session and the end date of the therapy session, typically determined by the date patient 12 visits a clinic for a programming session to review stimulation therapy efficacy and make parameter or program adjustments to therapy. Clinic leave dates 351 provide the start date for each of the four therapy sessions provided by screen 343, e.g., 12/29/2008 to represent Dec. 29, 2008. Clinic arrive dates 353 provide the end dates for each the four therapy sessions, e.g., 02/099/2009 to represent Feb. 9, 2009. Each therapy session may be as short as a day or as long as several months to several years. Although screen 343 may provide consecutive therapy sessions, other examples of screen 343 may provide only certain nonconsecutive therapy sessions depending upon the sleep quality information desired by the user or the sleep quality information most appropriate to review the therapy efficacy for patient 12.

Figure 22:
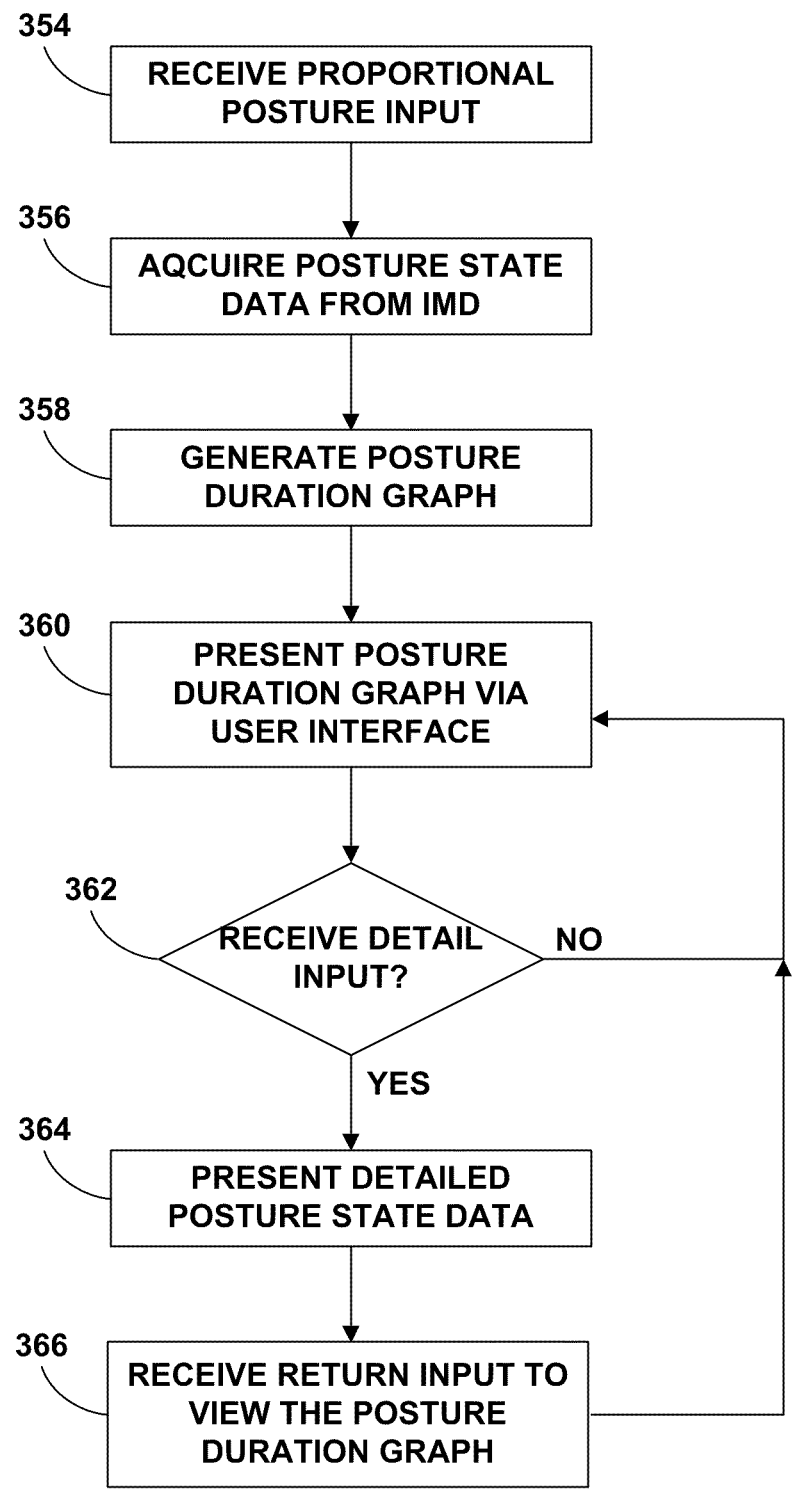
FIG. 22 is a flow diagram illustrating an example method for presenting proportional posture information to the user from recently stored posture state data.

FIG. 22 is a flow diagram illustrating an example method for presenting proportional posture information to the user from recently stored posture state data. The method of FIG. 22 will be directed to clinician programmer 60 as an example, but any external programmer 20 or computing device may perform these methods. As shown in FIG. 22, user interface 208 receives proportional posture input from the user, e.g., the clinician (354). The proportional posture input may be a request, entered via user interface, for presentation of proportional posture information. Processor 104 then acquires posture state data, e.g., from IMD 14 (356). Alternatively, processor 104 may acquire the posture state data from another device, such as patient programmer 30, additional sensors, or any other device that communicates with IMD 14 or a sensor of the system.

Processor 104 of programmer 60 may interrogate IMD 14 by wireless telemetry to retrieve such information. All of the information may be stored in IMD 14. Alternatively, programmer 60 may obtain only recent information from IMD 14, such as information obtained by IMD 14 since the last interrogation, and rely on information stored in the programmer from previous interrogations. Hence, the information may include information stored in programmer 60 from previous interrogations of IMD 14 and information freshly acquired from IMD 14. In some examples, processor 104 may reject any raw posture state data from short therapy sessions, when one or more therapy sessions are shorter than the session threshold, e.g., twenty-four hours. In this case, processor 104 may generate posture state output, such as sleep quality information or proportional posture information, based on the raw posture state data that is not rejected. Although processor 104 may simply not use the rejected posture state data this one time, processor 104 may also delete any raw posture state data that was rejected.

Next, processor 104 generates the posture duration graph in order to graphically present the posture state data to the user (358). Generating the posture duration graph may involve some graphical rendering or otherwise creating the graphical representation of the posture state data. Processor 104 then presents the posture duration graph via user interface 208 (360), e.g., as shown in FIG. 11.

If user interface 208 does not receive detail input signaling the user's desire to view the detailed posture state data (362), processor 104 continues to present the posture duration graph (360). If user interface 208 receives the detail input (362), then processor 104 presents the detailed posture state data via user interface 208 (364), e.g., as shown in FIG. 12. Upon receiving the return input to view the posture duration graph (366), processor 104 again presents the posture duration graph (360).

Figure 23:
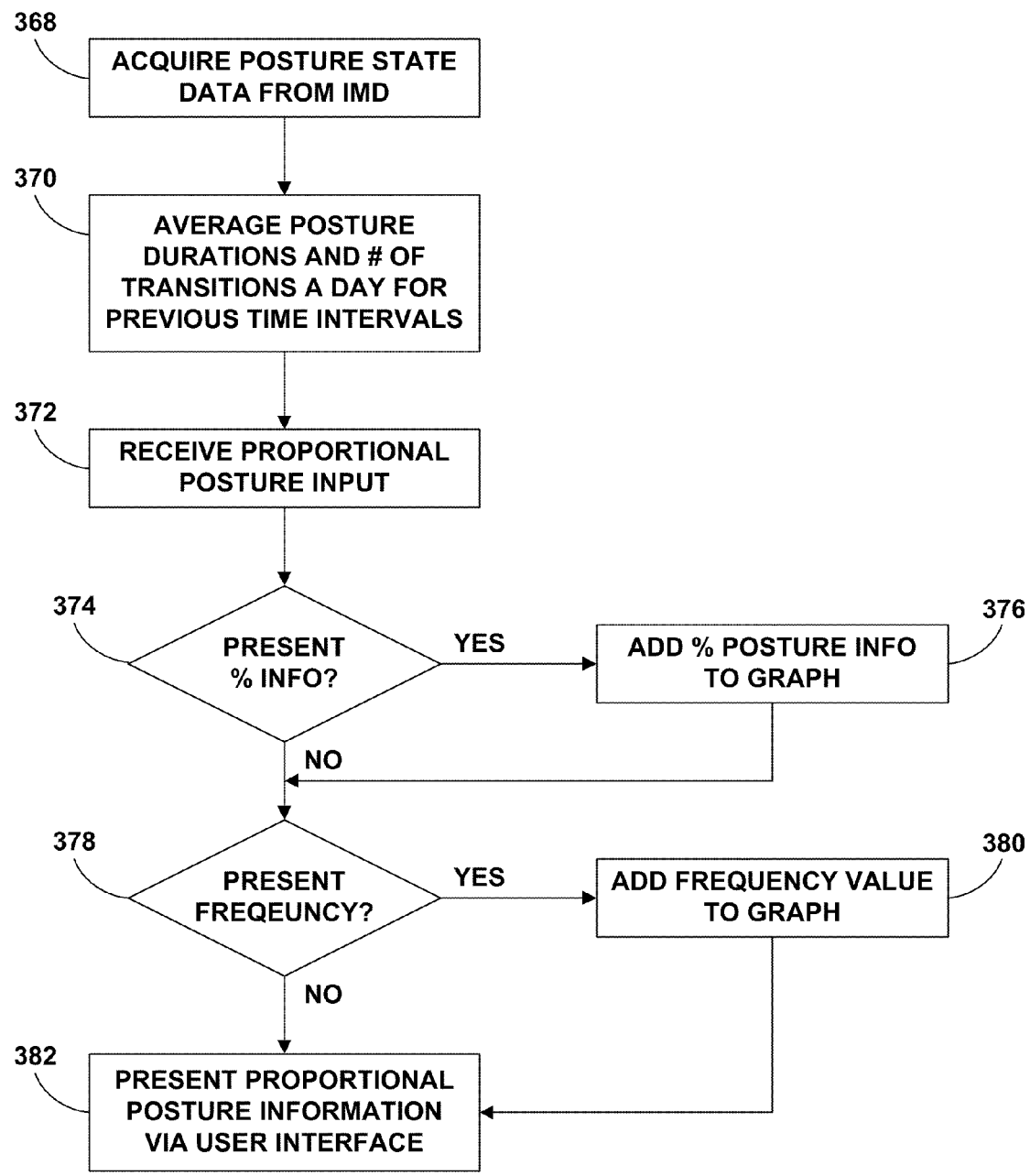
FIG. 23 is a flow diagram illustrating an example method for presenting specific posture state information to the user on the proportional posture graph.

FIG. 23 is a flow diagram illustrating an example method for presenting specific proportional posture information to the user on the posture duration graph. The method of FIG. 23 will be directed to clinician programmer 60 as an example, but any external programmer 20 or computing device may perform these methods. As shown in FIG. 23, processor 104 first acquires posture state data from IMD 14, for example (368). Next, processor 104 averages posture durations and the number of transitions a day for the determined time intervals (370). The segment duration of each time interval may be preselected or customized by the clinician. In the method of FIG. 23, processor 104 acquires the posture state data and performs the necessary calculations on the posture state data before the proportional posture information is requested by the clinician. While this may not need to be performed in this manner, it may allow for faster transitions for the clinician when navigating through user interface 208. In some examples, processor 104 may reject any raw posture state data from short sessions, when one or more sessions are shorter than the session threshold, e.g., twenty-four hours. Although processor 104 may simply not use the rejected posture state data this one time, processor 104 may also permanently delete any raw posture state data that was rejected.

Once user interface 208 receives the proportional posture input requesting the posture duration graph (372), processor 104 checks if percentage information is to be presented (374). If the percentage of time for each posture state is to be presented (374), then processor 104 adds the percentage information to the posture duration graph (376). Otherwise, processor 104 determines if the posture state frequency value should be added to the posture duration graph (378). If the posture state frequency value is to be added, processor 104 adds the posture state frequency value to the posture duration graph (380). Finally, processor 104 presents the proportional posture information in the form of the posture duration graph via user interface 208 (382).

Figure 24:
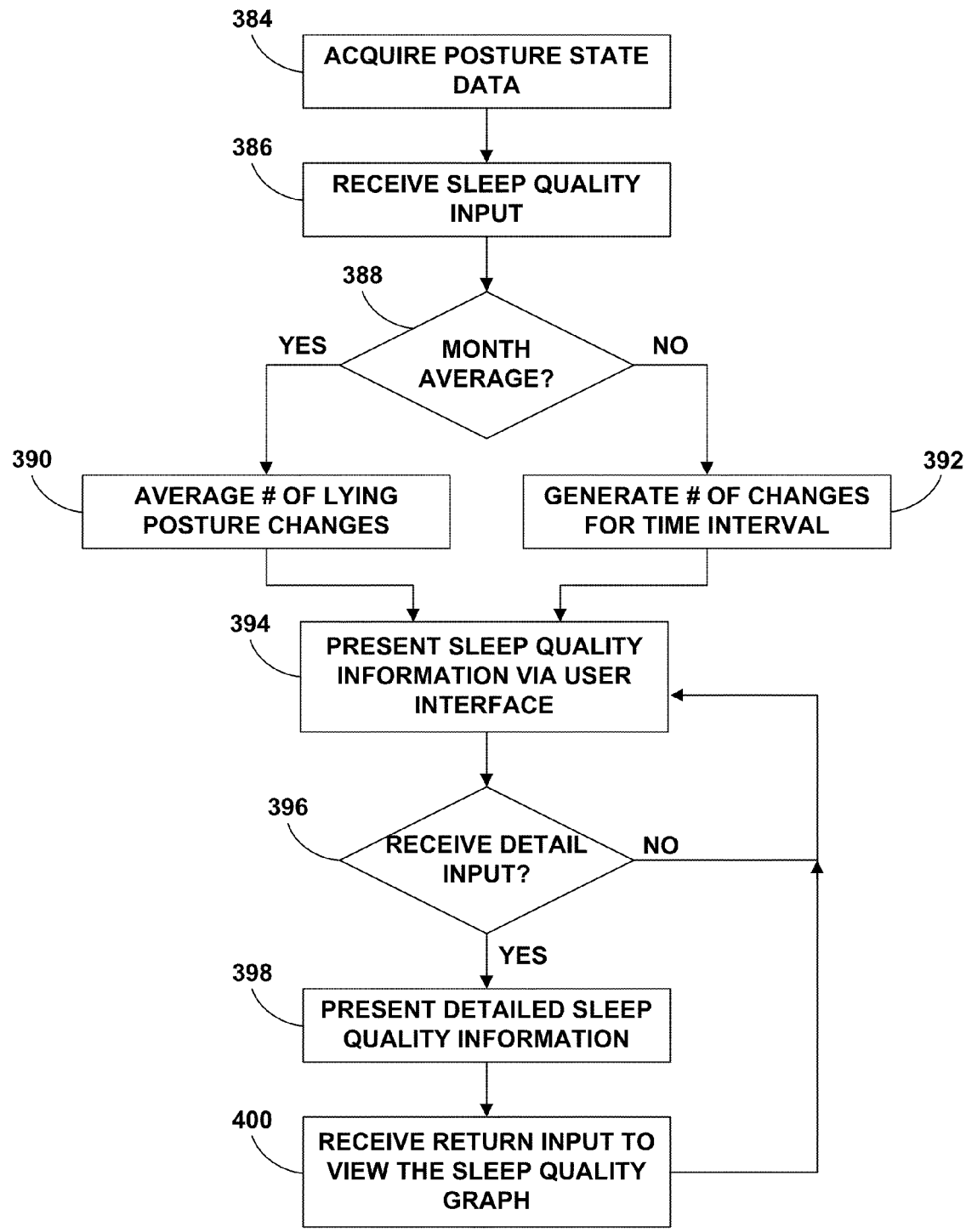
FIG. 24 is a flow diagram illustrating an example method for presenting sleep quality information derived from the posture state data.

FIG. 24 is a flow diagram illustrating an example method for presenting sleep quality information derived from the posture state data for a day or over a month time interval. Again, the method of FIG. 24 will be directed to clinician programmer 60 as an example, but any external programmer 20 or computing device may perform these methods. As shown in FIG. 24, processor 104 acquires posture state data from IMD 14, memory 108, or a combination of the two (384). Alternatively, processor 104 may acquire the posture state data from another device, such as patient programmer 30, additional sensors, such as externally worn sensors, or any other device that communicates with IMD 14 or a sensor of the system. Upon receiving the sleep quality input from the clinician (386), processor 104 then determines if the data needs to be averaged over the month segment duration of the time interval (388). If no averaging is needed because the sleep quality graph will be presented with day time intervals, the processor 104 generates the number of lying posture changes for each time interval (392). Otherwise, processor 104 averages the number of lying posture changes (390). As explained above, the time interval may be of any duration, and the time intervals do not need to be of equivalent durations. For example, the time intervals may be therapy sessions defined by when patient 12 visits the clinic.

Processor 104 next presents the sleep quality information as a sleep quality graph via user interface 208 (394). Upon receiving a detail input from the clinician (396), processor 104 presents detailed sleep quality information (398). As described in FIGS. 18 and 20, the detailed sleep quality information may be the number of each posture transition or the number of times patient 12 left each posture state. Processor 104 returns to the sleep quality graph once user interface 208 receives the return input from the clinician (400). In alternative examples, clinician programmer 60 may require additional steps in order to provide customizable graphical information to the clinician or provide data flexibility.

Figure 25:
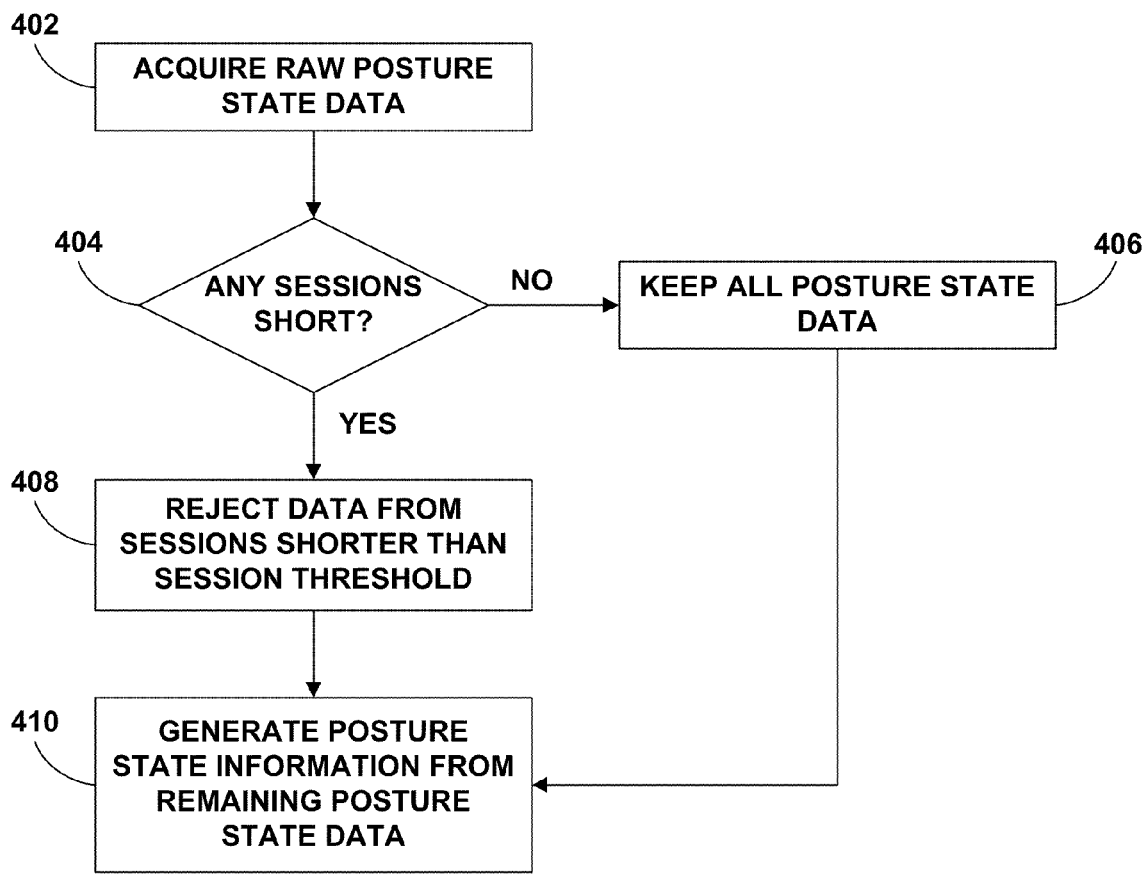
FIG. 25 is a flow diagram illustrating an example method for rejecting raw posture state data stored during a therapy session shorter than a session duration.

FIG. 25 is a flow diagram illustrating an example method for rejecting raw posture state data stored during a session shorter than a session duration. The method of rejecting raw posture state data will be described with regard to clinician programmer 60, but any external programmer 20 may be configured to similarly reject posture state data. As shown in FIG. 25, processor 104 of clinician programmer 60 acquires raw posture state data from IMD 14 (402). Next, processor 104 determines if any of the raw posture state data was stored during a session that was shorter than the session threshold (404).

Each session may be a therapy session corresponding to time between programming sessions, a time between changes in therapy parameters, an active therapy duration in which therapy was delivered to the patient, or some other manner to determine differences in therapy. The programming sessions may be successive programming sessions performed in successive clinic visits, or programming sessions performed in the same clinic visit. The therapy session threshold may be set according to the desires of the clinician, the behavior of patient 12, or dynamically according to the course of therapy. Therefore, the session threshold may be one hour, twenty four hours, one week, or one month, for example. Additionally, the session threshold may be set to a percent of the longest session duration or percent of the average session duration in which raw posture data was stored. For example, the session threshold may be set to less than ten percent of a session duration of the longest session duration in which raw posture state data was stored.

As an illustration, posture state data stored when less than twenty four hours elapsed between programming sessions, e.g., between clinician visits by the patient, may be rejected because of this short therapy session. Posture state information obtained when therapy parameter values are applied for only a short therapy session may not be relied, relative to posture state information obtained for therapy parameter values applied over a longer period of time. In some cases, a patient may leave a clinic and then return the next day to readjust parameters due to lack of efficacy or discomfort, resulting in a short therapy session. As another example, a short therapy session may result when the clinician is interrupted during a programming session. In each case, to avoid adding unreliable data from the short session, or possibly overwriting good data with new data from the short therapy session, posture state information obtained during the short therapy session can be rejected, e.g., discarded rather than stored.

If processor 104 determines that there were no short sessions (404), processor 104 keeps all of the raw posture state data (406) and generates posture state output, such as sleep quality information or proportional posture information. If one or more sessions are shorter than the session threshold (404), processor 104 rejects any raw posture state data from these short sessions (408). Although processor 104 may simply not use the rejected posture state data this one time, processor 104 may also delete any raw posture state data that was rejected. Finally, processor 104 generates posture state output from the remaining posture state data that was not rejected (410). As examples, the generated posture state output may be sleep quality information or proportional posture information. Other types of posture state output may be generated based on the remaining posture state data that was not rejected.

Figure 26A:
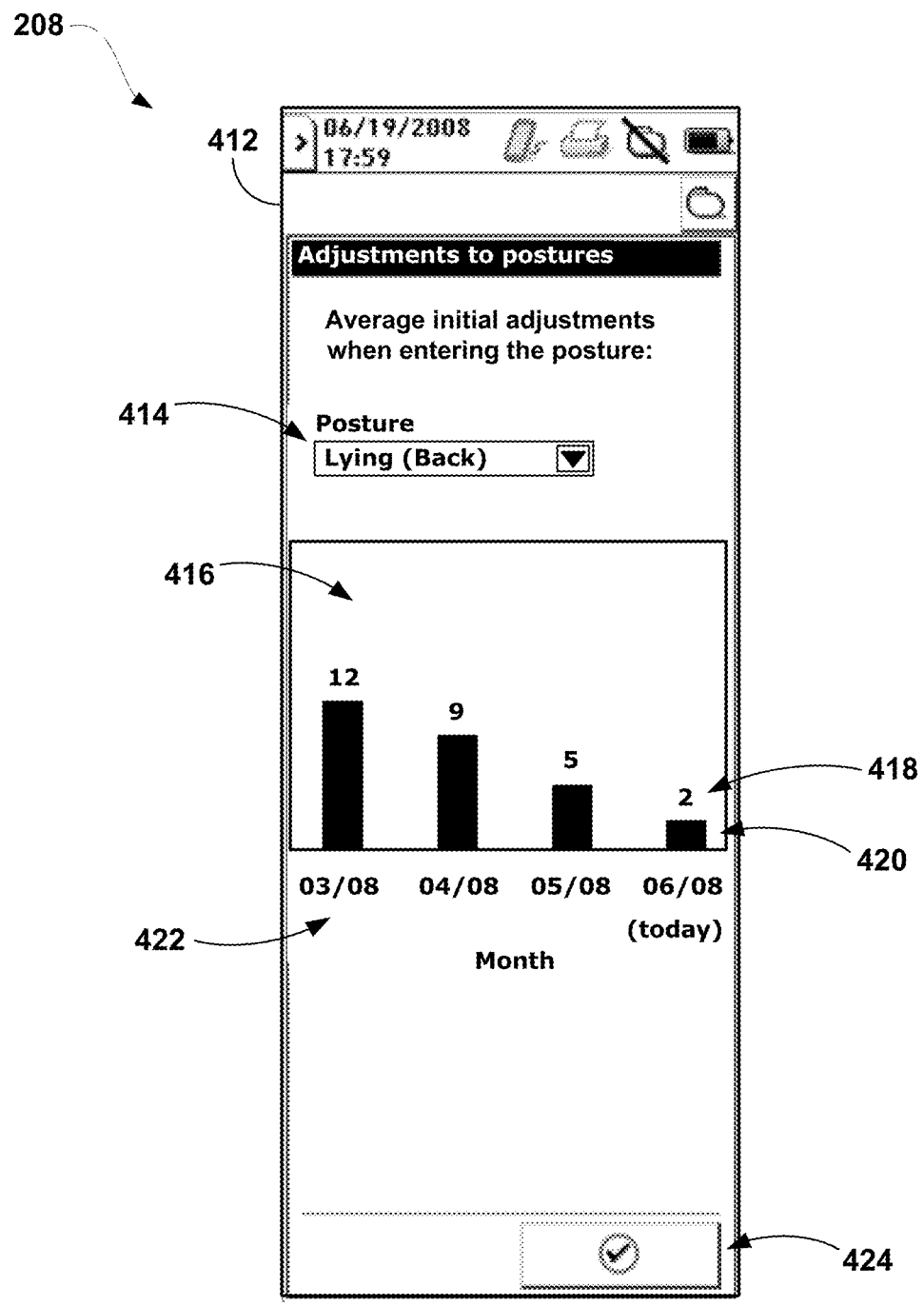
FIG. 26A is a conceptual diagram illustrating an example user interface for presenting a graph that displays the number of initial therapy adjustments that a patient makes when entering into a different posture state.
Figure 26B:
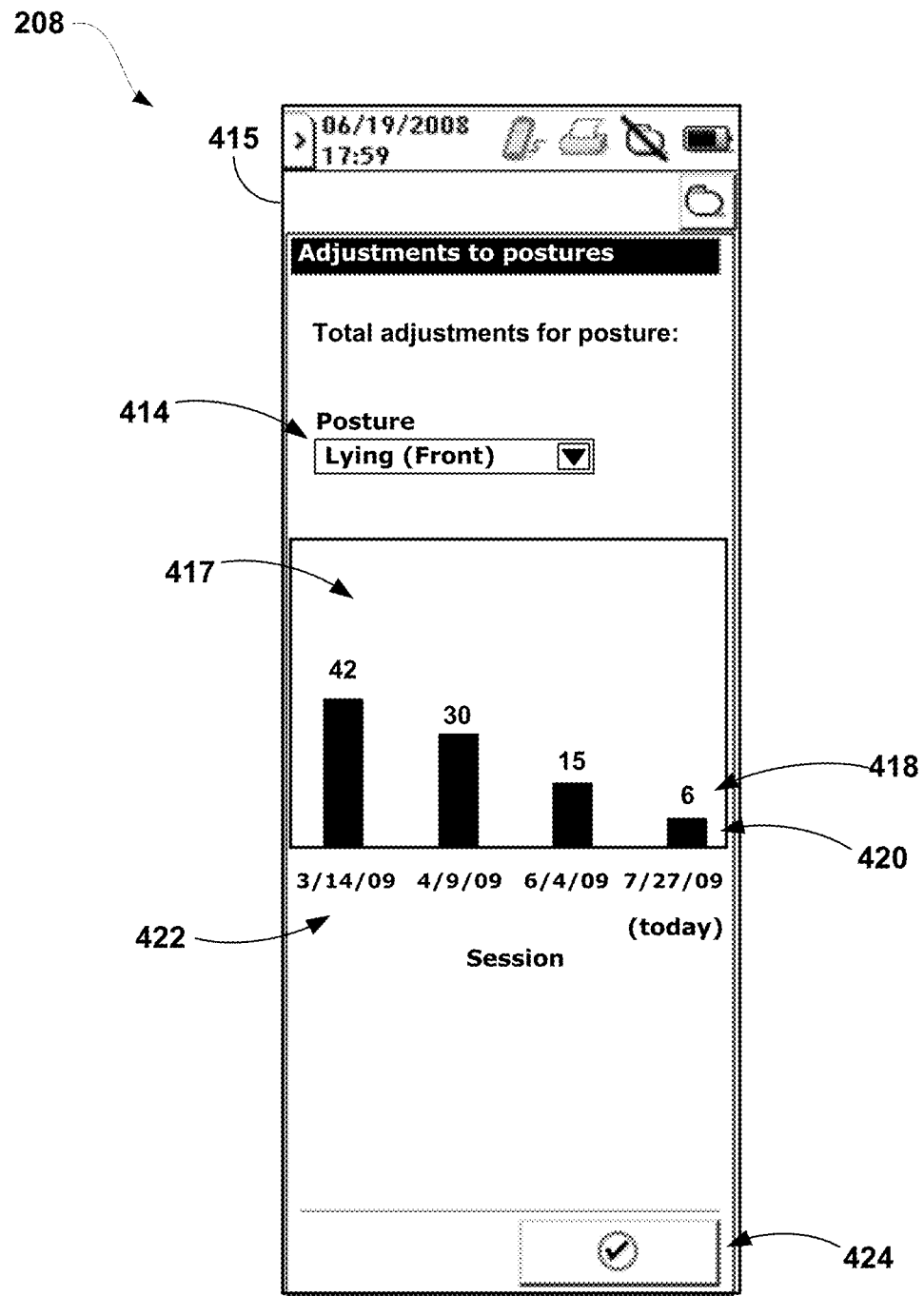
FIG. 26B is a conceptual diagram illustrating an example user interface for presenting a graph that displays the number of therapy adjustments that a patient makes while occupying a posture state.
Figure 26C:
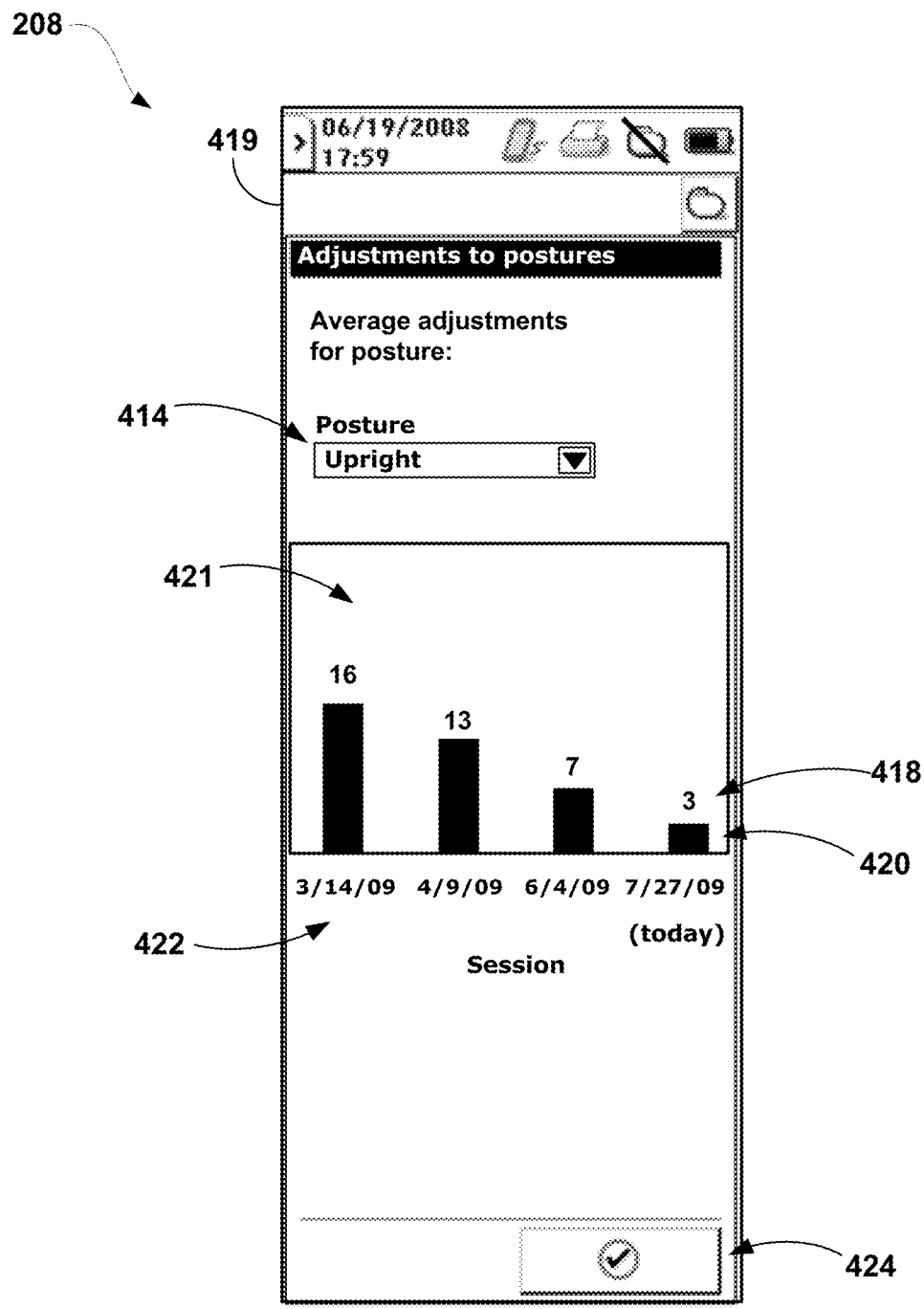
FIG. 26C is a conceptual diagram illustrating an example user interface for presenting a graph that displays an average number of therapy adjustments that a patient makes each time the patient occupies a posture state during a time interval.
Figure 26D:
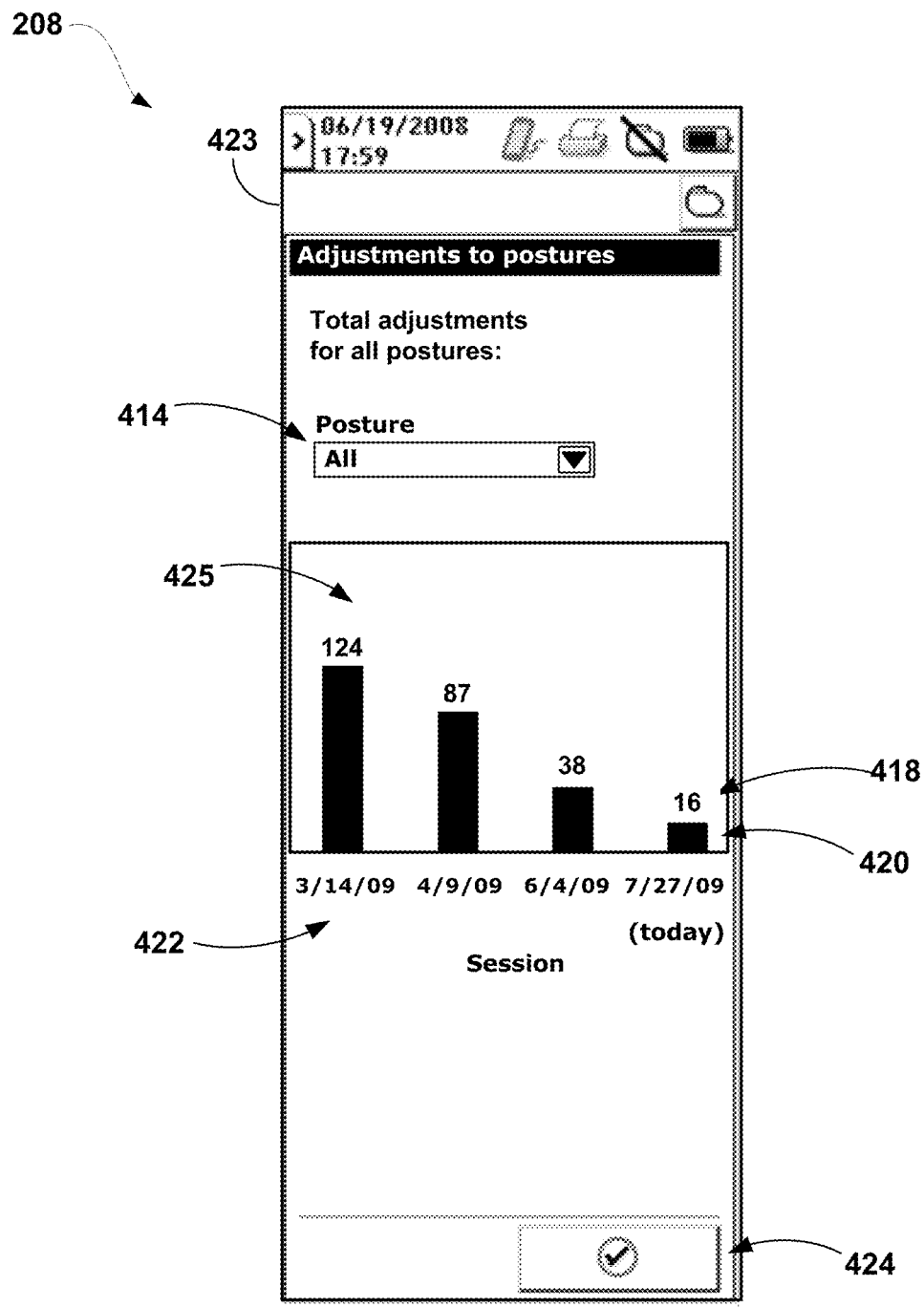
FIG. 26D is a conceptual diagram illustrating an example user interface for presenting a graph that displays a total number of therapy adjustments that a patient makes for all posture states during a time interval.

FIG. 26A is a conceptual diagram illustrating an example user interface 208 for presenting an adjustment graph 416 that displays a number of therapy adjustments 418 made by patient 12 in a time interval. For example, adjustment graph 416 may display the average number of therapy adjustments made by patient 12 when entering into a different posture state. FIG. 26B is a conceptual diagram illustrating an example user interface 208 for presenting an adjustment graph 415 that displays an absolute number of therapy adjustments that patient 12 makes while occupying a posture state during a time interval. FIG. 26C is a conceptual diagram illustrating an example user interface 208 for presenting an adjustment graph 427 that displays an average number of therapy adjustments that patient 12 makes each time the patient occupies a posture state during a time interval. FIG. 26D is a conceptual diagram illustrating an example user interface 208 for presenting an adjustment graph 427 that displays a total number of therapy adjustments that patient 12 makes for all posture states during a time interval. In general, according to the examples of FIGS. 26A-D, a programmer 20 or IMD 14 determines the number of patient adjustments to posture state-responsive therapy delivered to patient 12 over a time interval. Although FIGS. 26A-26D present therapy adjustment information in a graphical form for purposes of illustration, the therapy adjustment information may be presented in other ways, such as in text or a combination of graphics and text.

FIG. 26A illustrates the tracking of an average number of initial adjustments made by patient 12 each time the patient moves to a particular posture state, e.g., within an initial adjustment period following sensing of the posture state, during a time interval. FIG. 26B illustrates the tracking of an absolute number of adjustments made while patient 12 has occupied a particular posture state during a time interval. Alternatively, FIG. 26C illustrates the tracking of an average number of adjustments made by patient 12 each time the patient occupies a given posture state. In some cases, the number of therapy adjustments made by patient 12 for all posture states may be tracked and presented, as illustrated in FIG. 26D. In general, in the examples of FIGS. 26A-26C, IMD 14 may associate therapy adjustments received from patient 12 with posture states occupied by the patient. In the example of FIG. 26D, however, it may not be necessary to associate therapy adjustments with individual posture states.

In each of the examples of FIGS. 26A-26D, the number of patient therapy adjustments may provide objective information that can be used by a clinician to evaluate efficacy of therapy delivered to the patient when the patient makes the therapy adjustments. The therapy may be posture state-responsive therapy that applies different therapy parameter according to the posture state occupied by patient 12. Tracking and presenting the number of patient therapy adjustments, such as initial adjustments per posture state, all adjustments per posture state, or all adjustments for all posture states, may provide an objective indication of the efficacy of the parameters presently being delivered automatically according to the posture state-responsive therapy or a fixed therapy. As described below, the number of patient therapy adjustments may be expressed as an average number per posture or a total number per posture, in a given time interval.

As shown in FIG. 26A, screen 412 of user interface 208 presents the average number of initial therapy adjustments patient 12 makes each time patient 12 changes to a particular posture state. A patient therapy adjustment may be made by a patient by selecting or adjusting one or more parameter values for a current program, e.g., via a patient programmer. For example, an adjustment may be made to one or more of an amplitude, a pulse width, a pulse rate, an electrode combination, or an electrode polarity. In addition, a therapy adjustment may be entered by patient 12 simply selecting a different therapy program to determine the stimulation therapy that is applied. In response to a patient therapy adjustment, IMD 14 may apply the patient therapy adjustment to therapy that is delivered to the patient 12. However, IMD 14 may apply the patient therapy adjustment on a temporary basis while patient 12 resides in the posture state. The next time that patient 12 occupies the posture state, IMD 14 may again apply the existing therapy parameters for the posture state according to the established posture state-responsive therapy programming. In this case, patient 12 may again enter patient therapy adjustments, if desired or necessary to achieve better efficacy.

The therapy adjustments may be made by patient 12 to modify one or more parameters of therapy delivered in a posture state-responsive therapy mode in order to enhance efficacy. Again, analysis of the number of therapy adjustments by a clinician may provide objectification information about the efficacy of the parameters presently applied according to the posture state-responsive therapy delivery during the therapy session. For example, a large number of patient adjustments to therapy parameters may indicate that the level of therapeutic efficacy provided by existing therapy parameters is insufficient. A small number of adjustments may provide an objective indication that existing therapy parameters support better therapeutic efficacy. A clinician may evaluate the number of adjustments in considering whether the existing therapy is acceptable, or whether clinician adjustments to posture state-responsive therapy parameters are advisable. If the number of patient therapy adjustments is tracked for individual posture states, the clinician may adjust parameters for each individual posture state. If the number of patient therapy adjustments is tracked on an overall basis for all posture states, the clinician may evaluate adjustments to parameters relating to various posture states to provide an overall modification of the therapy.

In some cases, therapy adjustments by patient 12 may be made more often at the beginning of therapy, e.g., in earlier therapy sessions, because effective therapy has not yet been established. Over time, however, therapy parameters may be better optimized as the clinician makes adjustments to posture state-responsive therapy parameters in later programming sessions, e.g., based in part on analysis of objective efficacy information such as the number of patient therapy adjustments made overall or for particular postures. As discussed above, during delivery of posture-state responsive therapy, IMD 14 may modify therapy parameters based on patient therapy adjustments to allow IMD 14 to better anticipate what amplitude should be used for each posture state. A clinician may later analyze the number of patient therapy adjustments in order to evaluate possible adjustments to posture state-responsive therapy.

In screen 412 of FIG. 26A, the clinician may review graph 416 to determine how many times patient 12 has needed to adjust therapy parameters in each posture state, on average, during a time interval, such as a day, week, month or therapy session. In the example of FIG. 26A, graph 416 presents an average of initial patient therapy adjustments for a given posture state in each of plurality of monthly time intervals. A patient 12 may occupy each posture state multiple times in a given time interval. Hence, the average number of patient adjustments for a posture state may be the average number of patient adjustments each time the patient occupies the posture state, i.e., for each instance of the posture state. In the example of FIG. 26A, the clinician may select the desired posture state from posture state menu 414, e.g., the lying (back) posture state. Then, user interface 208 presents adjustment graph 416 that includes therapy adjustments 418 and adjustment bars 420 for each of the time intervals 422.

The average number of initial adjustments for a given posture state for each time interval may be displayed simultaneously in screen 412 with the average number of initial adjustments for the given posture for other time intervals, so that a trend may be observed over several time intervals, such as several therapy sessions with different therapy parameters. In the example of FIG. 26A, patient 12 has needed to make fewer initial adjustments, on average, as therapy has progressed from earlier therapy sessions to later therapy sessions, and has only changed therapy twice when moving to the lying back posture, on average, in the most recent time interval. The clinician may select return button 424 to return to the previous screen or to navigate to a menu screen of user interface 208.

The therapy adjustments tracked in FIG. 26A are initial adjustments in the sense that they are adjustments made in an initial adjustment period as patient 12 enters the new posture, rather than adjustments that are made later. Evaluation of initial therapy adjustments may be useful in identifying difficulty in achieving effective therapy upon moving to a new posture state. For example, patient 12 may need to make several changes to amplitude when moving from an upright posture state to a lying back posture state because IMD 14 may not be initially programmed to sufficiently accommodate for the change in posture state. FIG. 26A presents an average number of initial therapy adjustments made for a given posture state each time the patient 12 assumes that posture state in a given time interval, such as a therapy session. As an alternative, user interface 208 may present a cumulative number of initial therapy adjustments made by patient 12 for all instances of a given posture during a time interval. As a further alternative, user interface 208 may present a cumulative number of initial adjustments for all posture states during a time interval.

FIG. 26B presents an absolute number of patient therapy adjustments received for a particular posture state during a given time interval, such as a therapy session. Instead of only initial adjustments received during an initial adjustment period, the adjustments presented in FIG. 26B may include the number of all patient therapy adjustments received while the patient resides in the pertinent posture state during a time interval. The patient therapy adjustments may represent adjustments needed for the patient to reach a desired level of efficacy for the posture state. A greater number of patient adjustments may indicate that the patient has greater difficulty in achieving a desired level of efficacy for a posture state, given posture-state responsive therapy parameters initially applied when the posture state is sensed. Hence, a total number of patient therapy adjustments for multiple instances of a particular posture state may indicate efficacy of posture state-responsive therapy for that posture state. In some cases, a cumulative number of patient therapy adjustments for all posture states may provide an indication of overall efficacy of the posture state-responsive therapy.

With reference to FIG. 26B, using screen 415, a clinician may select a desired posture state from posture state menu 414, e.g., the lying (back) posture state. Then, user interface 208 presents adjustment graph 417 that includes therapy adjustments 418 and adjustment bars 420 for each of the time intervals 422. In FIG. 26B, the number of adjustments for all instances of a given posture state for each time interval may be displayed simultaneously with the number of adjustments for all instances of the given posture for other time intervals, so that a trend may be observed over several time intervals, such as several therapy sessions with different therapy parameters. In the example of FIG. 26B, as in the example of FIG. 26A, patient 12 has needed to make fewer initial adjustments as therapy has progressed from earlier therapy sessions to later therapy sessions. The clinician may select return button 424 to return to the previous screen or to navigate to a menu screen of user interface 208.

The number of patient therapy adjustments presented to a user may be tracked and presented in a variety of ways. For example, the number of patient therapy adjustments presented to a user by user interface 208 may be an absolute number of patient therapy adjustments received for all instances of a given posture during a time interval, as indicated in FIG. 26B. As an alternative, user interface 208 may present an average number of patient therapy adjustments received for a given posture each time patient 12 assumes the posture during a time interval, i.e., for each instance of a posture state. Screen 421 of FIG. 26C shows an adjustment graph 421 that presents the average number of patient adjustments ("Average adjustments for posture") each time a patient 12 enters a posture state in a given time interval. As a further alternative, user interface 208 may present a cumulative number of patient therapy adjustments received for all postures during a time interval. Screen 423 of FIG. 26D shows an adjustment graph 425 that presents a cumulative number of patient therapy adjustments ("Total adjustments for all postures") during different time intervals. In the example of FIG. 26D, it may not be necessary to associate patient therapy adjustments with particular posture states. Rather, IMD 14 may simply count the number of patient therapy adjustments in a time interval.

With further reference to FIG. 26A, determination of which therapy adjustments are to be categorized as initial therapy adjustments associated with entry into a posture state during an initial adjustment period may be accomplished by using an adjustment period timer. In particular, an adjustment period timer may be used to reject therapy adjustments that are not clearly associated with initial entry into a particular posture state. The adjustment timer may start when a new posture state is detected and last for an adjustment period. The adjustment period may last for generally 10 seconds to 60 minutes. More specifically, the adjustment period may be between 30 seconds and 5 minutes. In some examples, the adjustment period may be approximately 3 minutes. During the adjustment period, IMD 14 or patient programmer 30, may associate each therapy adjustment with the current posture state and quantify the associations. The quantified number of initial therapy adjustments may then be reviewed by patient 12 or the clinician.

For example, patient 12 may transition from the upright posture state to the lying back posture state. The adjustment timer starts when IMD 14 detects the new lying back posture state, and the adjustment period is set to 3 minutes. In the first 3 minutes that patient 12 is engaged in the lying back posture state, each patient therapy adjustment to amplitude (or other parameters) is counted and stored as the patient therapy adjustments needed for that lying back posture state. Patient therapy adjustments made after expiration of the adjustment period are not counted as initial therapy adjustments, and can be disregarded in the count for purposes of the example of FIG. 26A. Since the number of therapy adjustments may change in time, e.g., as a clinician adjusts posture state-responsive therapy, the clinician may review this information over a series of time intervals between programming sessions in which posture state-responsive therapy parameters are adjusted by the clinician to determine how therapy is anticipating the desired therapy parameters of patient 12. A user such as a clinician could view a graph via a programmer or other device that shows the number of initial therapy adjustments made by the patient due to posture change. For example, if there was a therapy adjustment, e.g., to amplitude, during an adjustment period between a time a therapy adjustment is made and a time the adjustment can be attributed to a particular posture state, the therapy adjustment could be characterized as an adjustment due to posture change and counted as such. Then, a number of adjustments due to posture change could be presented graphically as an actual number or average number within a time period, such as a day, week, month, therapy session, or the like. The number of adjustments may provide an indication of how often the patient needs to use the programmer to manually adjust therapy for a posture change, and how comfortable the patient is with stimulation after the posture change, thereby providing information that may be useful in programming IMD 14.

Patient therapy adjustments may be associated with a particular posture state if they are received while patient 12 occupies the posture state, i.e., following detection of a given posture and before detection of a different posture state. To limit analysis to initial patient therapy adjustments in some implementations, an adjustment period may be applied, as described above. As a further alternative, in some examples, IMD 14 or programmer 20 may be configured to associate patient therapy adjustments with posture states using a posture search timer and posture stability timer. In particular, IMD 14 or programmer 20 may implement a posture search timer and a posture stability timer for each instance of patient therapy adjustment, i.e., each time a therapy adjustment is received from patient 12. The posture search timer and posture stability timer may be used, for example, to associate patient therapy adjustments with posture states for purposes of the examples of FIGS. 26A-26C.

The posture search timer may have a search period and a posture stability timer may have a stability period that, when used together, allow the system to associate a patient therapy adjustment to a posture state. If the patient therapy adjustment is associated with a posture state, then it can be counted as a patient therapy adjustment for the posture state as in the examples of FIGS. 26A and 26B. If initial therapy adjustments are tracked according to FIG. 26A, an adjustment period also may be applied, in addition to the search timer and the stability timer, to identify initial therapy adjustments. For example, if a patient therapy adjustment satisfies both the search timer and the stability timer, the adjustment period timer still may be applied to reject patient therapy adjustments that were not entered in an initial adjustment period, which may run in parallel with the search and stability periods. For the examples of FIGS. 26B-26D, however, an initial adjustment period is not necessary because all patient therapy adjustments are tracked, instead of just initial therapy adjustments.

In general, the search timer starts each time a patient therapy adjustment is received by programmer 20 or by IMD 14 via programmer 20. The stability timer starts each time a posture state is sensed after a patient therapy adjustment is received. If the stability timer starts within the search period, and the posture state remains stable for the duration of the stability timer, then the patient therapy adjustment can be associated with the posture state and counted. Patient 12 may occupy a posture state multiple times such that there are multiple instances of the sensed posture state. Each time patient 12 occupies the posture state, the patient may enter one or more patient therapy adjustments. Hence, the multiple therapy adjustments may be obtained over multiple instances of the sensed posture state, and associated with the posture state according to the search timer and stability timer, producing a cumulative count for the posture state, e.g., as indicated in the example of FIG. 26B. Alternatively, therapy adjustments may be counted separately for separate instances of posture states so that an average number of adjustments per posture state can be determined, e.g., according to the example of FIG. 26C.

In some examples, clinician programmer 60 may allow the clinician to adjust the search period of the posture search timer and the stability period of the posture stability timer. The posture search timer and the posture stability timer enable IMD 14 to determine the posture state with which a therapy adjustment should be associated. Depending upon the condition of patient 12 or clinician preferences, the clinician may desire to adjust the search period and stability period to accurately reflect the intentions of patient 12. For example, if patient 12 has a habit of adjusting therapy long before making a change to the posture state or patient 12 takes a long time to assume a desired posture state, the clinician may desire to increase the search period and stability period in order to properly associate the therapy adjustment with the intended posture state. In some examples, clinician programmer 60 may suggest appropriate search periods and stability periods for patients diagnosed with particular conditions that may hinder their movement or involve multiple oscillations in posture state before settling on the final posture state.

The search timer starts upon receipt of a patient therapy adjustment. According to one example, in order to associate a therapy adjustment with a posture state, the stability timer for the posture state must start before the end of the search period, and the posture state must not change during the stability period, i.e., the posture state must remain stable. Therefore, the search period and stability period must overlap for the therapy adjustment to be associated with a posture state that is not currently occupied by patient 12 when the therapy adjustment was made.

Generally, the search period may be between approximately 30 seconds and 30 minute minutes, but it may be set to any time desired, including a time that is outside of that range. More specifically, the search period may be between approximately 30 seconds and 5 minutes, or more preferably 2 minutes to 4 minutes in order to provide a reasonable amount of time for patient 12 to be situated in the final desired posture state. In some examples, the search period is approximately 3 minutes. In other cases, shorter search periods may be used, e.g., approximately 1 second to 60 seconds, or approximately 5 seconds to 20 seconds.

In addition, the stability period may be of any time duration desired by the manufacturer or clinician. Generally, the stability period is between approximately 30 seconds and 30 minutes, but it may be set to any time desired, including times outside of that range. More specifically, the stability period may be between approximately 30 seconds and 5 minutes, and more preferably 2 minutes to 4 minutes, in order to ensure that patient 12 is situated in the final desired posture state for a reasonable amount of time and that the final posture state is not just some transitional or interim posture state. In some examples, the stability period is approximately 3 minutes. Although the search period and stability period may have the same duration, they may be different in other examples. In other cases, shorter stability periods may be used, e.g., approximately 1 second to 60 seconds, or approximately 5 seconds to 20 seconds.

Figure 27:
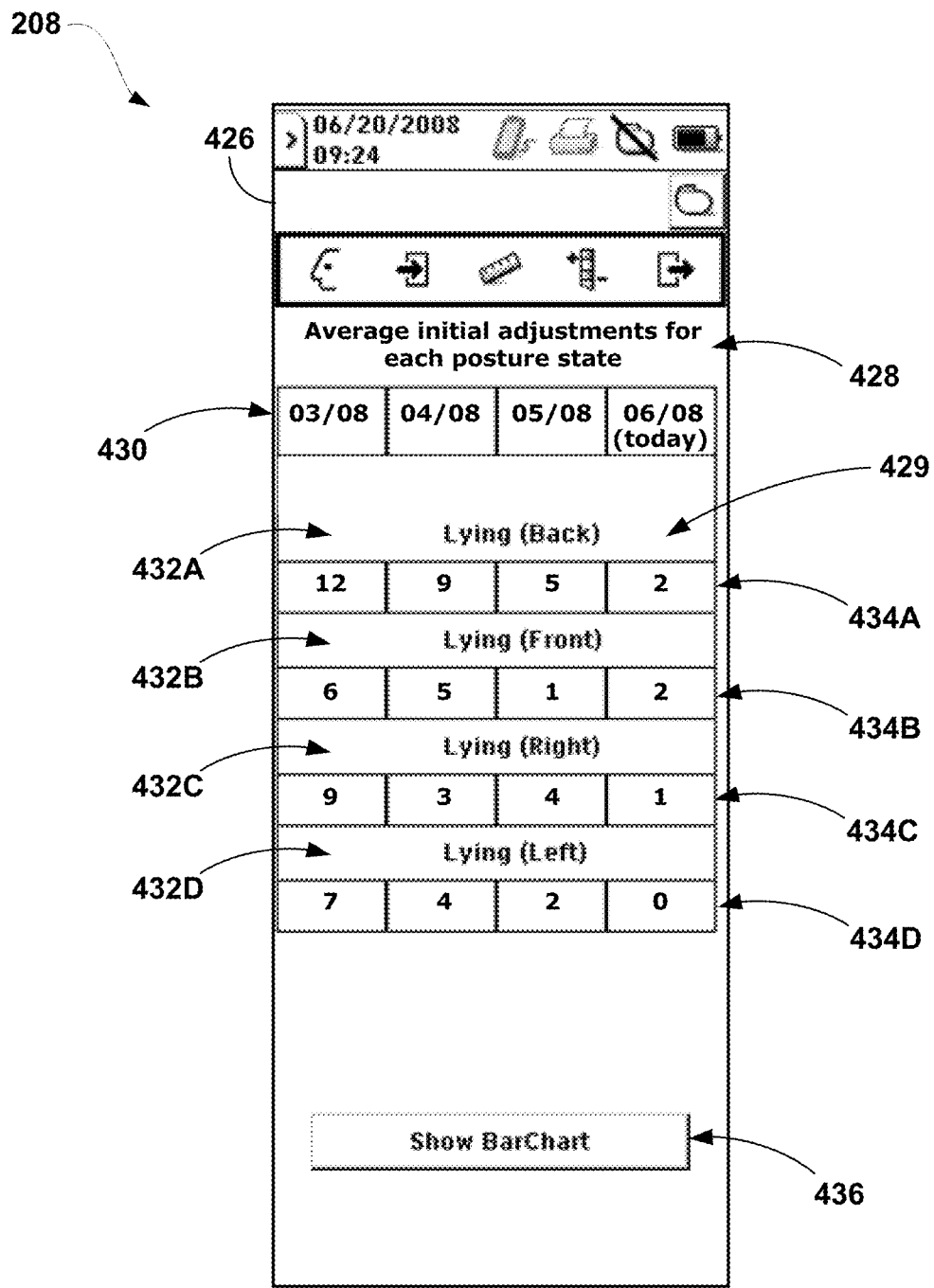
FIG. 27 is a conceptual diagram illustrating an example user interface for presenting a table that displays the number of therapy adjustments the patient makes when entering into a different posture state.

FIG. 27 is a conceptual diagram illustrating an example user interface 208 for presenting a table 429 that displays the number of initial therapy adjustments 434 the patient makes when entering into a different posture state. Again, the overall number or average number of therapy adjustments made by the patient for a posture state could be presented instead of only the initial therapy adjustments, e.g., as indicated in FIGS. 26B and 26C. Alternatively, the overall number of therapy adjustments for all posture states could be presented, e.g., as in the example of FIG. 26D. FIG. 27 is similar to FIG. 26A, except that the number of therapy adjustments are shown numerically and for several posture state. As shown in FIG. 27, screen 426 of user interface 208 presents header 428, time intervals 430, table 429, posture states 432A, 432B, 432C, and 432D (collectively "posture states 432"), therapy adjustments 434A, 434B, 434C, and 434D (collectively "therapy adjustments 434"), and barchart button 436. Again, a representation similar to that of FIG. 27 could be used to display the number of therapy adjustments or average number of therapy adjustments for each posture state in a time interval, as in the examples of FIGS. 26B and 26C.

Header 428 describes the information presented in screen 426, i.e., that screen 426 provides the average initial adjustments for each posture state. Time intervals 430 are the time in therapy to which the presented information relates, and time intervals 430 are shown in consecutive months. Table 429 provides the average number of therapy adjustments 434 for each posture state 432. Although only four posture states 432 are shown, screen 426 may provide any or all of the posture states used by IMD 14. In addition, the clinician may select barchart button 436 to view a graphical representation of table 429, similar to adjustment graph 416 of FIG. 26A.

Figure 28A:
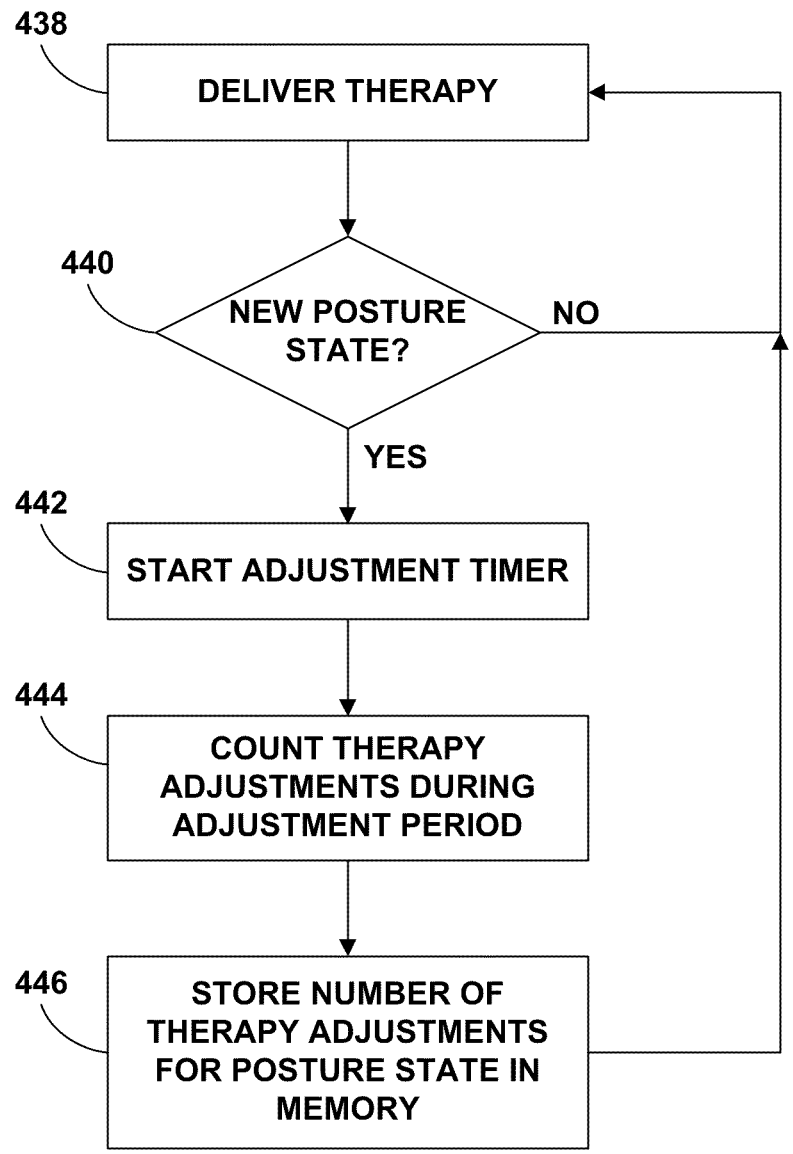
FIG. 28A is a flow diagram illustrating an example method for presenting the number of initial therapy adjustments made in response to entering a new posture state.

FIG. 28A is a flow diagram illustrating an example method for presenting the number of therapy adjustments made in response to entering a new posture state. As shown in FIG. 28, IMD 14 delivers therapy to patient 12 according to groups of programs (438). Once IMD 14 detects that patient 12 enters a new posture state (440), processor 80 of IMD 14 starts the adjustment timer to track any initial therapy adjustments entered by patient 12 (442). Processor 80 then counts each therapy adjustment made by patient 12 during the adjustment period (444). Processor 80 then stores the number of therapy adjustments made for that posture state (446) and continues to deliver therapy (438). In some examples, processor 104 of patient programmer 30 may track and store the therapy adjustments made by patient 12. Processor 80 may store the number of therapy adjustments as a cumulative number for all instances of the posture state, i.e., all times that the patient 12 occupied the posture state during a given time interval. Alternatively, processor 80 may store a separate count for each instance of the posture state in the time interval, so that user interface 208 may present an average number of therapy adjustments for each time the patient 12 entered the posture state.

Figure 28B:
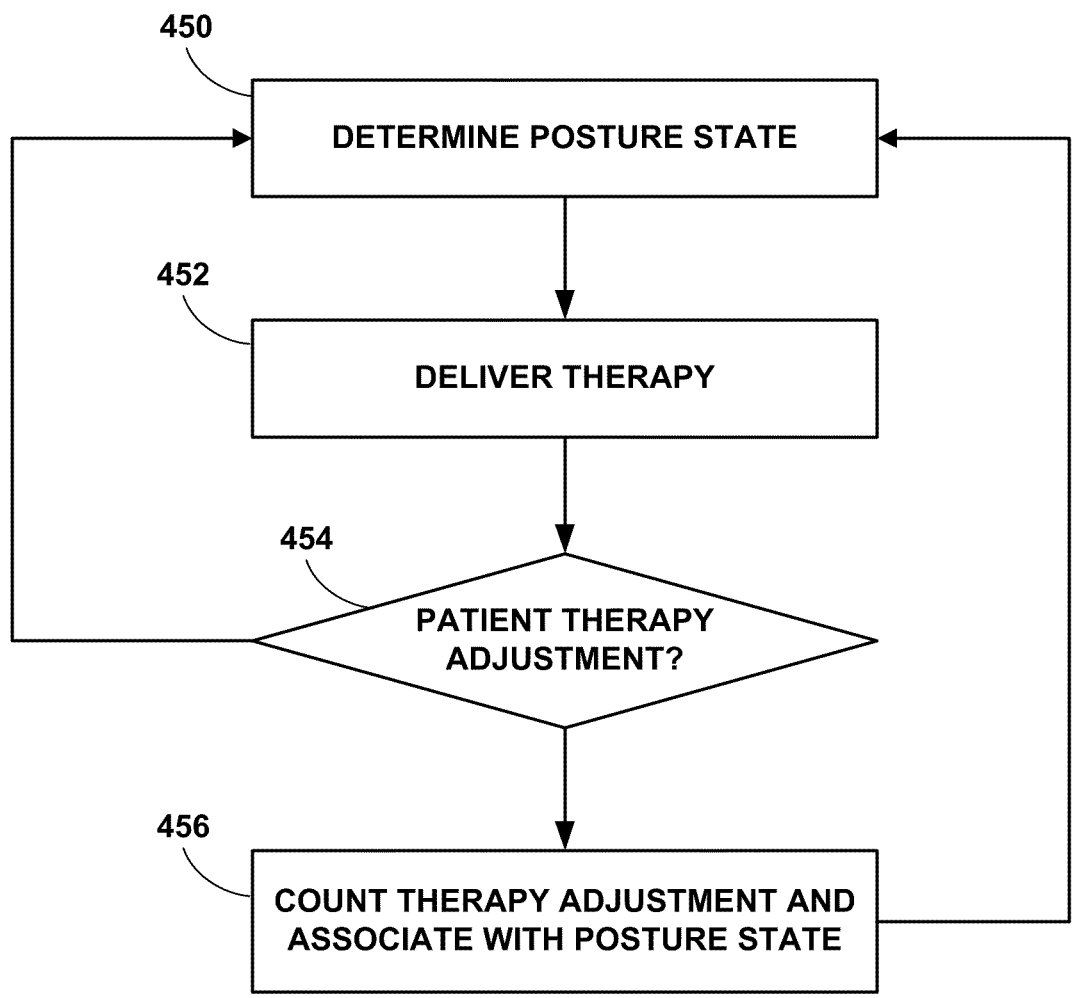
FIG. 28B is a flow diagram illustrating an example method for presenting the number of therapy adjustments that a patient makes while occupying a posture state.

FIG. 28B is a flow diagram illustrating an example method for presenting the number of therapy adjustments that a patient makes while occupying a posture state. In the example of FIG. 28A, processor 80 of IMD 14 determines a posture state of patient 12 (450), and delivers therapy to the patient (452), e.g., with parameters selected according to the posture state in order to support posture state-responsive therapy. While the patient resides in the posture state, processor 80 determines whether a patient therapy adjustment has been received (454). If not, processor 80 updates the posture state (450) and delivers therapy (442). If a patient therapy adjustment is received (454), processor 80 counts the therapy adjustment and associates it with the posture state (456), or an instance of the posture state, and then returns to repeat the determination of posture state (450) and delivery of therapy to the patient (452). In some examples, to associate a therapy adjustment with a posture state, IMD 14 may apply search and stability timers.

Again, the patient therapy adjustment count may be counted cumulatively for all instances of the posture state during a time interval, or counted for each instance of the posture state individually, i.e., for each time patient 12 assumes the posture state. In this manner, the number of patient therapy adjustments may be counted as an absolute number, or an average number for each time the patient assumes the posture state. As a further alternative, in some examples, processor 80 may track a cumulative count of all patient therapy adjustments for all posture state over a therapy interval, e.g., as an overall indication of efficacy. The examples of FIGS. 28A and 28B are provided for purposes of illustration. Other techniques for tracking and presenting the number of patient therapy adjustment may be implemented.

Figure 29:
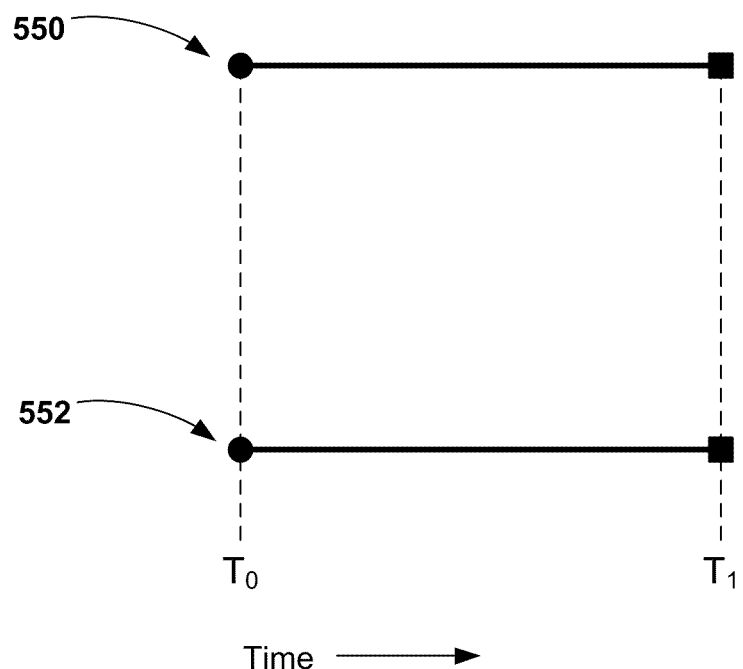
FIG. 29 is a conceptual diagram illustrating an example posture search timer and posture stability timer when a patient remains in one posture state.

FIGS. 29-33 illustrate examples of the application of a search timer and stability timer to associate patient therapy adjustments with posture states so that a total or average number of adjustments may be tracked for different posture states over different time intervals. FIG. 29 is a conceptual diagram illustrating example posture search timer 550 and posture stability timer 552 when patient 12 remains in one posture state. As described in this disclosure, in some examples, IMD 14 must be able to correctly associate each therapy adjustment with a therapy parameter to the intended posture state of patient 12 when the therapy adjustment was made. For example, patient 12 may make therapy adjustments to customize the therapy either after patient 12 moves to a different posture state or in anticipation of the next posture state. IMD 14 may employ posture search timer 550 and posture stability timer 552 to track therapy adjustments and the current posture state of patient 12. Although IMD 14 may associate therapy adjustments of any therapy parameter to a posture state, some examples of IMD 14 may only allow the association of amplitude changes. In this manner, patient 12 may change different therapy parameters such as pulse width, pulse rate, or electrode configuration, but IMD 14 will not store these therapy adjustments as being associated to any posture state in some examples.

Posture search timer 550 has a search period that is a set amount of time that patient 12 has from the time the therapy adjustment is made, when posture search timer 550 starts, to when the final posture state must begin, prior to the expiration of the search period. In other words, in this example, the patient therapy adjustment will not be associated with a posture state entered after the search period has expired. In addition, posture stability timer 552 has a stability period that is a set amount of time that patient 12 must remain within the final posture state for the therapy adjustment made to be associated with the final posture state. Posture stability timer 552 restarts at any time that patient 12 changes posture states. In order to associate a therapy adjustment with a posture state, the stability timer for the posture state must start before the end of the search period, and the posture state must not change during the stability period. Therefore, the search period and stability period must overlap for the therapy adjustment to be associated with a posture state not currently engaged by patient 12 when the therapy adjustment was made.

In the example of FIG. 29, patient 12 made a therapy adjustment to one of the therapy parameters, such as voltage or current amplitude, at time $T_0$. Therefore, posture search timer 550 starts at $T_0$ and runs for a predetermined search period until time $T_1$. When the therapy adjustment is made, posture stability timer 552 also starts at time $T_0$ in the current posture state of patient 12 and runs for the stability period. In the example of FIG. 29, the stability period is the same as the search period. Since patient 12 has not changed to any different posture states between times $T_0$ and $T_1$, the stability period also ends at $T_1$. The therapy adjustment made by patient 12 at time $T_0$ is associated with the posture state sensed between times $T_0$ and $T_1$ because both the search period and stability period overlap. In the example of FIG. 29, posture search timer 550 and posture stability timer 552 may not be needed, but their purpose may become clearer in the following examples.

The search period of posture search timer 550 may be of any time duration desired by a device manufacturer, and the clinician may or may not be permitted to set the search period to a desired value or within a predetermined search range. Generally, the search period may be between approximately 30 seconds and 30 minute minutes, but it may be set to any time desired, including a time that is outside of that range. More specifically, the search period may be between approximately 30 seconds and 5 minutes, or more preferably 2 minutes to 4 minutes in order to provide a reasonable amount of time for patient 12 to be situated in the final desired posture state. In some examples, and as described in the examples of FIGS. 29-33, the search period is approximately 3 minutes. In other cases, shorter search periods may be used, e.g., approximately 1 second to 60 seconds, or approximately 5 seconds to 20 seconds.

In addition, the stability period of posture stability timer 552 may be of any time duration desired by the manufacturer or clinician, where the clinician may or may not be permitted to set the stability period. Generally, the stability period is between approximately 30 seconds and 30 minutes, but it may be set to any time desired, including times outside of that range. More specifically, the stability period may be between approximately 30 seconds and 5 minutes, and more preferably 2 minutes to 4 minutes, in order to ensure that patient 12 is situated in the final desired posture state for a reasonable amount of time and that the final posture state is not just some transitional or interim posture state. In some examples, and as described in the examples of FIGS. 29-33, the stability period is approximately 3 minutes. Although the search period and stability period may have the same duration, they may be different in other examples. In other cases, shorter stability periods may be used, e.g., approximately 1 second to 60 seconds, or approximately 5 seconds to 20 seconds.

As described herein, associating therapy adjustments with intended posture states allow the user to review the number of therapy adjustments made by patient 12 while assuming, or transitioning to, each posture state. The number of therapy adjustments may be used for objectification of efficacy of existing therapy delivered to patient 12.

Figure 30:
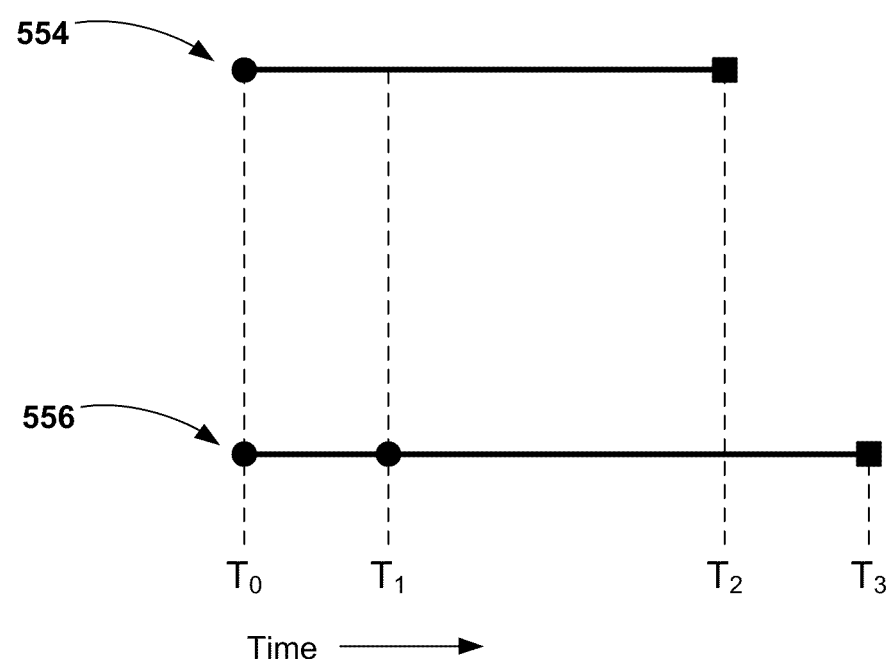
FIG. 30 is a conceptual diagram illustrating an example posture search timer and posture stability timer with one change in posture state.

FIG. 30 is a conceptual diagram illustrating example posture search timer 554 and posture stability timer 556 with one change in posture state. As shown in FIG. 30, patient 12 makes an anticipatory therapy adjustment for the next posture state that patient 12 does not currently occupy. In other words, patient 12 makes a therapy adjustment that the patient may believe is desirable for a given posture in anticipation of transitioning to that posture on an imminent or near-term basis. Posture search timer 554 and posture stability timer 556 start at time $T_0$ when patient 12 makes a therapy adjustment in a current posture state occupied at time $T_0$. At time $T_1$, patient 12 changes to a second posture state that is different than the initial posture state occupied at time $T_0$. Therefore, posture stability timer 556 restarts at time $T_1$, with the change to the new posture state, still within the search duration of posture search timer 554.

In some implementations, patient therapy adjustments received during the search period restart the search period. As a result, a series of patient therapy adjustments that are entered closely in time are, in effect, clustered together such that intermediate adjustments are not counted for the posture state. Instead, the last adjustment in a series of closely spaced (in time) adjustments is associated with the posture state to represent the final adjustment that brought the parameter to a level or value deemed appropriate by the patient 12 for the given posture state. If the search period is three minutes, for example, and the patient 12 makes four adjustments in voltage amplitude within three minutes of one another, e.g., 4.6 volts to 4.8 volts, 4.8 volts to 5.0 volts, 5.0 volts to 5.1 volts, 5.1 volts to 5.3 volts, then the final adjustment value of 5.3 volts may be associated with the posture state.

Each time a new adjustment is entered within the search period, the search period is reset. Once the final adjustment is made, however, if there are no further adjustments for another three minutes, and the stability period is satisfied for the detected posture state, then the final adjustment is associated with the posture state. Clustering of a number of patient therapy adjustments can be useful in order to present a series of closely timed adjustments as a single programming intervention event. Treatment of clustered adjustments as a single programming intervention event may be especially appropriate if the values of the adjustments are also close to one another.

Time $T_2$ indicates the end of posture search timer 554. Consequently, the only posture state that processor 80 of IMD 14 will associate with the therapy adjustment is the second posture state as long as the second posture state satisfies the stability period of posture stability timer 556, i.e., the patient occupies the second posture state for the stability period. At time $T_3$, patient 12 is still in the second posture when the stability period ends, and the therapy adjustment is associated then to the second posture state because the stability period overlapped with the search period.

It should be noted that patient 12 may make additional therapy adjustments within the search period. If this occurs, any previous therapy adjustments made before the search period or stability period is completed are not associated to any posture state. Therefore, both the search period and stability period must lapse, i.e., expire, in order for a therapy adjustment to be associated with a posture state. However, in some examples, IMD 14 may allow therapy adjustments to be associated with posture states as long as the search period has lapsed or no different posture state was sensed during the search period.

Figure 31:
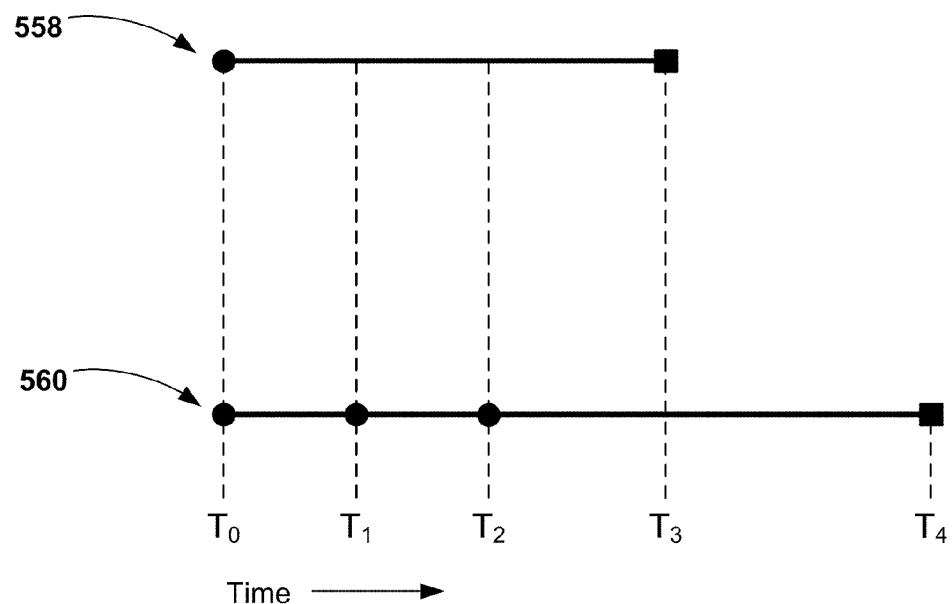
FIG. 31 is a conceptual diagram illustrating an example posture search timer and posture stability timer with two changes in posture states.

FIG. 31 is a conceptual diagram illustrating example posture search timer 550 and posture stability timer 560 with two changes in posture states. As shown in FIG. 31, patient 12 makes an anticipatory therapy adjustment but is engaged in an interim posture state before settling into the final posture state. Posture search timer 558 and posture stability timer 560 both start at time $T_0$ when patient 12 makes a therapy adjustment in a current posture state engaged at time $T_0$.

At time $T_1$, patient 12 changes to a second posture state, or an interim posture state, that is different than the initial posture state engaged at time $T_0$. Therefore, posture stability timer 560 restarts at time $T_1$, still within the search duration of posture search timer 558. At time $T_2$, patient 12 changes to a third posture state, and again posture stability timer 560 restarts. Time $T_3$ indicates the end of posture search timer 558, so the only posture state that processor 80 of IMD 14 will associate with the therapy adjustment is the third posture state begun at time $T_2$ as long as the third posture state satisfies the stability period of posture stability timer 560. At time $T_4$, patient 12 is still in the third posture when the stability period ends, and the therapy adjustment is associated then to the third and final posture state because the stability period of the third posture state overlapped with the search period.

Figure 32:
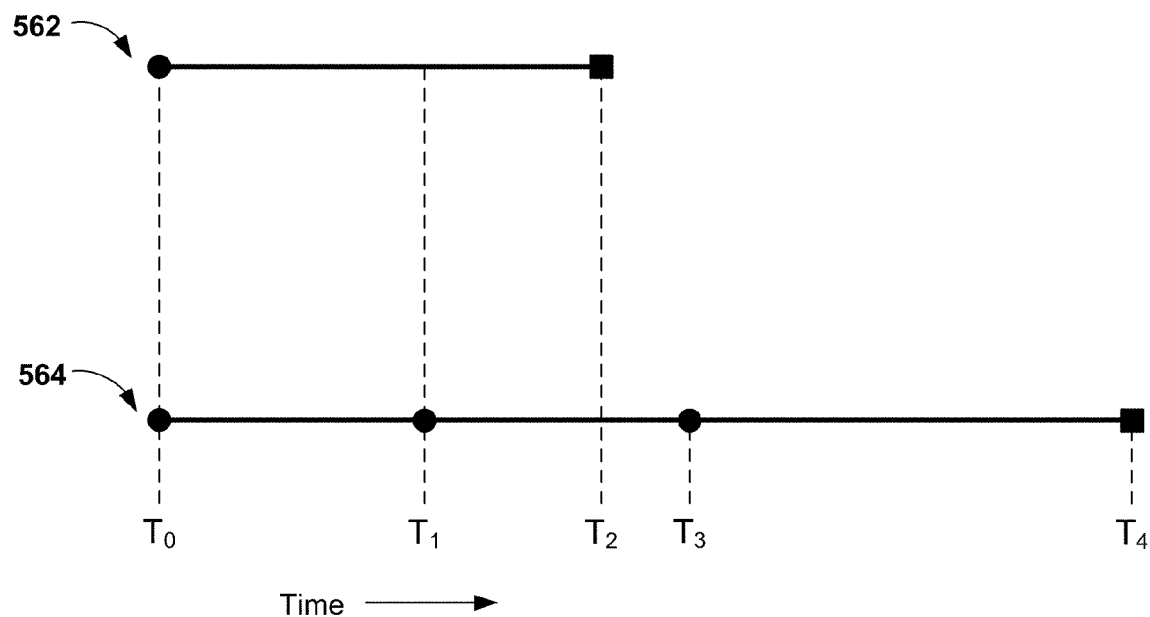
FIG. 32 is a conceptual diagram illustrating an example search timer and posture stability timer with the last posture state change occurring outside of the posture search timer.

FIG. 32 is a conceptual diagram illustrating example search timer 562 and posture stability timer 564 with the last posture state change occurring outside of the posture search timer. As shown in FIG. 32, patient 12 makes an anticipatory therapy adjustment but is engaged in an interim posture state too long before settling into the final posture state for the therapy adjustment to be associated with any posture state. Posture search timer 562 and posture stability timer 564 both start at time $T_0$ when patient 12 makes a therapy adjustment in a current posture state engaged at time $T_0$. At time $T_1$, patient 12 changes to a second posture state, or an interim posture state, that is different than the initial posture state engaged at time $T_0$. Therefore, posture stability timer 564 restarts at time $T_1$, still within the search duration of posture search timer 562.

However, the search timer expires at time $T_2$, before patient 12 changes to a third posture state at time $T_3$, when posture stability timer 564 again restarts. The stability period for the third posture state then expires at time $T_4$. Since the third posture state did not start before the search period expired at time $T_2$, the search period and stability period do not overlap and the therapy adjustment from time $T_0$ is not associated to any posture state. In other examples, therapy adjustments may still be associated with the posture state occupied at time $T_0$ when the search period and last stability period do not overlap.

The following is a further illustration of the example described in FIG. 32 to put the example in context of an example patient scenario. Patient 12 may be engaged in the upright posture state when patient 12 makes the therapy adjustment at time $T_0$. In this example, the search duration is three minutes and the stability duration is also three minutes. After two minutes, or at time $T_1$, patient 12 transitions to the lying left posture to cause processor 80 of IMD 14 to restart posture stability timer 560.

If patient 12 remains within the lying left posture for the full three minutes of the stability duration, then the therapy adjustment would be associated with the lying left posture. However, patient 12 leaves the lying left posture after only two minutes, or at time $T_3$, outside of the search duration. At this point the therapy amplitude made at time $T_0$, will not be associated for the next posture state of patient 12. Therefore, the next posture state may be the lying back posture state. Once IMD 14 senses the lying back posture state, IMD 14 may change therapy according to the therapy parameters associated with the lying back posture because IMD 14 is operating in the automatic posture state-responsive mode. No new associations with the therapy adjustment would be made in the example of FIG. 32.

Figure 33:
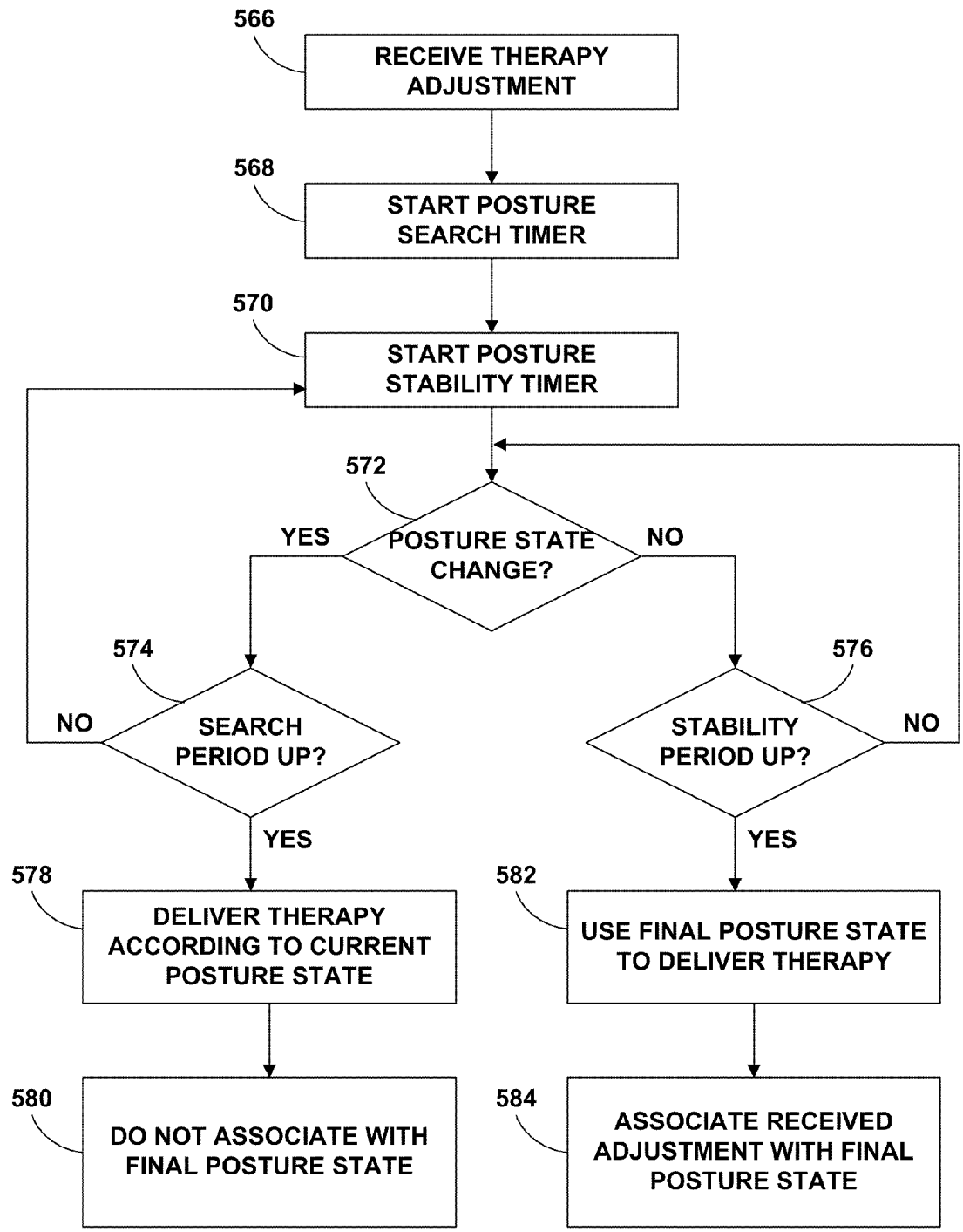
FIG. 33 is a flow diagram illustrating an example method for associating a received therapy adjustment with a posture state.

FIG. 33 is a flow diagram illustrating an example method for associating a received therapy adjustment with a posture state. Although the example of FIG. 17 will be described with respect to patient programmer 30 and IMD 14, the technique may be employed in any external programmer 20 and IMD or other computing device. As shown in FIG. 17, user interface 106 receives the therapy adjustment from patient 12 (566) and processor 80 of IMD 14 immediately starts the posture search timer (568) and the posture stability timer (570).

If the posture state of patient 12 does not change (572), processor 80 checks to determine if the stability period has expired (576). If the stability period has not expired (576), processor 80 continues to sense for a posture state change (572). If the stability period has expired (576), processor 80 uses the final posture state, i.e., the currently sensed posture state, to select therapy parameters to deliver therapy (582). Processor 80 then associates the therapy adjustment with the final posture state and counts the therapy adjustment for that posture state (584).

If processor 80 senses a posture state change (572), processor 80 determines if the search period has expired (574). If the search period has not expired (574), then processor 80 restarts the posture stability timer (570). If the search period has expired (574), then processor 80 automatically delivers posture state-responsive therapy to patient 12 according to the current posture state (578). Processor 80 does not associate the patient therapy adjustment with the final posture state because the search period did not overlap with the stability period (580).

In some examples, as an alternative, a posture stability timer may be employed without the use of a posture search timer. As described with respect to posture stability timer 560, the posture stability timer may be started after a therapy adjustment and reset each time patient 12 changes posture states prior to expiration of the posture stability timer. When the posture stability timer 560 expires, the therapy adjustment may be associated with the posture state that patient 12 is occupying at that time. In this manner, the therapy adjustment may be associated with the first stable posture state, i.e., the first posture state that remains stable for the duration of the posture stability timer, after the therapy adjustment, regardless of the amount of time that has past since the therapy adjustment. Hence, in some implementations, processor 80 may apply only a stability timer without a search timer.

In some example implementations, processor 80 may not change posture state-responsive therapy to patient 12 until the stability period expires. In this case, the posture stability timer may run independently of the posture search timer to track posture states independently of therapy adjustments. Therefore, in some cases, IMD 14 may not perform automatic posture responsive stimulation until the posture state of patient 12 is stable and the stability period has expired. In this manner, patient 12 may not be subjected to rapidly changing therapy when transitioning between multiple posture states. Alternatively, IMD 14 may employ a separate posture stability timer for changing therapy during automatic posture state-responsive therapy from the therapy adjustment related posture stability timer as described in this disclosure.

This disclosure may provide multiple features to a user. For example, a clinician may quickly review the posture states engaged by the patient during stimulation therapy to assess therapy efficacy. Sleep quality information may be viewed to identify the number of times the patient is changing posture states during sleep. Proportional posture information may be viewed to identify how long patient 12 engages in each types of posture due to the therapy being delivered. In this manner, the clinician may be able to identify posture state trends with patient 12 and make adjustments to therapy parameters as needed to continually increase the effectiveness of stimulation therapy. Further, posture state data stored during short sessions may be rejected from use in generating posture state information.

In accordance with various aspects of this disclosure, a medical device system may support sleep quality monitoring based on transitions between different posture states, e.g., lying back, lying front, lying left, lying right, upright, during a sleep period to objectively evaluate sleep quality. Transitions between different lying posture states may be particularly useful in evaluating sleep quality. In addition, tracking various parameters such as different posture states, amount of time spent in different posture states, percentage of time in different posture states, averages, ranges, or other trending data or statistical measures for presentation to a clinician may support objectification of patient condition and patient response to therapy.

In addition, a medical device system may present information relating to the number of posture state changes assumed by a patient in a time interval and the number of patient therapy adjustments made by a patient a time interval. The number of patient therapy adjustments made by a patient may provide an indication of a level of efficacy provided by posture state-responsive therapy. If the patient has made a large number of adjustments, a clinician may infer that posture state-responsive therapy should be adjusted to provide a higher level of efficacy. In some cases, the number of patient therapy adjustments may be monitored for each of the posture states, such that efficacy of the posture state-responsive therapy may be evaluated for each posture state. The number of patient therapy adjustments may be presented as an absolute number or an average number of adjustments for a given time interval. In some cases, the number of patient therapy adjustments may be a number or average number of initial adjustments made within an adjustment period following a posture state change.

Various aspects of the techniques described in this disclosure may be implemented within an IMD, an external programmer, or a combination of both. Moreover, in some embodiments, information may be processed by the IMD, programmer or a dedicated processing device such as a network server. For example, posture state information may be stored in raw form in an IMD and retrieved from the IMD by an external programmer or other external device for generation of proportional posture information and/or sleep quality information. Alternatively, the IMD may process the posture state information at least partially for retrieval by an external device. In some cases, an IMD may be configured to generate proportional posture information and/or sleep quality information for retrieval by an external device. Accordingly, the particular implementations described in this disclosure are presented for purposes of illustration and without limitation as to the techniques broadly described in this disclosure.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that my benefit from the subject matter of this disclosure.

Many embodiments of the invention have been described. Various modifications may be made without departing from the scope of the claims. These and other embodiments are within the scope of the following claims.

The invention claimed is:

1. A method comprising:
 delivering therapy, during a time period, via a medical device to a patient in response to determined posture states of the patient, wherein the determined posture states include a plurality of different lying posture states;
 obtaining, with a computing device, posture state data sensed by the medical device for the patient;
 generating, with at least one processor of the computing device, sleep quality information based on lying posture state changes indicated by the posture state data, wherein the posture state data indicates lying posture state changes during the time period in which the medical device delivers the therapy to the patient in response to the determined posture states of the patient; and
 presenting the sleep quality information to a user via a user interface of the computing device.

2. The method of claim 1, wherein the medical device comprises an implantable medical device, and wherein obtaining posture state data comprises obtaining the posture state data from the implantable medical device.

3. The method of claim 2, wherein the implantable medical device is configured to sense the posture state data, and determine a posture state occupied by the patient based on the posture state data, and deliver electrical stimulation to the patient based on the determined posture state of the patient.

4. The method of claim 1, wherein presenting the sleep quality information further comprises presenting a sleep quality graph that graphically presents the sleep quality information.

5. The method of claim 1, further comprising generating the sleep quality information based on a number of changes from the plurality of different lying posture states during the time period.

6. The method of claim 1, wherein generating the sleep quality information comprises generating sleep quality information for each of a plurality of time intervals during the time period, wherein the sleep quality information for each of the time intervals indicates a number of changes from the plurality of different lying posture states during the respective time interval.

7. The method of claim 1, wherein generating sleep quality information comprises generating the sleep quality information based on the lying posture state changes indicated by the posture state data, and wherein the sleep quality information indicates a number of changes from each of the plurality of different lying posture states during the time period.

8. The method of claim 7, wherein the number of changes includes a daily average number of the changes over the time interval, and wherein the time interval is one of a week, a month, a year, or a time between successive programming sessions for the medical device.

9. The method of claim 1, wherein the sleep quality information indicates a number of changes from each of the plurality of different lying posture states during the time period, and wherein the number of changes is one of a number of changes from each of the lying posture states to a different one of the lying posture states or a number of changes from each of the lying posture states.

10. The method of claim 1, wherein the sleep quality information indicates a number of changes from each of the plurality of different lying posture states to each of the other lying posture states in the plurality of different lying posture states during the time period.

11. The method of claim 1, further comprising generating the sleep quality information based on a number of changes from the plurality of different lying posture states during the time period, wherein the lying posture states include a lying front posture state, a lying back posture state, a lying right posture state, and a lying left posture state.

12. A system comprising:
 a medical device configured to deliver therapy to a patient;

at least one processor that controls the medical device to deliver, during a time period, the therapy to the patient in response to determined posture states of the patient, wherein the determined posture states include a plurality of different lying posture states, obtains posture state data sensed by the medical device for the patient, and generates sleep quality information based on lying posture state changes indicated by the posture state data; and a user interface that presents the sleep quality information to a user, wherein the posture state data indicates lying posture state changes during the time period in which the medical device delivers the therapy to the patient in response to the determined posture states of the patient.

13. The system of claim 12, further comprising a telemetry interface, wherein the medical device comprises an implantable medical device, and the at least one processor is configured to obtain the posture state data from the implantable medical device via the telemetry interface.

14. The system of claim 13, wherein the system further comprises the implantable medical device and a programmer for the implantable medical device, the programmer includes the at least one processor and the user interface, and the implantable medical device is configured to sense the posture state data, determine a posture state occupied by the patient based on the posture state data, and deliver electrical stimulation to the patient based on the determined posture state of the patient.

15. The system of claim 12, wherein the sleep quality information presented by the user interface comprises a sleep quality graph that graphically presents the sleep quality information.

16. The system of claim 12, wherein the at least one processor generates the sleep quality information based on a number of changes from the plurality of different lying posture states during the time period.

17. The system of claim 12, wherein the at least one processor generates sleep quality information for each of a plurality of time intervals during the time period, wherein the sleep quality information for each of the time intervals indicates a number of changes from the plurality of different lying posture states during the respective time interval.

18. The system of claim 12, wherein the at least one processor generates the sleep quality information based on the lying posture state changes indicated by the posture state data, and wherein the sleep quality information indicates a number of changes from each of the plurality of different lying posture states during the time period.

19. The system of claim 18, wherein the number of changes includes a daily average number of the changes over the time period, and wherein the time period is one of a week, a month, a year, or a time between successive programming sessions for the medical device.

20. The system of claim 12, wherein the sleep quality information indicates a number of changes from each of the plurality of different lying posture states during the time period, and wherein the number of changes is one of a number of changes from each of the lying posture states to a different one of the lying posture states or a number of changes from each of the lying posture states.

21. The system of claim 12, wherein the sleep quality information indicates a number of changes from each of the plurality of different lying posture states to each of the other lying posture states in the plurality of different lying posture states during the time period.

22. The system of claim 21, wherein the at least one processor generates the sleep quality information based on a number of changes from the plurality of different lying posture states during the time period, the lying posture states include a lying front posture state, a lying back posture state, a lying right posture state, and a lying left posture state.

23. A medical device system comprising:

an implantable medical device configured to deliver therapy to a patient;

a telemetry interface;

at least one processor that controls the implantable medical device to deliver, during a time period, the therapy to the patient in response to determined posture states of the patient, wherein the determined posture states include a plurality of different lying posture states, obtains posture state data sensed by the implantable medical device via the telemetry interface, and generates sleep quality information based on lying posture state changes indicated by the posture state data; and a user interface that presents the sleep quality information to a user, wherein the posture state data indicates lying posture state changes during the time period in which the implantable medical device delivers the therapy to the patient in response to the determined posture states of the patient.

24. The medical device system of claim 23, wherein the implantable medical device is configured to deliver electrical stimulation to the patient, and the at least one processor is configured to transmit electrical stimulation programming information to the implantable medical device via the telemetry interface.

25. The medical device system of claim 23, wherein the sleep quality information presented by the user interface comprises a sleep quality graph that graphically presents the sleep quality information.

26. The medical device system of claim 23, wherein the at least one processor generates the sleep quality information based on a number of changes from the plurality of different lying posture states during the time period.

27. The medical device system of claim 23, wherein the at least one processor generates the sleep quality information based on the lying posture state changes indicated by the posture state data, and wherein the sleep quality information indicates a number of changes from the plurality of different lying posture states during the time period.

28. The device of claim 23, wherein the sleep quality information indicates a number of changes from each of the plurality of different lying posture states during the time period.

29. The medical device system of claim 28, wherein the number of changes includes a daily average number of the changes over the time period, and wherein the time period is one of a week, a month, a year, or a time between successive programming sessions for the medical device.

30. The medical device system of claim 23, wherein the sleep quality information indicates a number of changes from each of the plurality of different lying posture states during the time period, and wherein the number of changes is one of a number of changes from each of the lying posture states to a different one of the lying posture states or a number of changes from each of the lying posture states.

31. The medical device system of claim 23, wherein the sleep quality information indicates a number of changes from each of the plurality of different lying posture states to each of the other lying posture states in the plurality of different lying posture states during the time period.

32. The medical device system of claim 31, wherein the at least one processor generates the sleep quality information based on a number of changes from the plurality of different lying posture states during the time period, wherein the lying posture states include a lying front posture state, a lying back posture state, a lying right posture state, and a lying left posture state.

33. A system comprising:
means for delivering therapy, during a time period, to a patient in response to determined posture states of the patient, wherein the determined posture states include a plurality of different lying posture states;
means for obtaining posture state data sensed by the medical device for the patient;
means for generating sleep quality information based on lying posture state changes indicated by the posture state data; and
means for presenting the sleep quality information to a user via a user interface, wherein the posture state data indicates lying posture state changes during a time period in which the medical device delivers therapy to the patient in response to determined posture states of the patient.

34. The system of claim 33, wherein the means for presenting the sleep quality information further comprises means for presenting a sleep quality graph that graphically presents the sleep quality information.

35. The system of claim 33, further comprising means for generating the sleep quality information based on a number of changes from the plurality of different lying posture states during the time period.

36. The system of claim 33, further comprising:
means for determining a posture state occupied by the patient based on the posture state data; and
means for delivering therapy to the patient based on the determined posture state of the patient.

37. The system of claim 33, wherein the sleep quality information indicates a number of changes from each of the plurality of different lying posture states the time period.

38. The system of claim 33, wherein the means for generating sleep quality information based on the posture state data comprises means for generating the sleep quality information based on a number of changes from the plurality of different posture states during the time period, wherein the lying posture states include a lying front posture state, a lying back posture state, a lying right posture state, and a lying left posture state.

39. The system of claim 12, wherein the medical device is configured to sense the posture state data of the patient during the time period.

40. The system of claim 23, wherein the at least one processor is configured to sense the posture state data.

41. The system of claim 33, further comprising means for sensing the posture state data of the patient via the medical device.

* * * * *